(12) United States Patent
Labhasetwar et al.

(10) Patent No.: US 10,729,659 B2
(45) Date of Patent: Aug. 4, 2020

(54) NANOGEL-MEDIATED DRUG DELIVERY

(71) Applicant: The Cleveland Clinic Foundation, Cleveland, OH (US)

(72) Inventors: Vinod Labhasetwar, Solon, OH (US); Sivakumar Vijayaraghavalu, Mayfield Heights, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 0 days.

(21) Appl. No.: 16/201,505

(22) Filed: Nov. 27, 2018

(65) Prior Publication Data
US 2019/0091161 A1     Mar. 28, 2019

Related U.S. Application Data

(60) Division of application No. 15/011,467, filed on Jan. 29, 2016, now Pat. No. 10,206,885, which is a continuation of application No. 14/046,343, filed on Oct. 4, 2013, now abandoned.

(60) Provisional application No. 61/710,499, filed on Oct. 5, 2012.

(51) Int. Cl.
| | |
|---|---|
| *A61K 9/51* | (2006.01) |
| *A61K 45/06* | (2006.01) |
| *A61K 31/706* | (2006.01) |
| *A61K 31/704* | (2006.01) |
| *A61K 31/7068* | (2006.01) |

(52) U.S. Cl.
CPC .............. *A61K 9/51* (2013.01); *A61K 9/5138* (2013.01); *A61K 31/704* (2013.01); *A61K 31/706* (2013.01); *A61K 31/7068* (2013.01); *A61K 45/06* (2013.01)

(58) Field of Classification Search
CPC .. A61K 9/5138; A61K 31/706; A61K 31/704; A61K 45/06; A61K 31/7068; A61K 9/51; A61K 2300/00
See application file for complete search history.

(56) References Cited

U.S. PATENT DOCUMENTS

| | | | |
|---|---|---|---|
| 7,727,554 | B2 | 6/2010 | Labhasetwar et al. |
| 10,206,885 | B2 | 2/2019 | Labhasetwar et al. |
| 2014/0100182 | A1 | 4/2014 | Labhasetwar et al. |
| 2016/0250152 | A1 | 9/2016 | Labhasetwar et al. |

OTHER PUBLICATIONS

Abeysinghe, H.R., et al., "The role Of The THY1 Gene In Human Ovarian Cancer Supression Based On Transfection Studies", *Cancer Genet. Cytogenet.*, 149: 1-10 (2004).

Brown, R. and Plumb, J.A., "Demethylation Of DNA By Decitabine In Cancer Chemotherapy", *Expert Rev. Anticancer Ther.*, 4(4): 501-510 (2004).
Chen, C.Y., et al., "SOCS1 Methylation In Patients With Newly Diagnosed Acute Myeloid Leukemia", *Genes Chromosomes Cancer*, 37(3): 300-305 (2003).
Mani, S. and Herceg, Z., "DNA Demethylating Agents And Epigenetic Therapy Of Cancer", *Adv. Genet.*, 70: 327-340 (2010).
May, F.E., et al., "Expression And Motogenic Activity Of TFF2 In Human Breast Cancer Cells", *Peptides*, 25(5): 865-872 (2004).
McCawley, L.J. and Matrisian, L.M., "Matrix Metalloproetinases: Multifunctional Contributors To Tumor Progression", *Molecular Medicine Today*, 6(4): 149-156 (2000).
Melixetian, M.B., et al., "Altered Expression Of DNA-Topoisomerase IIα Is Associated With Increased Rate Of Spontaneous Polyploidization In Etoposide Resistant K562 Cells", *Leukemia Research*, 24(10): 831-837 (2000).
Nyce, J.W., "Drug-Induced DNA Hypermethylation: A Potential Mediator Of Acquired Drug Resistance During Cancer Chemotherapy", *Mutat. Res.*, 386(2): 153-161 (1997).
Qin, J.J., et al., "Development Of A LCST Membrane Forming System For Cellulose Acetate Ultrafiltration Hollow Fiber", *Separation And Purification Technology*, 42(3): 291-295 (2005).
Von Hoff, D.D., et al., "Risk Factors For Doxorubicin-Induced Congestive Heart Failure", *Ann. Intern. Med.*, 91(5): 710-717 (1979).
Walker, J.V. and Nitiss, J.L., "DNA Topoisomerase II As A Target for Cancer Chemotherapy", *Cancer Investigation*, 20(4): 570-589 (2002).
Yallapu, M.M., et al., "Synthesis, Characterization and Antiproliferative Activity Of Rapamycin-Loaded Poly(N-Isopropylacrylamide)-Based nanogels In Vascular Smooth Muscle Cells", *Journal of Biomedical Nanotechnology*, 4(1): 16-24 (2008).
Yoo, C.B. and Jones, P.A., "Epigenetic Therapy Of Cancer: Past, Present and Future", *Nature Reviews Drug Discovery*, 5(1): 37-50 (2006).
Yoshikawa, H., et al., "SOCS-1, A Negative Regulator Of The JAK/STAT Pathway, Is Silenced By Methylation In Human Hepatocellular Carcinoma And Shows Growth-Supression Activity", *Nature Genetics*, 28(1): 29-35 (2001).
Carr, B.I., et al., "Carcinogenicity And Haemoglobin Synthesis Induction By Cytidine Analogues", *Br J Cancer*, 57: 395-402 (1988).
Chan, C.K. and Chu, I.M., "In Vitro Degradation Of Poly(Sebacic Anhydride-Co-Ethylene Glycol)", *Materials Chemistry and Physics*, 88: 59, v. 66 (2004).

(Continued)

*Primary Examiner* — Satyendra K Singh
(74) *Attorney, Agent, or Firm* — Hamilton, Brook, Smith & Reynolds, P.C.

(57) ABSTRACT

Provided herein are methods of inhibiting proliferation of one or more tumor cells comprising contacting the one or more tumor cells with a composition comprising one or more epigenetic drugs that inhibit one or more epigenetic mechanisms of the tumor cells, wherein the one or more epigenetic drugs are encapsulated in a nanogel. The invention is also directed to methods of treating a tumor, metastasis of a tumor or a combination thereof in an individual in need thereof. The invention is also directed to a method of sequentially delivering one or more epigenetic drugs that alter one or more epigenetic mechanisms of a tumor cell and one or more chemotherapeutic drugs to an individual that has a tumor. Compositions which comprise one or more epigenetic drugs that alter one or more epigenetic mechanisms of a tumor cell, wherein the one or more epigenetic drugs are encapsulated in a nanogel.

17 Claims, 31 Drawing Sheets

(56) References Cited

OTHER PUBLICATIONS

Davies, B., et al., "Activity Of Type IV collagenases In Benign And Malignant Breast Disease", *Br J Cancer*, 67: 1126-1131 (1993).

Fukushima, N., et al., "Aberrant Methylation Of Suppressor of Cytokine Signalling-1 (SOCS-1) Gene In Pancreatic Ductal Neoplasms", *Br J Cancer*, 89: 338-343 (2003).

Galm, O., et al., "SOCS-1, A Negative Regulator Of Cytokine Signaling, Is Frequently Silenced By Methylation In Multiple Myeloma", *Blood*, 101: 2784-2788 (2003).

Goffin, J. and Eisenhauer, E., "DNA Methyltransferase Inhibitors-State Of The Art", *Annals of Oncology*, 13: 1699-1716 (2002).

Hequet, O., et al., "Subclinical Late Cardiomyopathy After Doxorubicin Therapy For Lymphoma In Adults", *Journal of Clinical Oncology*, 22(10): 1864-1871 (2004).

Hershman, D.L., et al., "Doxorubicin, Cardiac Risk Factors, And Cardiac Toxicity In Elderly Patients With Diffuse B-Cell Non-Hodgkin's Lymphoma", *Journal of Clinical Oncology*, 26(19): 3159-3165 (2008).

Lee, T. L., et al., "Epigenetic Modification Of SOCS-1 Differentially Regulates STAT3 Activation In Response to Interleukin-6 Receptor And Epidermal Growth Factor Receptor Signaling Through JAK And/Or MEK In Head And Neck Squamous Cell Carcinomas", *Molecular Cancer Therapeutics*, 5: 8-19 (2006).

Limat, S., et al., "Early Cardiotoxicity Of The CHOP Regimen In Aggressive Non-Hodgkin's Lymphoma", *Annals of Oncology*, 14: 277-281 (2003).

Lung, H.L., et al., "THY1 Is A Candidate Tumour Suppressor Gene With Decreased Expression In Metastatic Nasoparyngeal Carcinoma", *Oncogene*, 24: 6525-6532 (2005).

Mund, C., et al., "Characterization Of DNA Demethylation Effects Induced by 5-Aza-2'—Deoxycytidine In Patients With Myelodysplastic Syndrome", *Cancer Research*, 65: 7086-7090 (2005).

Neuwirt, H., et al., "Suppressor Of Cytokine Signaling (SOCS)-1 Is Expressed In Human Prostate Cancer And Exerts Growth-Inhibitory Function Through Down-Regulaltion Of Cyclins And Cyclin-Dependent Kinases", *The American Journal of Pathology*, 174(5): 1921-1930 (2009).

Park, Y, et al.,"SOCS1 Induced By NDRG2 Expression Negatively Regulates STAT3 Activation in Breast Cancer Cells", *Biochemical and Biophysical Research Communications*, 363: 361-367 (2007).

Rivenbark, A.G., et al., "DNA Methylation-Dependent Silencing of CST6 In Human Breast Cancer Cell Lines", *Laboratory Investigation*, 86: 1233-1242 (2006).

Rottapel, R., et al., "The Tumor Suppressor Activity Of SOCS-1", *Oncogene*, 21: 4351-4362 (2002).

Shridhar, R., et al., "Cystatin AM Suppresses The Malignant Phenotype of Human MDS-MB-435S Cells", *Oncogene*, 23: 2206-2215 (2004).

Stetler-Stevenson, W.G., "Matrix Metalloproteinases In Angiogenesis: A Moving Target For Therapeutic Intervention", *The Journal of Clinical Investigation*, 103(9): 1237-1241 (1999).

Sutherland, K.D., et al., "Differential Hypermethylation Of SOCS Genes In Ovarian And Breast Carcinomas", *Oncogene*, 23: 7726-7733 (2004).

Tabuchi, Y., et al., "Resistance To Paclitaxel Therapy Is Related With Bcl-2 Expression Through An Estrogen Receptor Mediated Pathway In Breast Cancer", *International Journal of Oncology*, 34: 313-319 (2009).

Vaidyanathan, G., et al., "The Ras-Related Protein AGS1/RASD1 Suppresses Cell Growth", *Oncogene*, 23: 5858-5863 (2004).

Wehbe-Janek, H., et al., "Cordycepin/Hydroxyurea Synergy Allows Low Dosage Efficacy Of Cordycepin In MOLT-4 Leukemia Cells", *Anticancer Research*, 27: 3143-34146 (2007).

Xu R. S. et al., "Drug-loaded biodegradable microspheres for image-guided combinatory epigenetic therapy in cells", Journal of Biomedical Optics (JBO Letters), published online Feb. 16, 2011, vol. 16, No. 2, pp. 020507-1-020507-3.

Mirza S. et at., Demethylating agent 5-aza-2-deoxycytidine enhances susceptibility of breast cancer cells to anticancer agents, Mol. Cell Biochem., 2010, vol. 342, pp. 101-109.

Kabanov A.V et al., Nanogels as Pharmaceutical Carriers: Finite Networks of Infinite Capabilities, Angew Chem. Int. Ed. Engl., 2009, vol. 48, No. 30, pp. 5418-5429.

Reddy, M.K., et al., "Inhibition of Apoptosis Through Localized Delivery of Rapamycin-Loaded Nanoparticles Prevented Neointimal Hyperplasia and Reendothelialized Injured Artery," Circ Cardiovasc Intervent. 1:209-216 (2008).

Lujambio, A. et al., "A microRNA DNA methylation signature for human cancer metastasis," PNAS, vol. 105; No. 36; 13556-13561 (2008).

Xiao, W.-H. et al., "Effect of 5-Aza-2'-deoxycytidine on immune-associates proteins in exosomes from hepatoma," World of Gastroenterology, vol. 16; No. 19; 2371-2377 (2010).

Xu, J.S. et al., "Synthesizing and binding dual-mode poly (lactic-co-glycolic acid) (PLGA) nanobubbles for cancer targeting and imaging," Biomaterials, vol. 31; 1716-1722 (2010).

Zuo, T. et al., "Epigenetic Silencing Mediated through Activated PI3K/AKT Signaling in Breast Cancer," Cancer Research, vol. 71; No. 5; 1752-1762 (2011).

Notice of Allowance for U.S. Appl. No. 15/011,467, dated Aug. 10, 2018.

3 a 3 b

5a

5b 7 c 7 d

8a

8b

Figure 8c
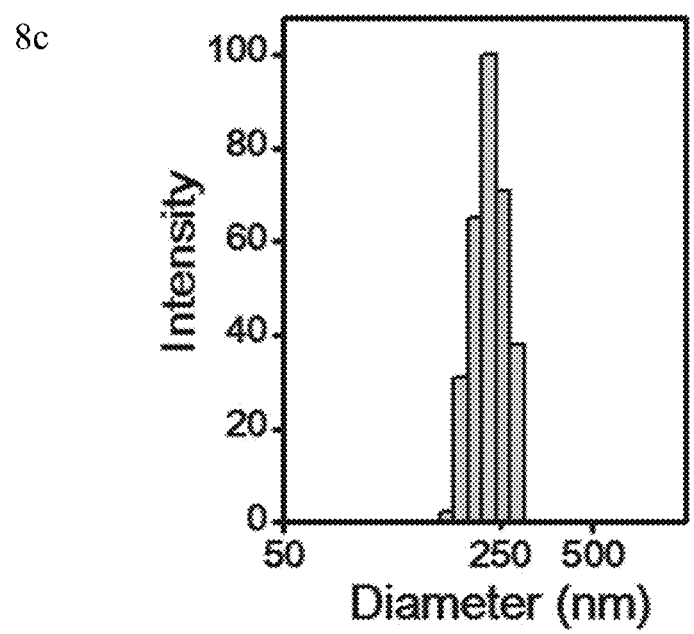
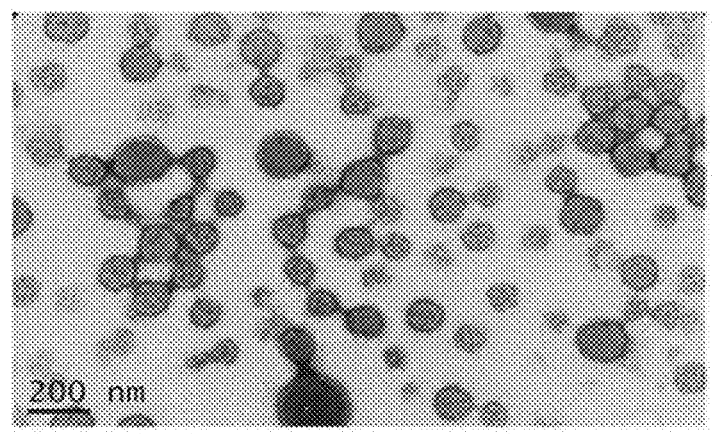

Physical characterization of PNIPAM-VP-PEGMA nanogels

| Nanogels | | % Loading efficiency | % Loading content | DLS Diameter (nm) | PI | TEM | Zeta (mV) |
|---|---|---|---|---|---|---|---|
| NG-70 | Without DAC | - | - | 233 | 0.06 | 75±8 | -25±4.0 |
| | With DAC | 85 | 6.8 | 244 | 0.11 | 85±9 | -19±1.0 |
| NG-80 | Without DAC | - | - | 129 | 0.05 | 58±5 | -20±1.0 |
| | With DAC | 73 | 6 | 126 | 0.01 | 61±6 | -20±0.1 |
| NG-85 | Without DAC | - | - | 132 | 0.05 | 65±6 | -17±0.8 |
| | With DAC | 70 | 6 | 134 | 0.02 | 66±5 | -17±2.0 |
| NG-100 | Without DAC | - | - | 99 | 0.08 | 53±2 | -14±0.3 |
| | With DAC | 85 | 7 | 116 | 0.08 | 61±2 | -16±0.3 |

Efficacy of DAC solution vs DAC nanogel in THP1 drug resistant leukemia cell line

NG-100 a) Hydrodynamic particle size distribution of DAC loaded PNIPAM-VP-PEGMA nanogel in water measured by using dynamic laser light scattering.

b) Transmission electron micrograph of DAC loaded PNIPAM-VP-PEGMS nanogel.

Cytocompatibility of nanogels (without drug) in vascular smooth muscle cells. Nanogels are not toxic to cells.

Figure 21

Nanogel composition

| S.No | Nanogel code | NIPAM (mg) | VP (mg) | PEG-MA (mg) |
|---|---|---|---|---|
| 1 | NG-70 | 700 | 200 | 100 |
| 2 | NG-80 | 800 | 100 | 100 |
| 3 | NG-85 | 850 | 100 | 50 |
| 4 | NG 100 | 1000 | - | - |

Particle size and zeta potential of decitabine loaded nanogel

| Nanogels | | % Loading efficiency | % Loading | Hydrodynamic Diameter (nm) | PI | TEM | Zeta (mV) |
|---|---|---|---|---|---|---|---|
| NG-70 | Void-Nanogel | - | - | 233 | 0.06 | 75±8 | -25±4.0 |
| | Drug-loaded | 85 | 6.8 | 244 | 0.11 | 85±9 | -19±1.0 |
| NG-80 | Void-Nanogel | - | - | 129 | 0.05 | 59±5 | -20±1.0 |
| | Drug-loaded | 73 | 6 | 126 | 0.01 | 61±6 | -20±0.1 |
| NG-85 | Void-Nanogel | - | - | 132 | 0.05 | 65±6 | -17±0.8 |
| | Drug-loaded | 70 | 6 | 134 | 0.02 | 66±5 | -17±2.0 |
| NG-100 | Void-Nanogel | - | - | 99 | 0.08 | 53±2 | -14 ± 0.3 |
| | Drug-loaded | 76 | 6.1 | 116 | 0.06 | 61±2 | -16 ± 0.3 |

Particle size and zeta potential of SAHA loaded nanogel

| Nanogels | | % Loading efficiency | % Loading | Hydrodynamic Diameter (nm) | PI | TEM | Zeta (mV) |
|---|---|---|---|---|---|---|---|
| NG-70 | Void-Nanogel | - | - | 233 | 0.06 | 75±8 | -25±4.0 |
| | Drug-loaded | 48.4 | 4.84 | 228 | 0.2 | - | -10±1.0 |
| NG-80 | Void-Nanogel | - | - | 129 | 0.05 | 59±5 | -20±1.0 |

TEM: Transmission Electron Microscopy
PI: Polydispersity Index
mV=Millivolt
nm: Nanometer

NANOGEL-MEDIATED DRUG DELIVERY

RELATED APPLICATIONS

This application is a divisional of U.S. application Ser. No. 15/011,467, filed Jan. 29, 2016, which is a continuation of U.S. application Ser. No. 14/046,343, filed Oct. 4, 2013, now abandoned, which claims the benefit of U.S. Provisional Application No. 61/710,499, filed on Oct. 5, 2012. The entire teachings of the above applications are incorporated herein by reference.

GOVERNMENT SUPPORT

This invention was made with government support under RO1CA149359-01 from the National Cancer Institutes of the National Institutes of Health. The government has certain rights in the invention.

BACKGROUND OF THE INVENTION

Epigenetic mechanisms such as DNA hypermethylation lead to silencing of tumor suppressor genes and cell cycle regulator genes that influences the efficacy of many anticancer drugs. In addition, cancer cells develop drug resistance. Aberrant DNA methylation is an epigenetic mechanism that leads to silencing of many tumor suppressor genes involved in key DNA damage-response pathways, such as cell cycle control, apoptosis signaling, and DNA repair. This epigenetic silencing influences tumorigenesis, tumor response to drug therapy, and is also the main cause of acquired drug resistance. Drug resistance constitutes lack of response to many chemically and mechanistically unrelated anticancer agents by cancer cells. It is one of the main causes for failure of chemotherapy and can lead to recurrence of the disease or even death. Clinical administration of anticancer drugs can also lead to epigenetic changes in cancer cells such as DNA hypermethylation making them resistant to drug treatment (Nyce, J W, Mutat Res (1997) 386:153-161). Such drug-induced DNA hypermethylation can further create resistance by silencing genes whose products are required by anticancer drugs to execute cytotoxicity.

A need exists to overcome such mechanisms in order to improve cancer treatments.

SUMMARY OF THE INVENTION

Described herein is the determination of the efficacy of demethylating agent, 5-aza-2'-deoxycytidine or decitabine, which acts as an inhibitor of DNA methyl transferase (DNMT-1), on sensitization of drug resistant breast cancer cells to the effect of doxorubicin. The results herein demonstrate that the pretreatment of decitabine significantly enhances the efficacy of doxorubicin. The mechanism of sensitization of resistance was determined to be due to a combined mechanism of upregulated p21WAF1/CIP1 expression and induced G2/M arrest. Induction of p21WAF1/CIP1 correlated very well with observed depletion of DNMT1. Shown herein is that the synergistic effect of the sequential treatment was further enhanced with drugs encapsulated in biodegradable nanogels, primarily because of enhanced stability of decitabine. Nanogel-mediated drug delivery (e.g., in sequential order) could prove to be effective cancer therapy, particularly to overcome the issue of drug resistance.

Accordingly, in one aspect, provided herein are methods of inhibiting proliferation of one or more tumor cells comprising contacting the one or more tumor cells with a composition comprising one or more epigenetic drugs that inhibit one or more epigenetic mechanisms of the tumor cells, wherein the one or more epigenetic drugs are encapsulated in a nanogel. The method can further comprise contacting the cells with one or more chemotherapeutic agents. In a particular aspect, the one or more chemotherapeutic agents are encapsulated in a nanogel.

In another aspect, the invention is directed to methods of treating a tumor, metastasis of a tumor or a combination thereof in an individual in need thereof comprising administering a therapeutically effective amount of a composition comprising one or more epigenetic drugs that alter (e.g., inhibit) one or more epigenetic mechanisms of the tumor cells, wherein the one or more epigenetic drugs are encapsulated in a nanogel, to the individual. The method can further comprise administering one or more chemotherapeutic agents. In a particular aspect, the one or more chemotherapeutic agents are encapsulated in a nanogel.

Also provided herein are the compositions which comprise one or more epigenetic drugs that alter one or more epigenetic mechanisms of a tumor cell, wherein the one or more epigenetic drugs are encapsulated in a nanogel. In particular aspects, the composition can further comprise one or more chemotherapeutic drugs encapsulated in a nanogel. The one or more epigenetic drugs and the one or more chemotherapeutic drugs can be encapsulated in the same nanogel. In a particular aspect, the one or more chemotherapeutic drug is loaded in the nanogel's core and the one or more epigenetic drugs are loaded in the nanogel's corona.

In another aspect, the invention is directed to a method of sequentially delivering one or more epigenetic drugs that alter one or more epigenetic mechanisms of a tumor cell and one or more chemotherapeutic drugs to an individual that has a tumor, comprising administering a therapeutically effective amount of a nanogel to the individual, wherein the one or more chemotherapeutic drug is loaded in the nanogel's core and the one or more epigenetic drugs are loaded in the nanogel's corona.

BRIEF DESCRIPTION OF THE DRAWINGS

FIGS. 8a-8e: 8a) Time course uptake of doxorubicin (dox) in drug resistant breast cancer cells shows increased drug uptake in decitabine (DAC) pre-treated cells (grey bars) than drug alone treated cells (black bars). Data as a mean±SEM (n=4). ** $p<0.0005$, * $p<0.005$ dox vs. DAC+ dox. 8b) Western blot analysis of cell lysates of resistant cells shows 45% decrease in P-gp protein expression in cells treated with DAC at day 1 when compared with untreated cells. P-gp expression returned to normal levels at day 3. 8c) Polymer nanogel size measurement by Dynamic Light Scattering and Transmission electron microscopy study shows the particle size to be 233 nm and 75±8 nm respectively. 8d) Comparison of cytotoxicity of DAC nanogels vs. DAC in solution in drug resistant breast cancer cells. DAC nanogels shows better antiproliferative activity 12 day post drug addition than DAC in solution.

8e) Mean tumor size in MCF7/Adr orthotopic tumor induced mice treated with control nanogels, DAC in solution and DAC nanogel. There was a significant difference in the tumor size of mice treated with the control nanogel/DAC in solution vs. the drug loaded nanogels (p=0.0003), whereas the two controls were not different. Data were expressed as mean±SEM (n 3 to 6). Variances in tumor growth were determined using one-way ANOVA test followed by Tukey test using GraphPad Prism version 4.0 for Windows ($p<0.05$).

Figures 9A, 9B:
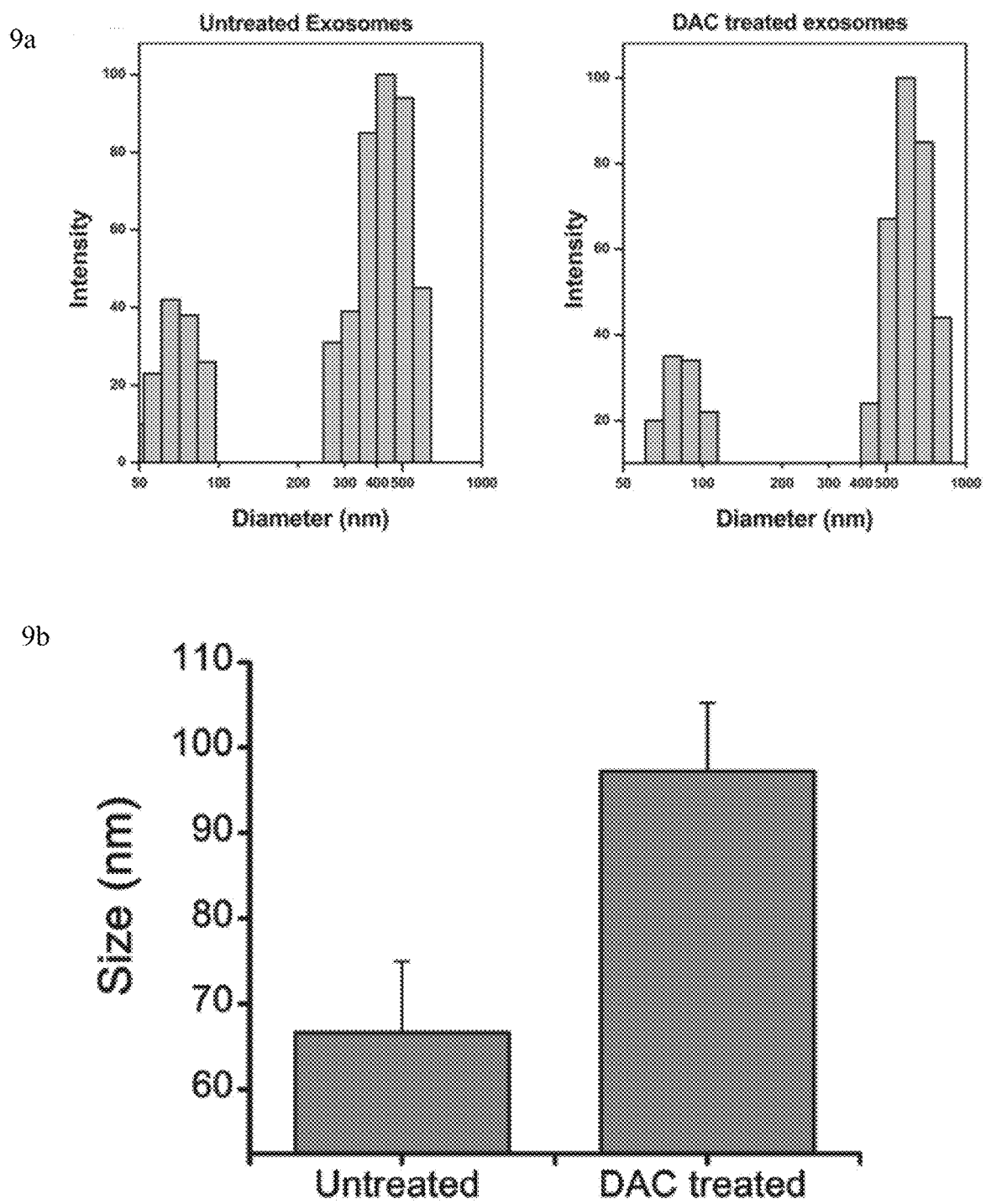
Figure 9C:
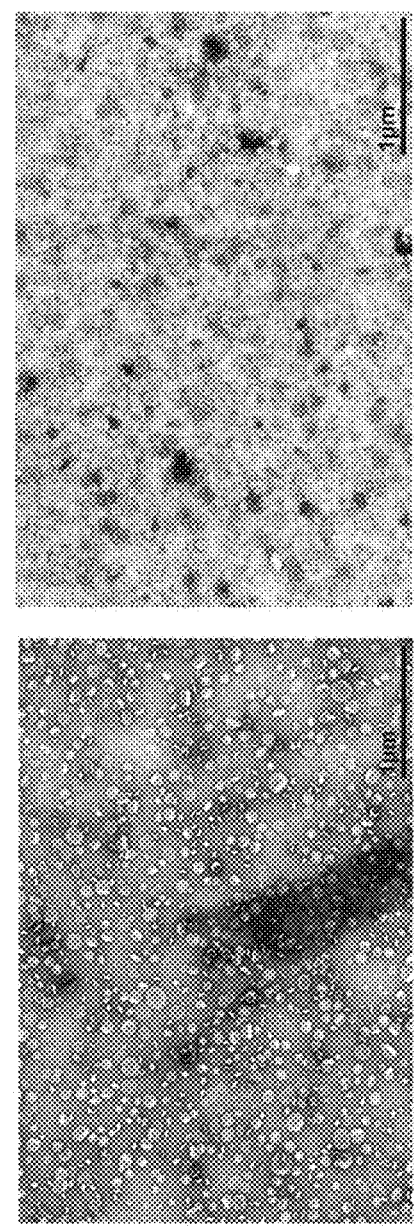

FIGS. 9a-9c: 9a) Hydrodynamic diameter of exosomes isolated from untreated and DAC treated metastatic breast (MDA-MB 231) cells. 9b) Size measurement by transmission electron microscopy. From TEM images size was measured using Image J software. 9c) Transmission electron micrograph of exosomes isolated from MDA-MB 231 cells treated with and without DAC.

Figure 10:
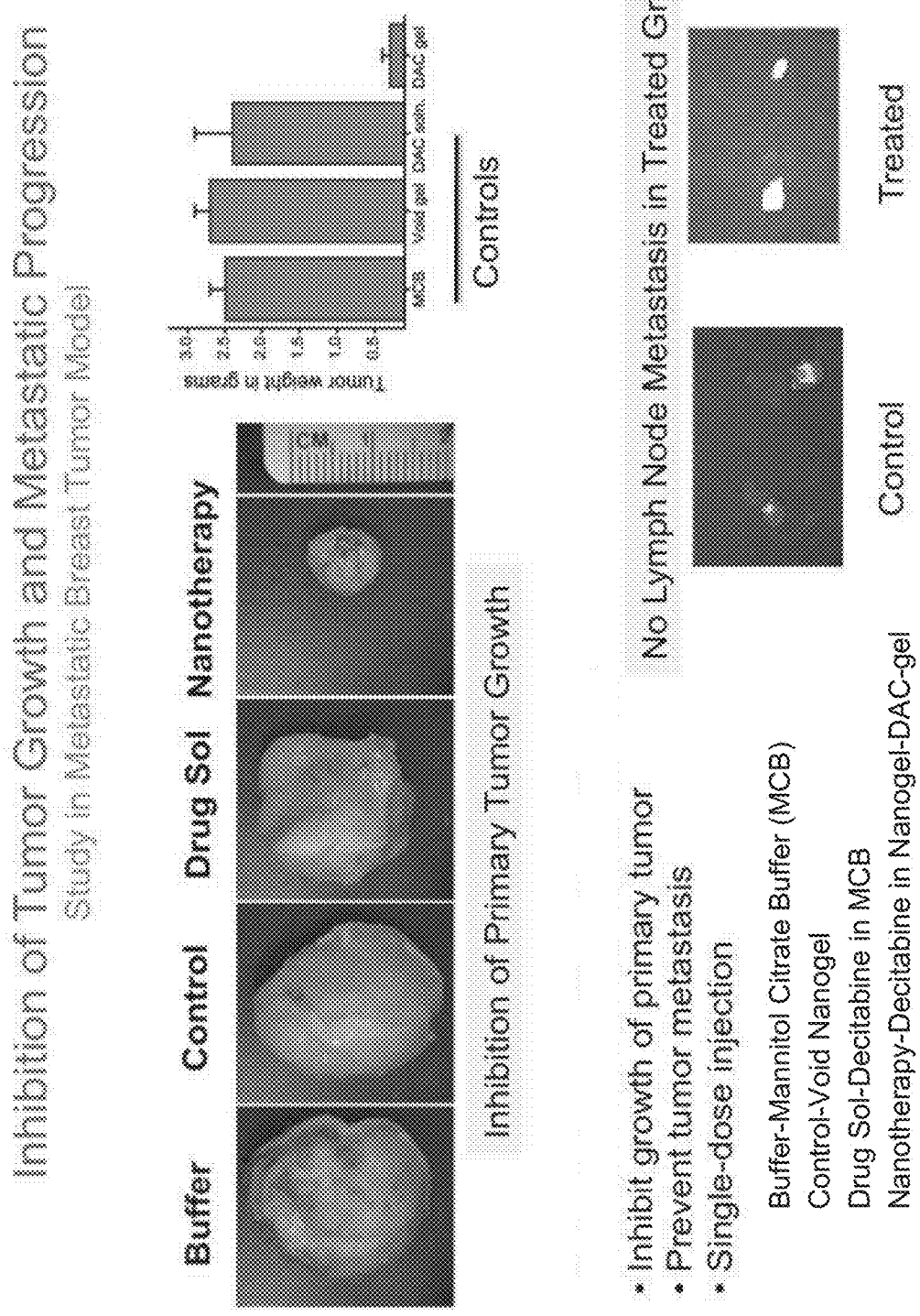

FIG. 10: Inhibition of Tumor Growth and Metastatic Progression Study in Metastatic Breast Tumor Model; Inhibited growth of primary tumor, Prevented tumor metastasis, single-dose injection.

FIG. 11: Physical characterization of PNIPAM-VP-PEGMA nanogels.

Figure 12:
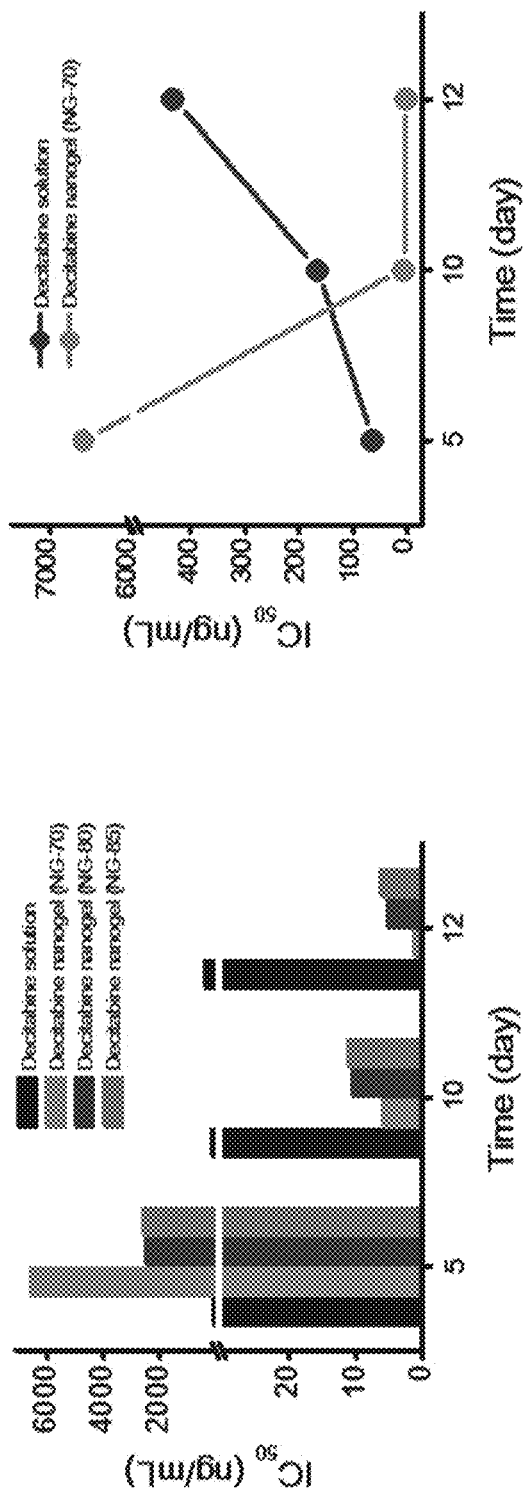

FIG. 12: Efficacy of PNIPAM-VP-PEGMA nanogels in drug resistant breast cancer cells (MCF-7/Adr).

Figure 13:
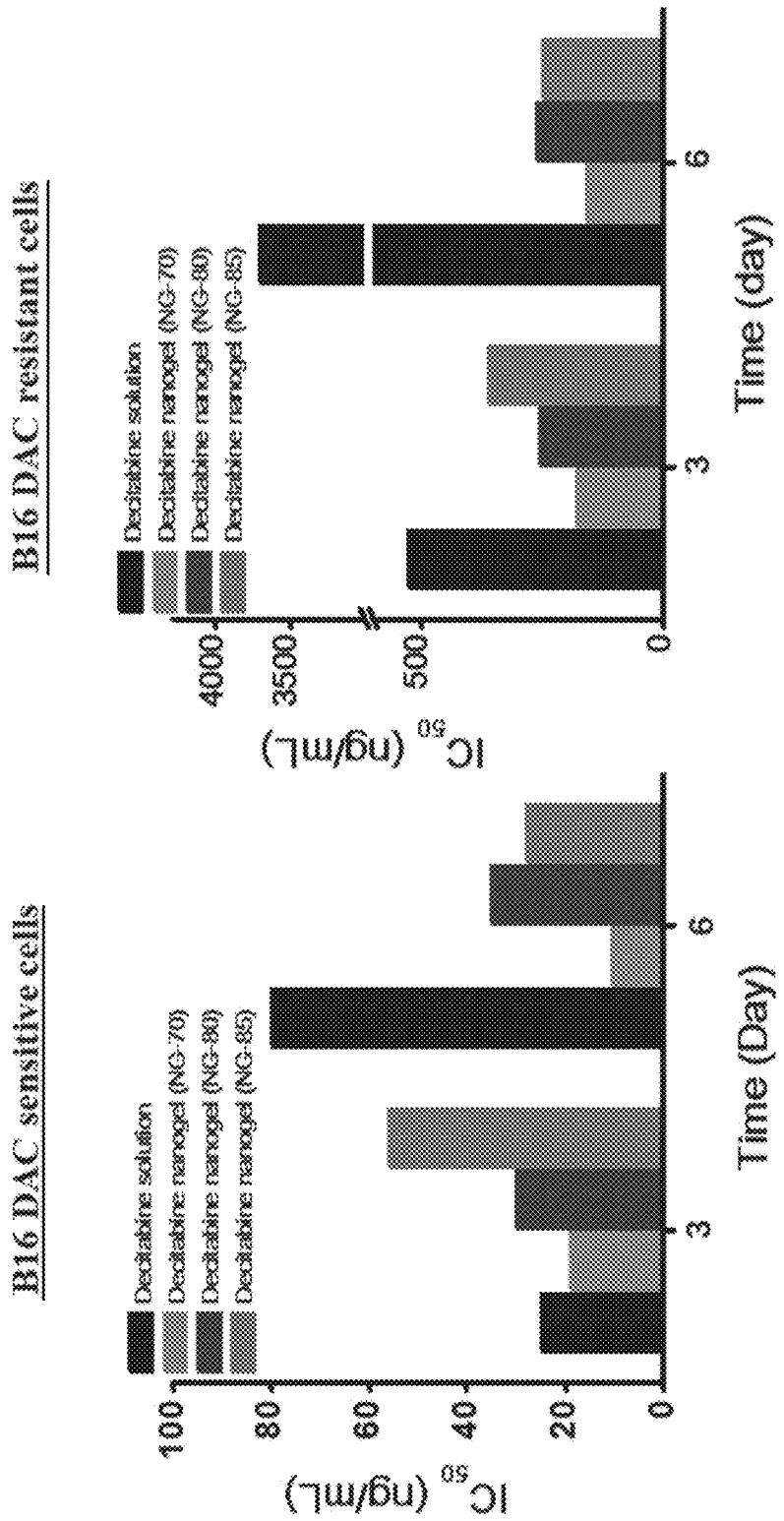

FIG. 13: Comparison of the $IC_{50}$ value of decitabine (deci) solution vs nanogels in B26 deci sensitive melanoma cells and B16 deci resistant melanoma cells.

Figure 14:
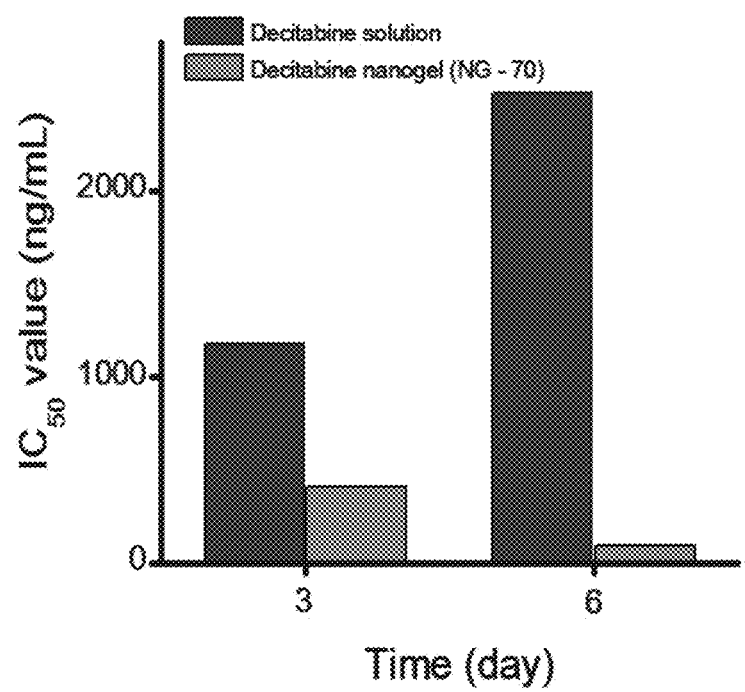

FIG. 14: Efficacy of DAC solution vs DAC nanogel in THP1 drug resistant leukemia cell line.

Figure 15A:
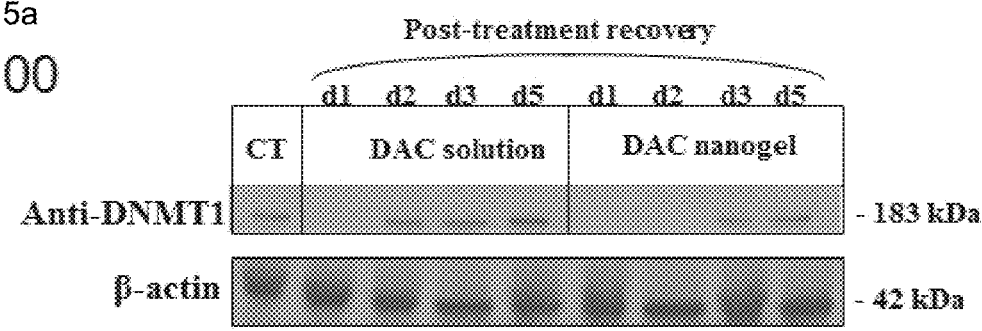
Figure 15B:
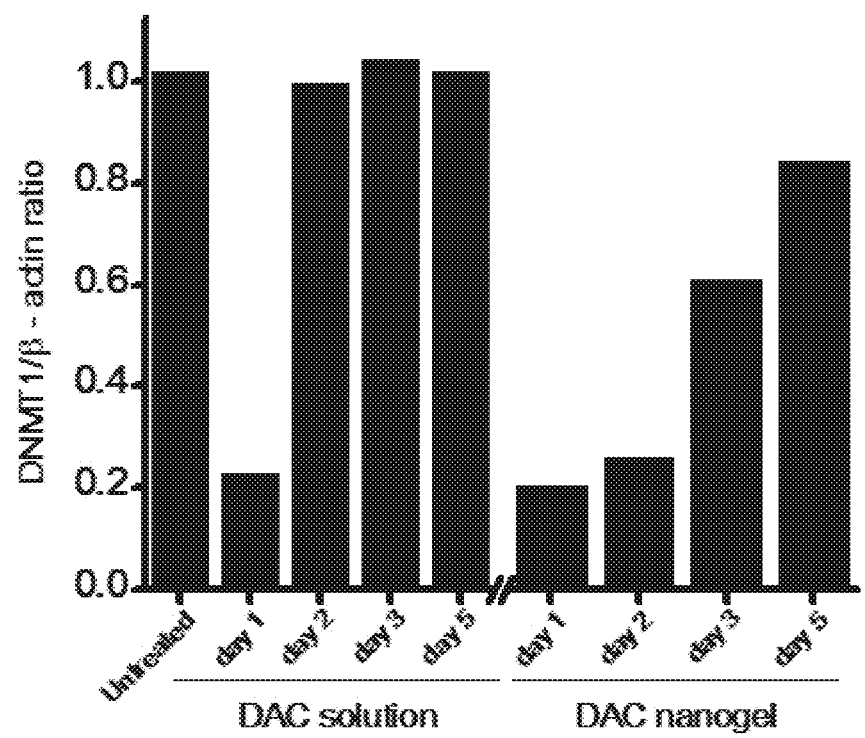

FIG. 15a-b: 15a) MCF-7/Adr cells treated with DAC nanogel or with DAC solution for 1-5 days; 15b) DNMT1/β-actin ratio versus decitabine (DAC) solution and DAC nanogel in MCF-7/Adr cells.

Figure 16A:
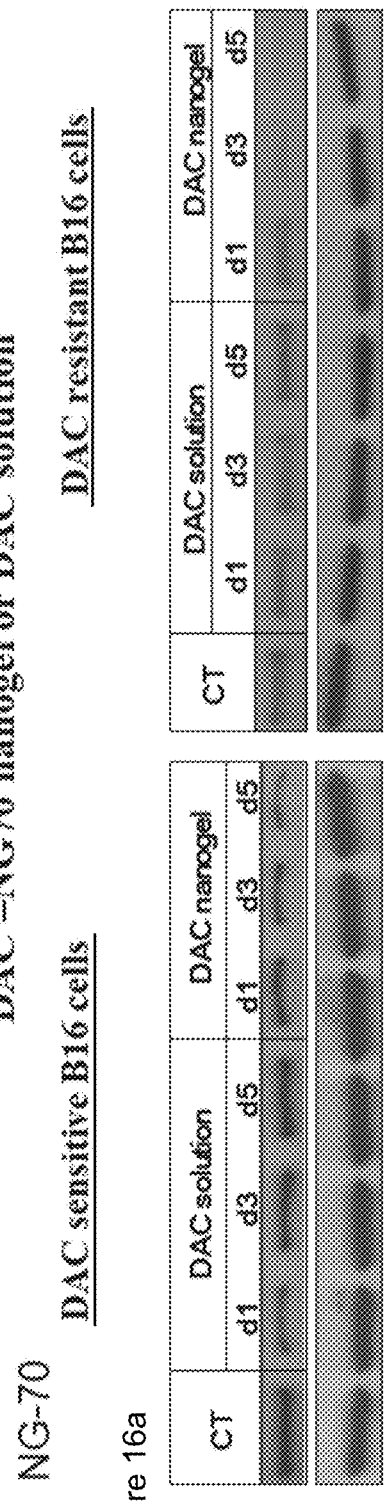
Figure 16B:
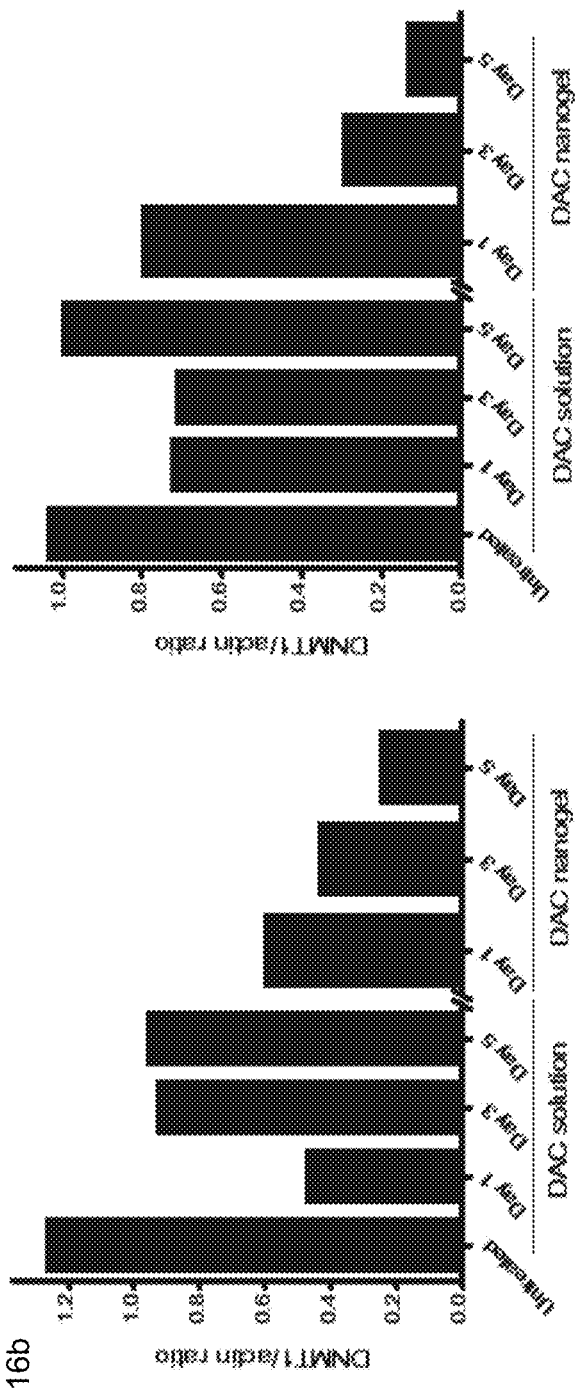

FIG. 16a-b: 16a) B16 and B16 resistant melanoma cells treated with DAC-NG70 nanogel or DAC solution for 1-5 days; 16b) DNMT1 levels of B16 and B16 resistant melanoma cells treated with DAC-NG70 nanogel of DAC solution.

Figures 17A, 17B:
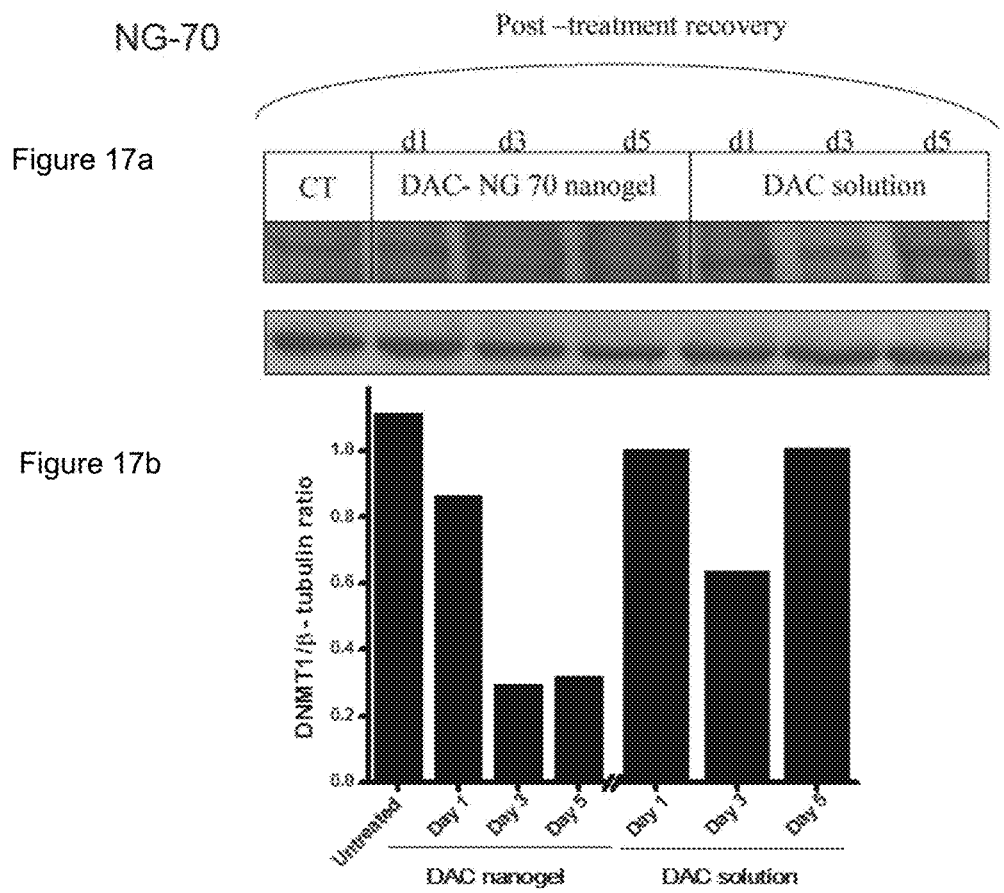

FIG. 17a-b: 17a) THP1 cells treated with DAC-NG 70 nanogel or DAC solution for 1-5 days; 17b) DNMT1 levels of THP1 (DAC resistant cells) leukemia cells treated with DAC NG70 nanogel or DAC solution.

Figure 18:
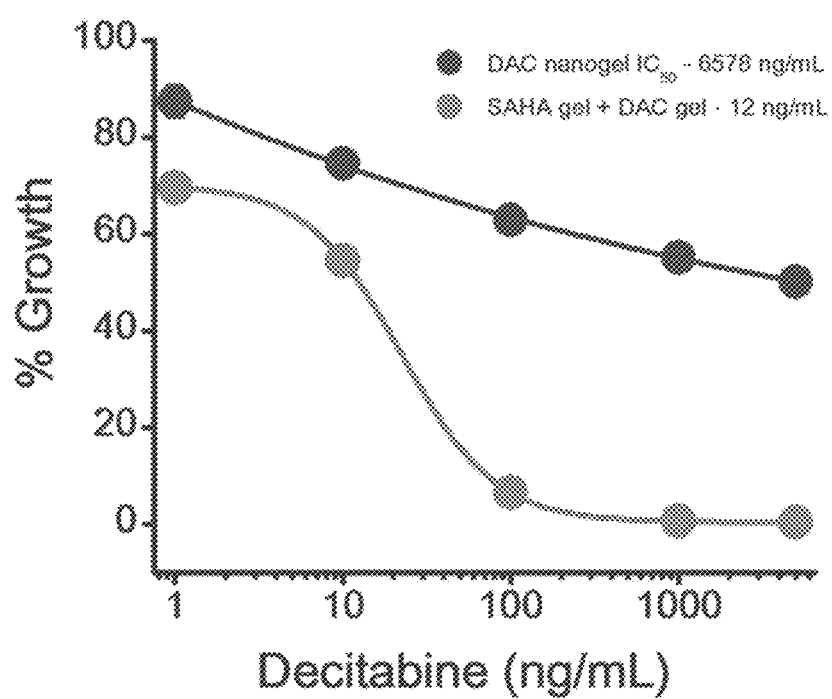

FIG. 18: Decitabine versus % growth showing the combination of SAHA-nanogel and DAC-nanogel show highly synergistic effect than DAC-Nanogel or SAHA-nanogel alone.

Figure 19A:
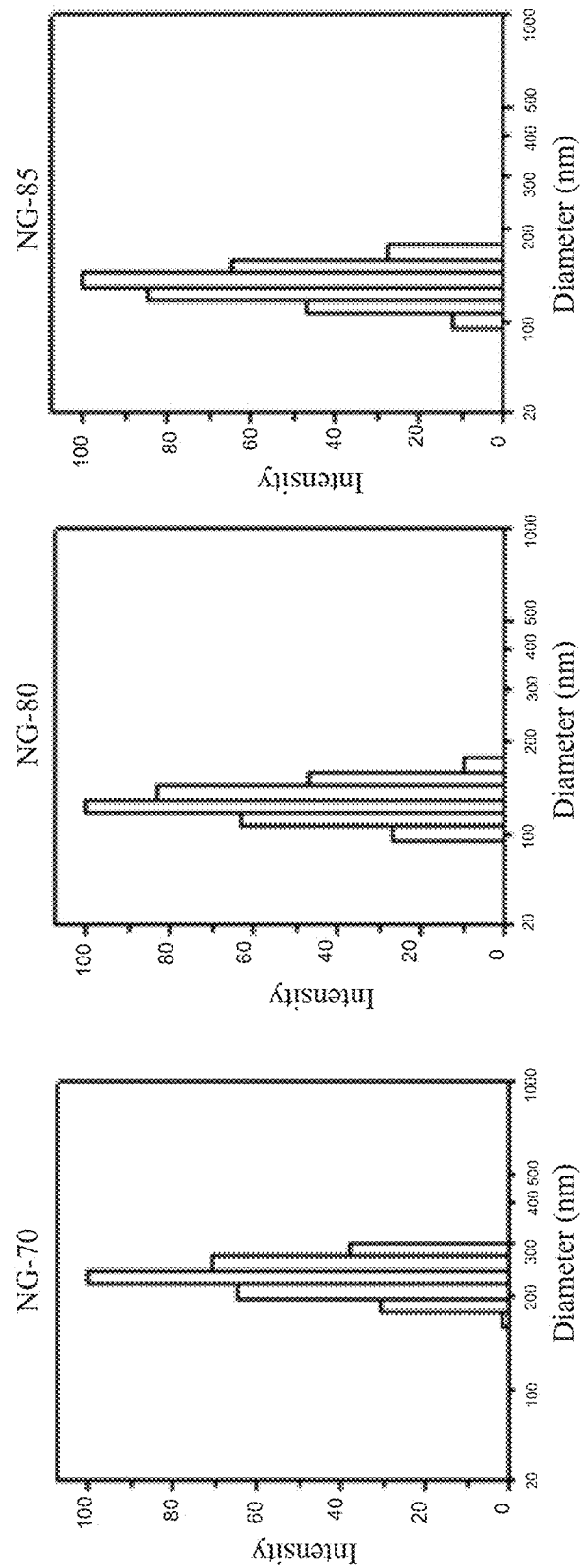
Figure 19B:
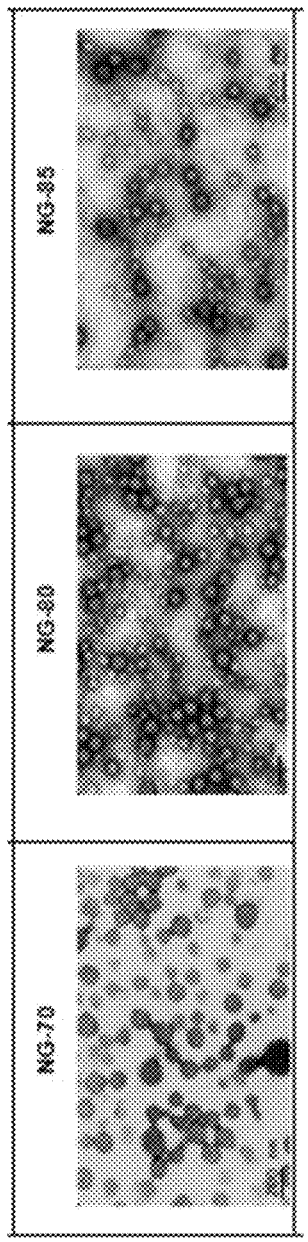
Figure 19C:
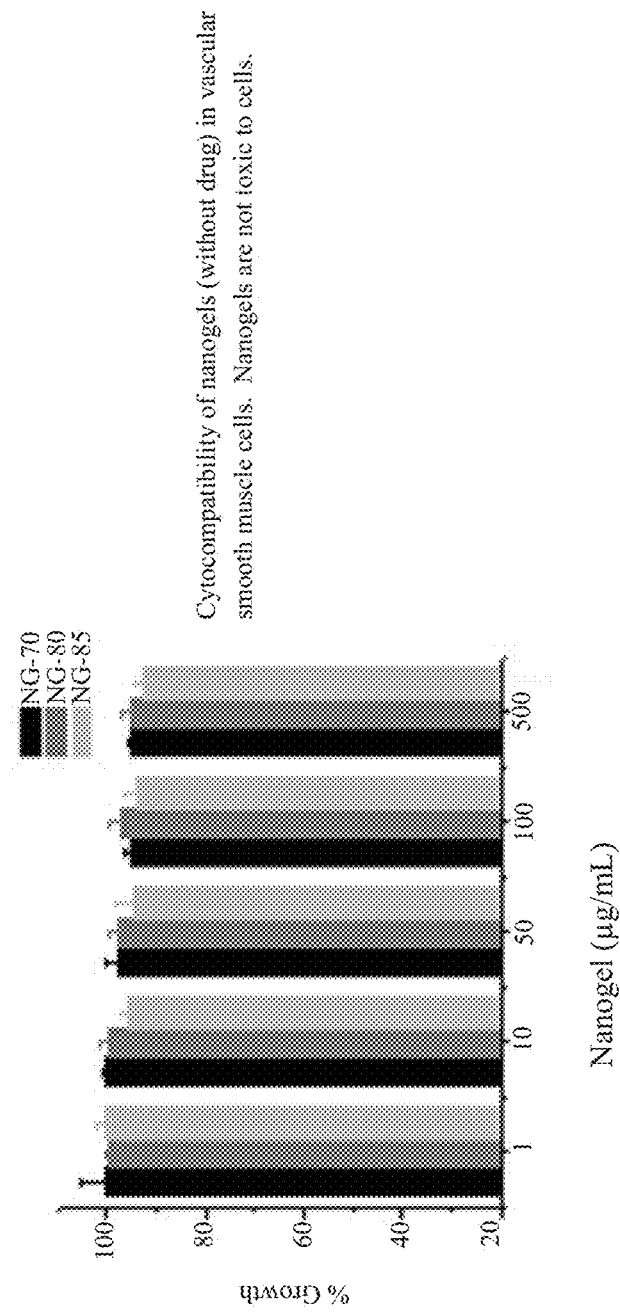

FIG. 19a-c: Physical characterization of DAC loaded PNIPAM-VP-PEGMA nanogels-Size measurement by 19a) Dynamic laser light scattering and 19b) Transmission electron micrograph. 19c) Cytocompatibility of nanogels (without drug) in vascular smooth muscle cells.

Figure 20:
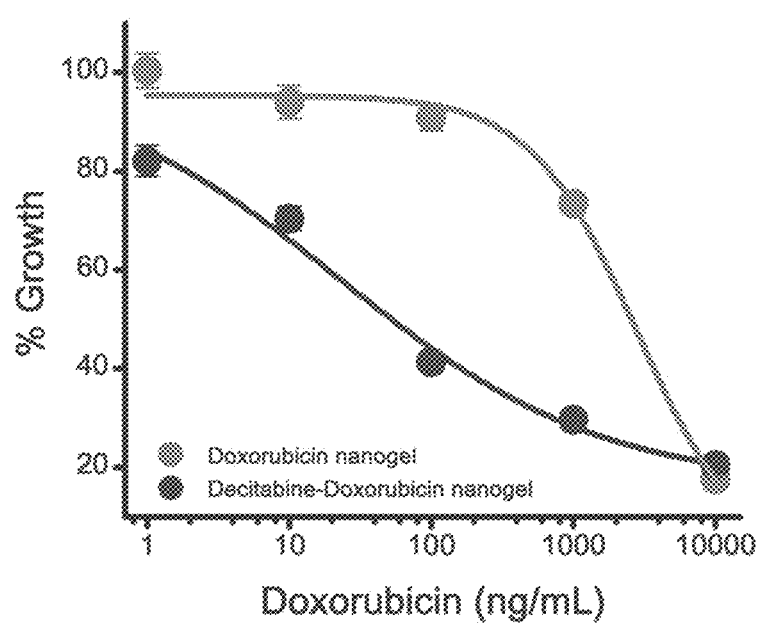

FIG. 20: Comparison of efficacy of doxorubicin loaded nanogels vs decitabine-doxorubicin loaded nanogel in multidrug resistant breast cancer cells (MCF-7/Adr).

FIG. 21: Nanogel composition, particle size and zeta potential of decitabine loaded nanogel, particle size and zeta potential of suberoylanilide hydroxamic acid (SAHA) loaded nanogel.

Figure 22:
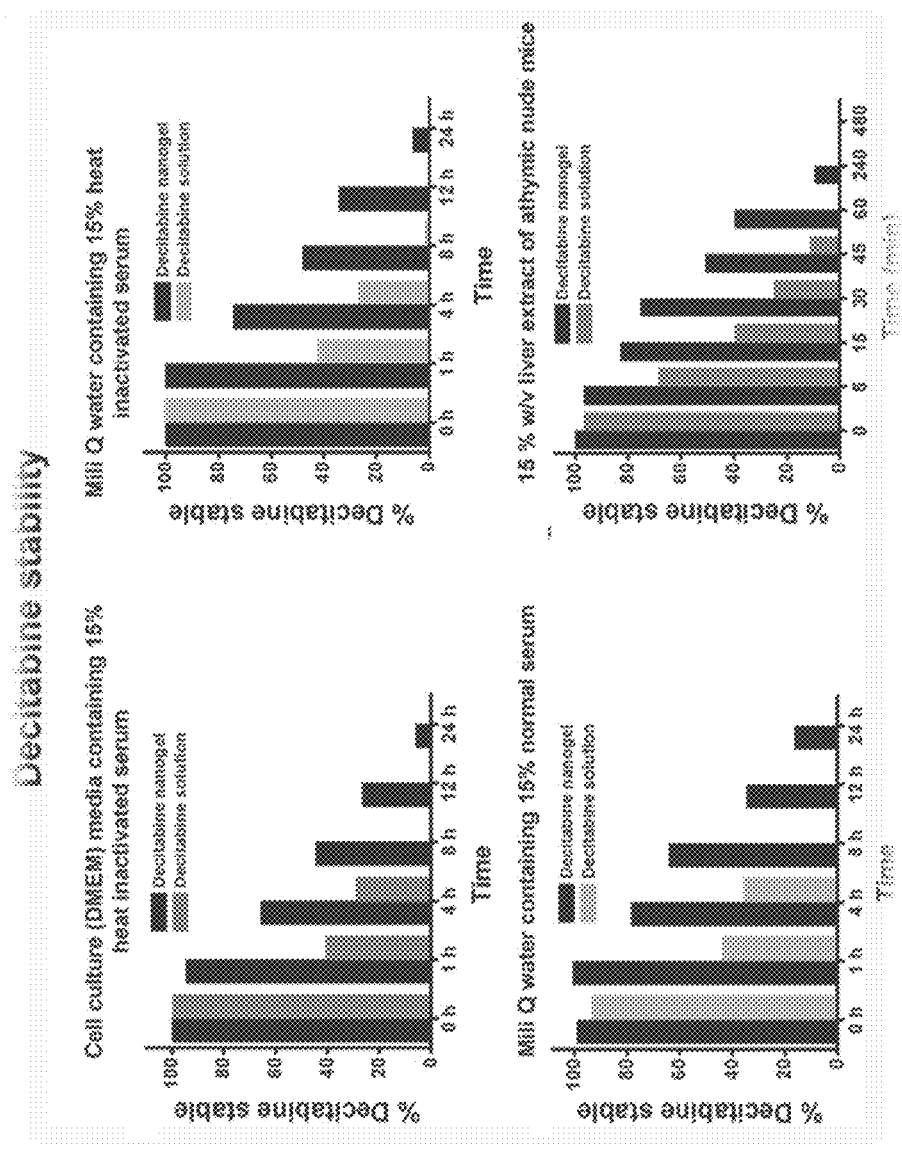

FIG. 22: Decitabine stability

DETAILED DESCRIPTION OF THE INVENTION

A description of example embodiments of the invention follows.

Shown herein is that treating drug resistant cells with demethylating agent could reverse epigenetic gene silencing and sensitize them for chemotherapy. Four nucleoside deoxycitidine analogs which are demethylating agents, have been clinically tested; 5-azacytidine, 5-aza-2-deoxycitidine (decitabine; DAC), 1-β-D-arabinofuranosyl-5-azacytosine and dihydro-5-azacytidine; of these first two have been shown to have antitumor activity. The last two were no longer under study due to lack of efficacy (Goffin J and Eisenhauer E (2002) Ann Oncol, 13:1699-1716]. Finally in a rat model 5-azacytidine was shown to be carcinogenic, while DAC has not (Carr et al. (1988) 57:395-402). Based on these findings, DAC was selected as a demethylating agent to sensitize the cancer cells. However, DAC also has its own limitations. On parenteral administration DAC is metabolized in the liver by cytidine deaminase to form a non cytotoxic 5-aza-2-deoxyuridine. DAC has a very high clearance and have very short half-life (10-35 min) in humans, and the effect of DAC in vivo has been reported as transient (Brown and Plumb (2004) Expert Rev Anticancer Ther, 4:501-510; Mund et al. (2005) 65:7086-7090). Further, clinical administration of drugs in vivo needs to overcome the various barriers to reach target tissue and also therapeutic doses needed to be maintained until the tumor has been completely regressed, and the drug doses should not be toxic to normal cells. As shown herein, encapsulation of DAC in PNIPAM (poly-N-isopropylacrylamide) polymer nanogel increased its stability, and was effective alone or in combination with other anticancer drugs (e.g., doxorubicin) in overcoming drug resistance in cancer cells.

Accordingly, in one aspect, provided herein are methods of inhibiting proliferation of one or more tumor cells comprising contacting the one or more tumor cells with a composition comprising one or more epigenetic drugs that inhibit one or more epigenetic mechanisms of the tumor cells, wherein the one or more epigenetic drugs are encapsulated in a nanogel.

In another aspect, the invention is directed to methods of treating a tumor, metastasis of a tumor or a combination thereof in an individual in need thereof comprising administering a therapeutically effective amount of a composition comprising one or more epigenetic drugs that alter (e.g., inhibit) one or more epigenetic mechanisms of the tumor cells, wherein the one or more epigenetic drugs are encapsulated in a nanogel, to the individual.

As used herein an epigenetic mechanism refer to epigenetic events that are associated with one or more steps of tumor development and progression (Mani and Herceg (2010) Advances in Genetics, 70:327-340; Yoo and Jones (2006) Nature Reviews, 5:37-50). Examples of epigenetic mechanisms include DNA methylation, histone modification, expression of non-coding RNA or a combination thereof.

Examples of epigenetic drugs that alter epigenetic mechanisms include a DNA-methylation inhibitor (e.g., DNA methyltransferase inhibitor), a histone deacetylase inhibitor, a microRNA inhibitor, a long non-coding RNA inhibitor or a combination thereof. Classes of DNA methylation inhibitors include nucleoside analogues and non-nucleoside analogues; and classes of histone deacetylase inhibitors include short-chain fatty acids, hydroxyamic acids, cyclic tetrapeptides and benzamides. Specific examples of epigenetic drugs include 5-azacytidine, 5-Aza-2'-deoxycytidine (decitabine (DAC)), 5-Fluoro-2'-deoxycytidine, 5,6-Dihydro-5-azacytidine, Zeblarine, suberoylanilide hydroxamic acid (SAHA), butyrate, valproic acid, m-carboxy cinnamic acid bishydroxamic acid (CBHA), oxamflatin, PDX 101, pyroxamide, scriptaid, trichostatin A (TSA), LBH589, NVP-LAQ824, hydralazine, procainamide, ECGC, psammaplin A, MC98, RG108, apicidin, depsipeptide (FK-228, FR901228), TPX-HA analogue (CHAP), trapoxin, CL-994 (N-acetyl dinaline), MS-275 or a combination thereof.

As described herein, in the methods of the invention the tumor cells can be further contacted with one or more chemotherapeutic drugs. In a particular aspect, the one or more chemotherapeutic drugs are encapsulated in a nanogel. In yet another aspect, the one or more chemotherapeutic drugs are encapsulated in the nanogel that encapsulates the one or more epigenetic drugs or the one or more chemotherapeutic drugs are encapsulated in a separate nanogel.

As shown herein, in a particular aspect, nanogels are first loaded with the one or more chemotherapeutic agents (e.g., doxorubicin) and then with one or more epigenetic drugs (e.g., decitabine) to achieve sequential delivery. This aspect of the invention has been illustrated using decitabine and doxorubicin. For example, an epigenetic drug such as doxorubicin is first converted into the base form; it can be dissolved in ethanol and added drop-wise to an aqueous dispersion of nanogel. The drug partitions into the core of nanogel because of its hydrophobic nature. Excess doxorubicin can be removed e.g., using dialysis. The Doxorubicin-loaded nanogel is then loaded with a chemotherapeutic agent such as decitabine which partition into the corona of nanogels. Decitabine first exerts its effect after phosphorylation and direct incorporation into DNA by inhibiting DNA methyltransferase (DNMT, an enzyme that methylates DNA), causing hypomethylation of DNA.

In specific aspect, the tumor cells are contacted with the one or more epigenetic drugs and the one or more chemotherapeutic drugs simultaneously or sequentially. For example, the tumor cells can be first contacted with the one or more epigenetic drugs and then contacted with the one or more chemotherapeutic drugs. For sequential administration of the one or more epigenetic drugs and the one or more chemotherapeutic drugs, the timing of the contact of each will vary depending on a variety of factors (e.g., the tumor being treated, the condition of the individual, etc.). In a particular aspect, the one or more chemotherapeutic drugs is contacted with the tumor cell for about 1 hours, 10 hours, 24 hours, 48 hours, 72 hours, 96 hours, 120 hours, 148 hours, etc. after the cancer cells are contacted with the one or more epigenetic drugs.

As will be appreciated by those of skill in the art, a variety of chemotherapeutic drugs can be used in the methods of the invention. Examples of chemotherapeutic drugs are doxorubicin, daunorubicin, epirubicin, topotecan, etoposide, cisplatin, carboplatin, oxalipatin, 5-fluorouracil, gemcitabine, cytosine arabinoside, genistein, adozelesin, docetaxel or a combination thereof.

The methods described herein can be used to inhibit the proliferation of, treat a variety of tumors and/or tumor metastasis. As used herein, tumor cells include cancerous and non-cancerous cells (e.g., supporting cells of the tumor) of the tumor (e.g., stroma cells; inflammatory cells; blood cells). Although some tumors (e.g., leukemias, ascites tumors) grow as cell suspensions, most tumors grow as solid masses of tissue. Typically, solid tumors comprise the parenchyma (neoplastic cells) and the stroma that the neoplastic cells induce and in which they are dispersed. In many tumors, including those of epithelial cell origin, a basal lamina separates clumps of tumor cells from stroma. However, the basal lamina is often incomplete, especially at points of tumor invasion. Tumors typically require stroma for nutritional support and for the removal of waste products. In the case of leukemias, blood plasma serves as stroma, although an additional stromal response, angiogenesis, may develop in the bone marrow. When tumors grow in body cavities, a plasma exudate (e.g., ascites) provides stroma. In solid tumors, stroma includes connective tissue, blood vessels, and, very often, inflammatory cells, all of which are interposed between the malignant cells and normal host tissues. In all tumors, stroma is largely a product of the host and is induced as the result of tumor cell-host interactions. Solid tumors, regardless of their type or cellular origin, require stroma if they are to grow beyond a minimal size of 1 to 2 mm. The supporting cells of a tumor such as stroma cells therefore, at once provides a lifeline that is necessary for tumor growth and imposes a barrier that inhibits and may regulate interchange of fluids, gases, and cells. In particular aspects, the tumor cells are stroma cells of the tumor, breast tumor cells, melanoma cells, leukemic cells, brain tumor cells, ovarian tumor cells or a combination thereof. In another aspect, the tumor cells are drug resistant tumor cells, metastatic tumor cells or a combination thereof.

As used herein, an effective dose or a therapeutically effective dose of the one or more epigenetic drugs and/or the one or more chemotherapeutic drugs is an amount sufficient to inhibit the proliferation and/or treat the tumor such as by ameliorating symptoms, preventing or delaying metastasis and/or lessening the severity of one or more effects of the tumor. The amount that will be therapeutically effective will depend on the symptoms and severity of the tumor, and can be determined by standard clinical techniques. In addition, in vitro or in vivo assays may optionally be employed to help identify optimal dosage ranges. The precise dose to be employed in the formulation will also depend on the route of administration, and the seriousness of the disease or disorder, and should be decided according to the judgment of a practitioner and each patient's circumstances. Effective doses may be extrapolated from dose-response curves derived from in vitro or animal model test systems. In a particular aspect, the tumor cells are contacted with an effective dose of the one or more chemotherapeutic drugs that is lower than the effective dose of the one or more chemotherapeutic drug when the one or more chemotherapeutic drugs are administered without the composition comprising the epigenetic agent encapsulated in the nanogel.

As used herein, a nanogel refers to a nanoparticle composed of a crosslinked hydrophilic polymer network (hydrogel). Nanogels are most often composed of synthetic polymers or biopolymers which are chemically or physically crosslinked. In a particular embodiment, the nanogels are biocompatible. In yet another embodiment, the nanogels are biodegradable. Methods of obtaining nanogels are known in the art as well as methods for obtaining nanogels that are biocompatible and/or biodegradable (see U.S. Pat. No. 7,727,554 which is incorporated herein by reference in its entirety). In one aspect, the nanogel comprises a linker that is biodegradable (e.g., wherein enzymes (e.g., physiological enzymes) can degrade the crosslinker, thereby degrading the nanogel).

As described herein, the nanogels (e.g., biodegradable nanogels) can be synthesized using polymers (e.g., Nisopropylacrylamide, N-vinyl pyrrolidone, pegylated maleic acid or a combination thereof) with a disulfide cross-linker. Nanogels formed using, for example, the above polymers are usually ~50 nm in diameter with sustained drug release properties.

In one aspect, the nanogel of the methods and composition of the invention comprises an N-alkylacrylamide. In a particular aspect, the N-alkylacrylamide is poly-N-isopropylacrylamide. The nanogel can further comprises a vinyl monomer and a polyalkylene glycol. For example, the vinyl monomer can be vinyl pyrrolidone and the polyalkylene glycol can be polyethylene glycol. The nanogel can further comprise sodium acrylate. In particular aspects, the nanogel comprises about 500 to about 1000 mg N-alkylacrylamide. In other aspect, the nanogel can comprise about 100 to about 200 mg of the vinyl polymer and about 50 to about 100 mg of the polyalkylene glycol. In yet other aspect, the nanogel comprises about 200 mg sodium acrylate.

As will be appreciated by those of skill in the art, the dimensions of the nanogel will vary and will depend upon a variety of factors such as the method used to produce the nanogel and the purpose for which the nanogel is to be used. In one aspect, the nanogel has a particle diameter of about 10 nm, 20 nm, 40 nm, 60 nm, 80 nm, 100 nm, 120 nm, 140 nm, 160 nm, 180 nm, 200 nm, 220 nm, 240 nm, 260 nm, 280 nm, 300 nm, 320 nm, 340 nm, 360 nm, 380 nm, 400 nm, 420 nm, 440 nm, 460 nm, 480 nm, 500 nm, 520 nm, 540 nm, 560 nm, 580 nm, 600 nm, 620 nm, 640 nm, 660 nm, 680 nm, 700 nm, 720 nm, 740 nm, 760 nm, 780 nm, 800 nm, 820 nm, 840 nm, 860 nm, 880 nm, 900 nm, 920 nm, 940 nm, 960 nm, 980 nm or about 1000 nm. In other aspect, the nanogel has a zeta potential from about −10 mV, −15 mV, −20 mV, −25 mV, −30 mV, −35 mV, or −40 mV. In yet other aspect, the nanogel has a loading potential of about 2%, 3%, 4%, 5%, 6%, 7%, 8%, 9% or 10%.

Also provided herein are compositions which comprise one or more epigenetic drugs that alter one or more epigenetic mechanisms of a tumor cell, wherein the one or more epigenetic drugs are encapsulated in a nanogel. In particular aspects, the composition can further comprise one or more chemotherapeutic drugs encapsulated in a nanogel. The one or more epigenetic drugs and the one or more chemotherapeutic drugs can be encapsulated in different nanogels or in the same nanogel. In a particular aspect, the one or more epigenetic drugs and the one or more chemotherapeutic drug are loaded into the same nanogel, wherein the one or more chemotherapeutic agents are loaded in the nanogel's core and the one or more epigenetic drugs are loaded in the nanogel's corona.

The compositions provided herein can be delivered in a composition, as described above, or by themselves. They can be administered systemically, or can be targeted to a particular tissue. The therapeutic compounds can be produced by a variety of means, using chemical synthesis; recombinant production; in vivo production.

The compounds for use in the methods described herein can be formulated with a physiologically acceptable carrier or excipient to prepare a pharmaceutical composition. The carrier and composition can be sterile. The formulation should suit the mode of administration.

Suitable pharmaceutically acceptable carriers include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, dextrose, magnesium stearate, talc, silicic acid, viscous paraffin, perfume oil, fatty acid esters, hydroxymethylcellulose, polyvinyl pyrolidone, etc., as well as combinations thereof. The pharmaceutical preparations can, if desired, be mixed with auxiliary agents, e.g., lubricants, preservatives, stabilizers, wetting agents, emulsifiers, salts for influencing osmotic pressure, buffers, coloring, flavoring and/or aromatic substances and the like that do not deleteriously react with the active compounds.

The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, polyvinyl pyrollidone, sodium saccharine, cellulose, magnesium carbonate, etc.

Methods of introduction of these compositions include, but are not limited to, intradermal, intramuscular, intraperitoneal, intraocular, intravenous, subcutaneous, topical, oral and intranasal. The pharmaceutical compositions of this invention can also be administered as part of a combinatorial therapy with other compounds.

The composition can be formulated in accordance with the routine procedures as a pharmaceutical composition adapted for administration to human beings. For example, compositions for intravenous administration typically are solutions in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachette indicating the quantity of active compound. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration.

Suitable formulations include but are not limited to solutions, suspensions, emulsions, creams, ointments, powders, enemas, lotions, sols, liniments, salves, aerosols, etc., that are, if desired, sterilized or mixed with auxiliary agents, e.g., preservatives, stabilizers, wetting agents, buffers or salts for influencing osmotic pressure, etc. The compound may be incorporated into a cosmetic formulation. For topical application, also suitable are sprayable aerosol preparations wherein the active ingredient, preferably in combination with a solid or liquid inert carrier material, is packaged in a squeeze bottle or in admixture with a pressurized volatile, normally gaseous propellant, e.g., pressurized air.

Compounds described herein can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

In another aspect, the invention is directed to a method of sequentially delivering one or more epigenetic drugs that alter one or more epigenetic mechanisms of a tumor cell and one or more chemotherapeutic drugs to an individual that has a tumor, comprising administering a therapeutically effective amount of a nanogel to the individual, wherein the nanogel comprises one or more chemotherapeutic drug that are loaded in the nanogel's core and one or more epigenetic drugs that are loaded in the nanogel's corona.

EXEMPLIFICATION

Example 1 Sequential Drug Therapy to Overcome Drug Resistance: Study with Decitabine and Doxorubicin Encapsulated in Nanogel Delivery System Materials and Methods
Materials
N-isopropylacrylamide (NIPAM) was used after re-crystallization from n-hexane:benzene (1:3 v/v). Vinyl pyrrolidone (VP) was distilled just before polymerization. Sodium dodecylsulphate (SDS), sodium acrylate (SA), N,N'-cystaminebisacrylamide (S-S cross linker) and ammonium persulphate (APS) were used without further purification. The DNA methyltransferases inhibitor 5-aza-2'deoxycytidine and all the chemicals mentioned above were purchased from Sigma Aldrich Chemical Company (St. Louis, Mo.). Dox was obtained from Dabur chemical company India. Cell culture Media's, DPBS, Penicillin and Streptomycin were purchased from Lerner Research Institute, media lab (Cleveland, Ohio). MTS reagent was purchased from Promega (Madison, Wis.).

Cell Culture Condition
Cells were grown in DMEM supplemented with 10 or 15% fetal bovine serum (Gibco BRL, Grand Island, N.Y.) and 100 m/mL penicillin G and 100 m/mL streptomycin at 37° C. in a humidified and 5% CO2 atmosphere.

Sequential/simultaneous treatment
The efficacy of sequential treatment was tested in the following human breast cancer cell lines: MCF-7/Adr (drug resistant), MCF-7, MDAMB 231 and BT-459. Cells were seeded at 3000 cells per well/0.1 mL in 96-well plates (Microtest Becton Dickinson Labware, Franklin Lakes, N.J.). 24 h post seeding, cells were pretreated with DAC solution/nanogel for 24 h or 48 h and washed with 1×-DPBS. 0.1 mL of media containing dox solution or nanogel was added and incubated in CO2 incubator for 48 h. Cell viability was determined at the end of incubation period using a standard MTS assay (CellTiter 96 Aqueous, Promega, Madison, Wis.). To each well was added 20 µL of reagent, the plates were incubated for 2 h at 37° C. in cell culture incubator, and color intensity was measured at 490 nm using a micro plate reader (Bio-Tek Instrument, Winooski, Vt.). The effect of drug on cell proliferation was calculated as percentage growth of cells with respect to their respective controls. For simultaneous treatment DAC solution or nanogel, and dox solution or nanogel were added together to cells, and the above mentioned protocol was followed.

Synergistic Action of DAC and Dox
The interaction between DAC and dox was analyzed using the Calcusyn software program (Biosoft, Ferguson, Mo.) to determine whether the simultaneous/sequential treatment was additive or synergistic.

Data from cell viability assay (MTS) was expressed as the fraction of cells killed by individual drugs or by their combination in drug-treated compared with untreated cells. This program is based upon Chou-Talalay method. It calculates combination index (CI) of drugs. From the CI values, synergistic action of drugs can be analysed. The CI equal to 1, indicates the additive effect and CI<1 and CI>1, indicates synergistic and antagonistic activity respectively [6].

Flow Cytometry
Subconfluent cells were left untreated or treated with DAC (50 and 100 ng/mL) and dox (1 ng/mL) alone or in combination (sequential treatment) for 4-96 h. Cells were then trypsinized and then centrifuged at 1,300 rpm for 3 min at 4° C. Cell pellet was washed twice with ice cold 1X DPBS (pH 7.4) and resuspended in propidium iodide-(PI) solution (12.5 mg PI, 250 mg Sodium-Citrate and 250 µL Triton X-100 in 250 mL of water). Cells were then incubated in ice bucket, kept in cold room for 2 h, and DNA content was determined by flow cytometry using a FACScan flow cytometer (Becton Dickinson, San Jose, Calif.).

Microarray Analysis and Validation:
Microarray analysis was performed using the standard protocol provided by IlluminaCorporation (San Diego, Calif.). Briefly, total RNA was isolated from MCF7/Adr cells left untreated or treated with DAC, dox or with their combinations for 48 h, using SV Total RNA Isolation System (Promega, Madison, USA) as per the manufacturer's instruction. 20 µL of nuclease free water containing total RNA at the concentration of 100 ng/µL was stored at −80° C. Approximately 5 µg of total RNA was subjected to gene expression array study using Illuminahuman 6v2 chip. The array-hybridization and scanning of array images were performed at the Cleveland Clinic Genomics Core. The microarray scanned image and intensity files were imported into Illumina Bead Studio Analysis software version 3.2.6 (Illumina Inc.). Error models were applied and ratios were built for each treatment array versus its respective vehicle control. For qPCR analysis, RNA isolated from treated and untreated cells were converted into cDNA using Mo-MLV reverse transcriptase (Promega Inc., USA) according to manufacturers' instructions. Taqman expression primers (Applied Biosystems Inc., USA) and ABI PRISM Sequence Detection Instrument 7700 (Applied Biosystems Inc., USA) were used for real-time reverse transcription-PCR (RT-PCR). Fold change in target genes was calculated about the human glyceraldehyde 3-phosphate dehydrogenase (GAPDH).

Western Blotting

Whole cell lysates, were made by lysing 1×106 treated or untreated cells, with RIPA buffer (Sigma-Aldrich, St. Louis, Mo.) containing 1× protease inhibitor cocktail (Calbiochem, Gibbstown, N.J.). Lysates were collected by centrifugation at 14,000 rpm for 15 min Protein concentration was determined by a bicinchoninic acid (BCA) assay kit (Pierce, Rockford, Ill.). 20-40 µg proteins of cell lysates were electrophoresed through 13.5% SD Spolyacrylamide gel or 4-15% linear pre-cast polyacrylamide gradient gel (Bio-Rad Laboratories, Hercules, Calif.) and transferred to polyvinylidene difluoride (PVDF) membranes (GE Healthcare Bio-sciences, corp., Piscataway, N.J.). The blots were probed for mouse monoclonal p21 (Cell Signaling Technology, Inc., Danvers, Mass.), mouse monoclonal DNMT1 (Abcam Inc., Cambridge, Mass.), and mouse monoclonal anti-actin (Sigma-Aldrich, St. Louis, Mo.). For detection of bound antibody, PVDF membrane was incubated with horse radish—tagged, goat anti-mouse antibody. After incubation membrane was washed with TBST, and stained with enhanced chemiluminescence (ECL) reagent or ECL plus reagent (GE Healthcare Bio-sciences, corp., Piscataway, N.J.) according to manufacturer protocol.

Nanogel Synthesis

PNIPAM (poly-N-isopropylacrylamide) was synthesized by surfactant polymerization, using NIPAM in presence of S-S cross linker and APS initiator. The polymerization was conducted in a three-necked flask with nitrogen inlet and outlet at 70° C. for 6 h. Four formulations namely NG-70, NG-80, NG-85 and NG-100 were made; their composition is mentioned in table 1. NG-70 was prepared by dissolving 700 mg of NIPAM, 200 mg of SDS, 200 mg of VP and 100 mg of PEG-MA in 100 mL of MiliQ water and stirred under nitrogen for 30 min at room temperature in order to get uniform solution. The reaction temperature was raised to 70° C. and 80 mg of ammonium persulphate dissolved in 5 mL for about 5 min was introduced to initiate the reaction. Reaction was continued for 6 h at this temperature. The obtained nanogel solution was dialyzed against Mili Q water (2 L) using Spectropore® dialysis bag (mol wt cutoff 12-kD, Spectrum®, Laguna-hills, CA) for 2 weeks to remove unreacted monomer, surfactant and electrolytes by changing water every day. The aqueous solutions of nanogel was lyophilized (−80° C., <10 µm mercury pressure, Sentry™, Virtis, Gardiner, N.Y.) for 48 h to get dry powder. All other nanogel formulations were synthesized using the same protocol with the exception of NG-100; to which VP and PEGMA was not added, but 200 mg of SA was added.

The resulted nanogel solution was characterized for size by dynamic light scattering (DLS) and transmission electron microscopy (TEM). Nanogels were loaded with DAC.

PNIPAM-SA Nanogel Cytocompatibility

Human vascular smooth muscle cells (Cascade Biologics, Portland, Oreg.) were maintained in medium 231 supplemented with smooth muscle growth supplement (Cascade Biologics) at 37° C. in a humidified, 5% CO2 atmosphere. Cells at passage 5 were typically used. 5,000 cells/0.1 mL/well were seeded in 96 well plate. 24 h post seeding, different doses of void nanogel (0-500 µg/mL), dispersed in cell culture media was added and incubated for 72 h. Medium in the wells was changed after 72 h and on every alternate day thereafter with no further addition of nanogels. Cell viability was done on eighth day using MTS assay as described above.

DAC or Dox Loading in Nanogel

DAC in DMSO (300 µL, 8.1 mg/mL) or ethanolic solution of hydrophobic dox (200 µL, 5 mg/mL) was added to nanogels dispersed in MiliQ water (5 mg/mL, 6 mL). DAC added nanogel suspension was stirred for 3 h on a magnetic stirrer in cold room. Dox added nanogel suspension was stirred initially for 2 h at room temperature in a glass vial with cap closed and then for 4 h with cap opened in a fume hood with air flow set at 240 fpm. DAC and dox loaded nanogel suspension was dialyzed against MiliQ water in a dialysis bag (MWCO 12-kD, Spectrum®, Laguna Hills, Calif.) for 30 min and 6 h respectively to remove unentrapped drug. The nanogel suspension was lyophilized for further study.

Estimation of DAC or Dox Loading in Nanogel

To estimate DAC or dox loading in nanogels, 2 mL of methanol or 2 mL of 12.5% methanolic solution in chloroform was added to 1 mg of DAC or dox loaded nanogel. For DAC or dox extraction; nanogel suspension was stirred overnight on a magnetic stirrer kept at 4° C. or at room temperature. Nanogel suspension was centrifuged at 14,000 rpm for 10 min at 4° C. to remove nanogels. The concentrations of DAC and dox in supernatant was determined using HPLC (Shimadzu Scientific Instruments, Inc., Columbia, Md.) and fluorescence spectrophotometer (LS55 Fluorescence Spectrophotometer, PerkinElmer LLC, Shelton, Conn.) at $\lambda_{ex}$=485 nm and $\lambda_{em}$=591 nm respectively. A standard plot of DAC (0-200 µg/mL) or dox (0-10 µg/mL) was prepared under identical conditions.

HPLC Conditions

Stationary phase: C18 reversed phase column (Atlantis T3-4.6×250 mm2-5 µm); Mobile phase: Sterile degassed methanol: water (60:40); Injection vol: 25 µL; Flow rate: 1.2 mL/min, isocratic mode for 6 min wavelength—228 nm, UV detector.

Particle Size and Zeta Potential Measurements:

The mean hydrodynamic particle size of nanogels before loading and after loading the drug was determined in water by DLS at a scattering angle of 90° at 25° C. using NICOMP™380 ZLS (Particle Sizing Systems, Santa Barbara, Calif.). The suspension of nanogels prepared in water was used to measure zeta potential in phase analysis mode and the current mode at a scattering angle of −14°.

Transmission Electron Microscopy

Nanogels were characterized for size using transmission electron microscope (TEM) (Philips 201 TEM, Philips/FEI Inc., Briarcliff Manor, N.Y.) operating at 200 kV. For TEM measurements, a drop of nanogel suspension (500 µg/ml) prepared in water was placed on 200 mesh formvar-coated copper TEM grid (grid size: 97 µm) (TEDPELLA, Redding, Calif., USA) to which 2% w/v of uranyl acetate solution (negative stain) was added. The excess solution was removed using a piece of filter paper and the samples were allowed to dry in air for 5 h prior to imaging. From TEM images nanogels size were measured using image J software.

DAC Stability in Cell Culture Media

50 µg/mL of freshly made DAC solution or DAC loaded nanogel was dispersed in cell culture media (DMEM supplemented with 15% FBS and 1% penicillin-streptomycin), and incubated in cell culture hood at 37° C. Samples were incubated as 2 mL aliquots at 37° C., collected at various time points and lyophilized. To extract DAC from lyophilized samples 3 mL of methanol was added and kept on orbital rotating shaker at 100 rpm in cold room overnight. 1 mL of methanolic extract was centrifuged at 14,000 rpm for 15 min at 4° C., supernatant was collected and analysed by HPLC as mentioned above.

Results

DAC in Combination with Dox-Cell Viability

Figure 1A:
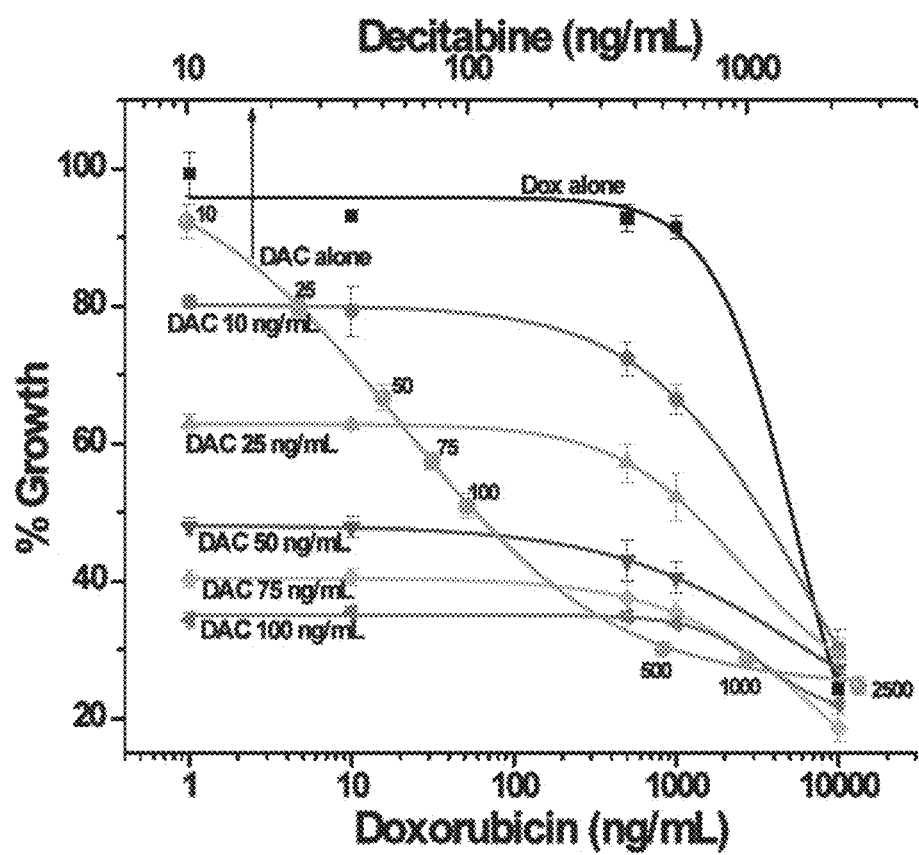
FIGS. 1a-1c: 1a) Sequential treatment of decitabine (DAC) and doxorubicin (dox) on MCF-7/Adr cells; pretreated with DAC for 24 h. 1b) Comparison of sequential and simultaneous treatment of DAC and dox on MCF-7/Adr cells. For sequential treatment, cells were pretreated with DAC for 24 h. 1c) Combination index values of DAC and dox and/or taxol, on sequential and simultaneous treatment in MCF-7/Adr cells.

Dox is one of the most active cytotoxic agents for treatment of breast cancer. Dox in solution exhibited typical sigmoidal dose dependent antiproliferative activity in both dox resistant and in dox sensitive cell lines. Dox showed significant difference in $IC_{50}$ values in resistant and sensitive cell lines (7385 ng/mL vs 19-102 ng/mL) (Table 1). However, when pretreated with DAC, drug resistant cells became highly sensitive to dox, even lower most concentration (1 ng/mL) of dox was sufficient to achieve $IC_{50}$ (FIG. 1a).

Figure 1B:
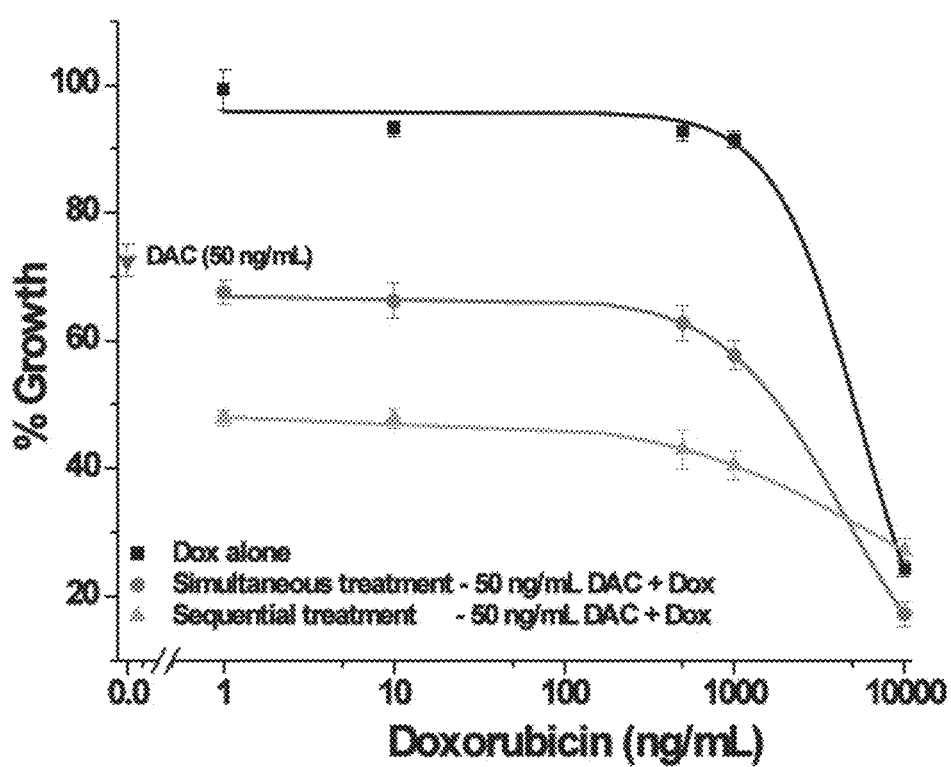
Figure 1C:
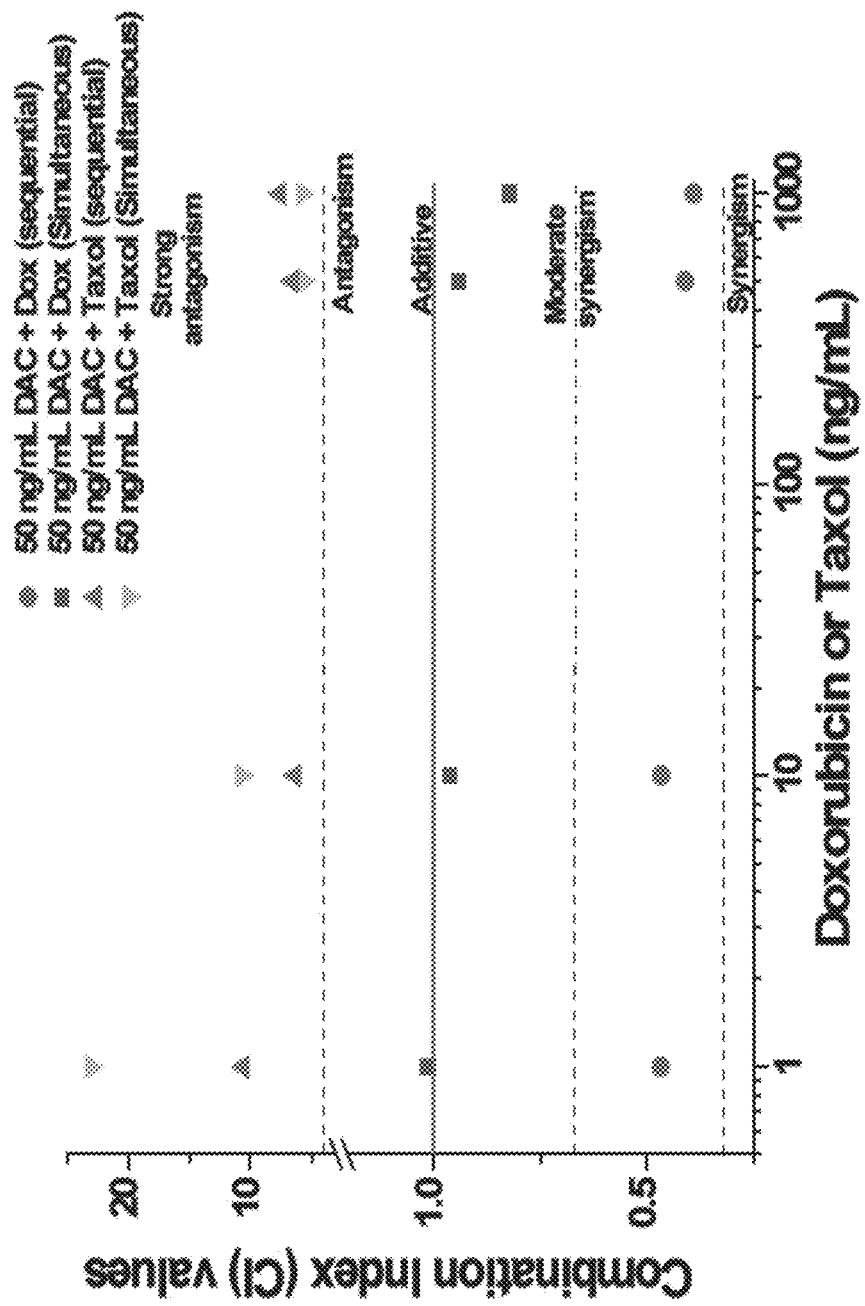

The percent survival decreased in both dox resistant and sensitive cells, pretreated with DAC for 24 h (Table 1); however increase in exposure time of DAC to 48 h, did not decrease survival anymore. Based on this result, for further study, we favored 24 h pretreatment instead of 48 h. Further, sequential treatment of DAC and dox showed much better antiproliferative activity than simultaneous administration (FIG. 1b). In addition to this, mathematical analysis of data as described by Chou et al. [6] had confirmed that the sequential administration of DAC and dox to be more synergistic than simultaneous administration. Combination of DAC and taxol both in sequential and simultaneous administration demonstrated antagonistic activity in drug resistant breast cancer cells (FIG. 1c). Results of this study clearly indicate that the sequential administration of DAC and dox could be more effective than simultaneous administration of DAC and dox and/or taxol and DAC.

Based on the results of MTS assay, 50 ng/mL of DAC and 1 ng/mL of dox were selected for further study.

Cell Cycle Analysis by Flow Cytometry

Figure 2A:
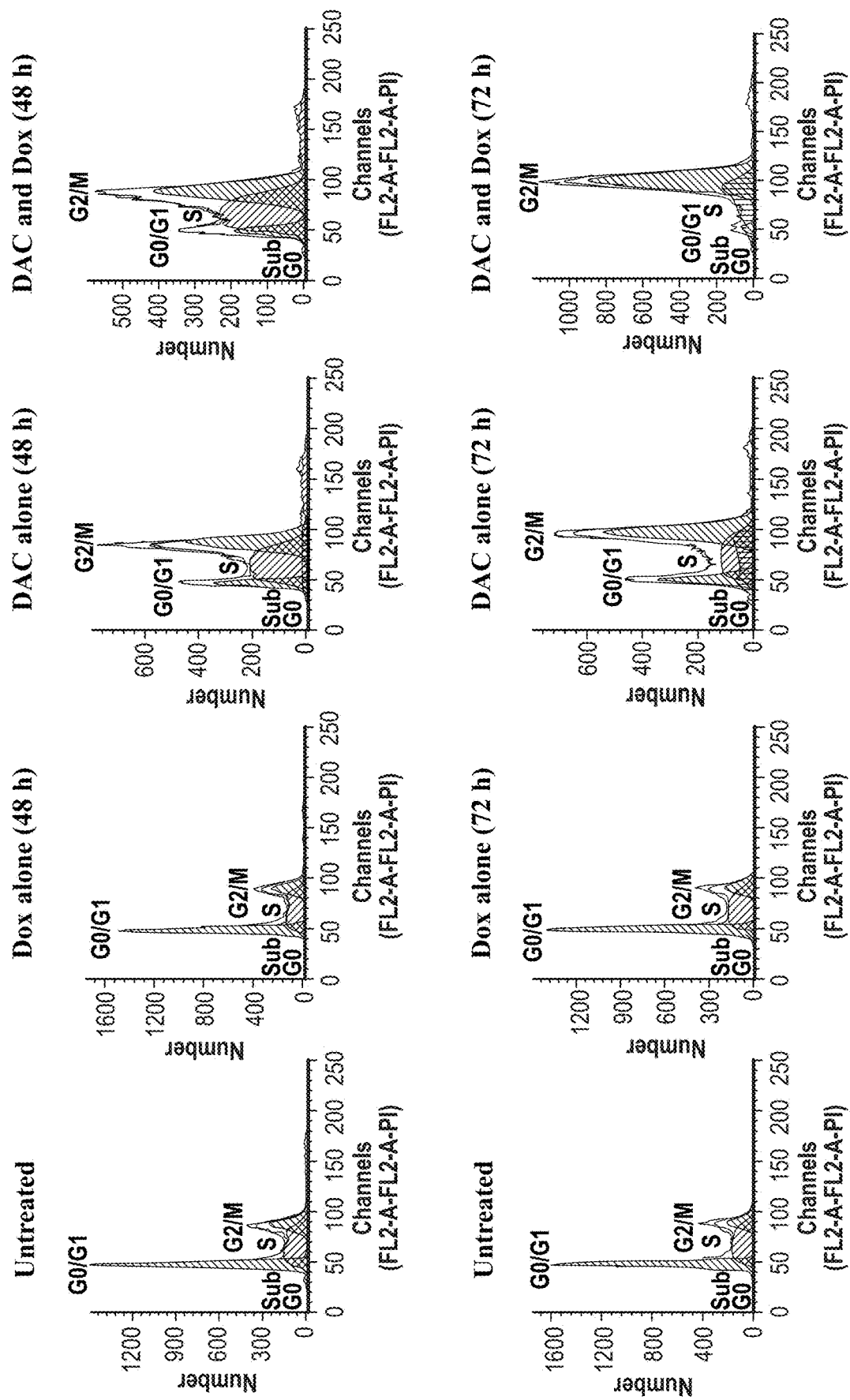
FIGS. 2a-2b: 2a) Cell-cycle analysis of MCF-7/Adr cells sequentially treated with DAC and dox at various time points. Dose of DAC 50 ng/mL, dose of dox 1 ng/mL. 2b) Cell cycle analysis of MCF-7 cells sequentially treated with DAC and dox at various time points. Dose of DAC 50 ng/mL, dose of dox 1 ng/mL.
Figure 2B:
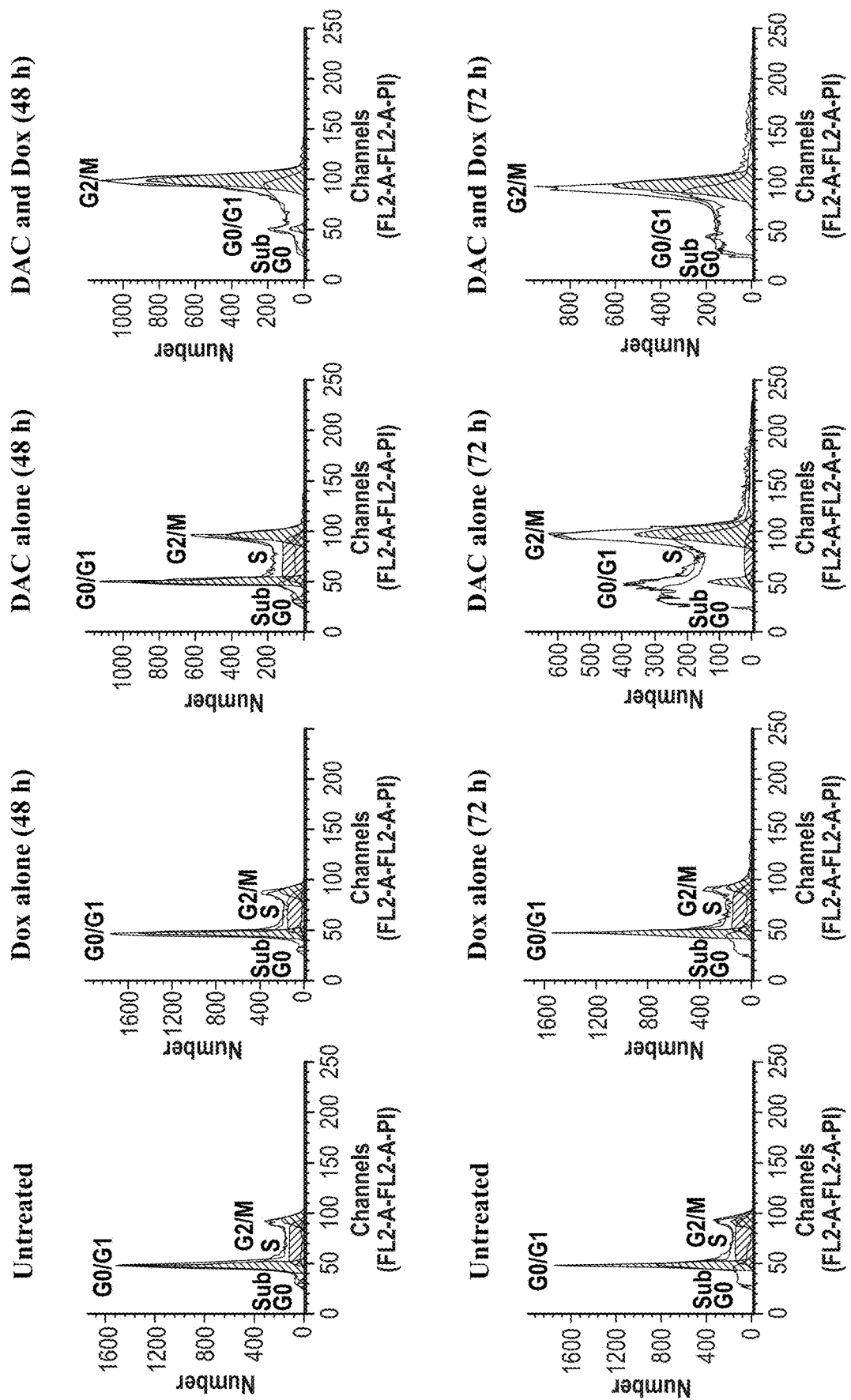
Figure 3A:
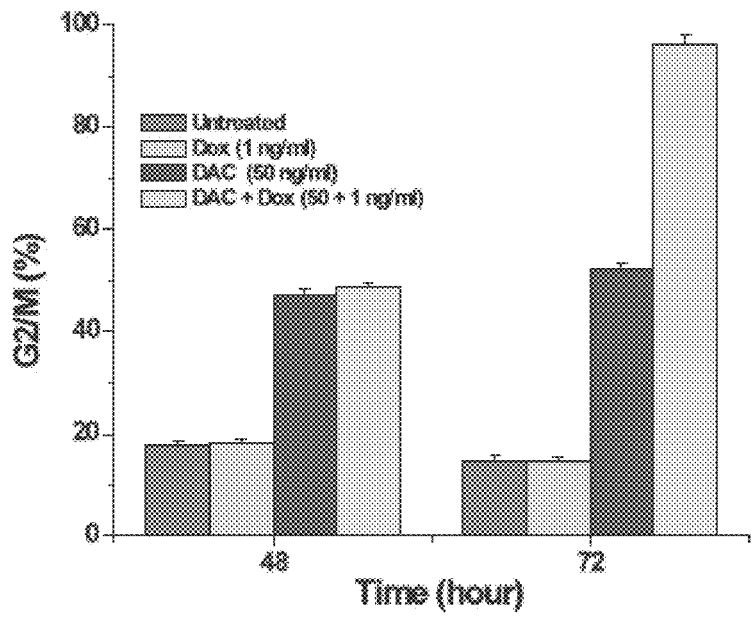
FIGS. 3a-3b: 3a) DAC alone or its combination with dox arrested MCF-7/Adr cells at G2/M phase of cell cycle. Dose of DAC 50 ng/mL, dose of dox 1 ng/mL. 3b) DAC alone or its combination with dox arrested MCF-7 cells at G2/M phase of cell cycle. Dose of DAC 50 ng/mL, dose of dox 1 ng/mL.
Figure 3B:
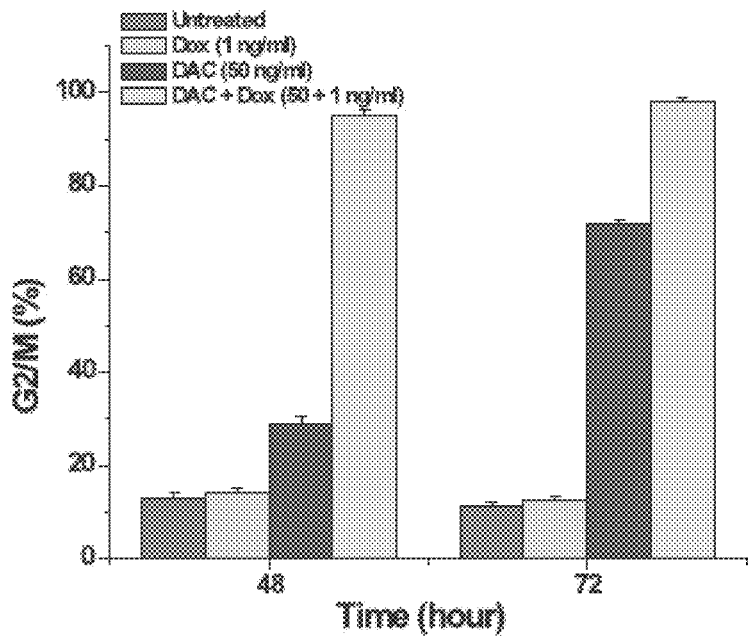

The cell cycle analysis shows that MCF-7/Adr and MCF-7 cells pretreated with DAC and then with dox, shown significant G2/M arrest at 48 h and 72 h on comparison to DAC alone or untreated cells (FIGS. 2a and 2b; 3a and 3b). Dox alone treatment showed no difference at all time points when compared with untreated cells (FIGS. 3a and 3b). Our cell cycle analysis had confirmed that DAC and dox has synergistic activity at the concentrations of 50 and 1 ng/mL respectively.

Further to find the mechanism of cell cycle arrest and the genes that get activated and involved in G2M arrest, a gene array was done on MCF-7/Adr cells sequentially treated with DAC (50 ng/mL) and dox (1 ng/mL).

Results of microarray analysis showed a marked change in gene expression ($\geq$ or $\leq 2.5\times$) by DAC even at the lowest concentration (50 ng/ml) but not by dox. The sub-cellular localization, ontological function and fold change of genes up-regulated or down-regulated by $\geq 2.5\times$ in DAC alone treated group, when compared with the untreated group was shown in table 3. No significant difference in number of genes got expressed or their fold change was observed between DAC alone and its combination with dox (data not shown). Several genes including p19, p21 and PAK3 that were involved in cell cycle regulation was found to be induced by DAC or by its combination with dox (FIG. 4a), which was in agreement with our cell cycle analysis results (FIG. 2).

Figure 4A:
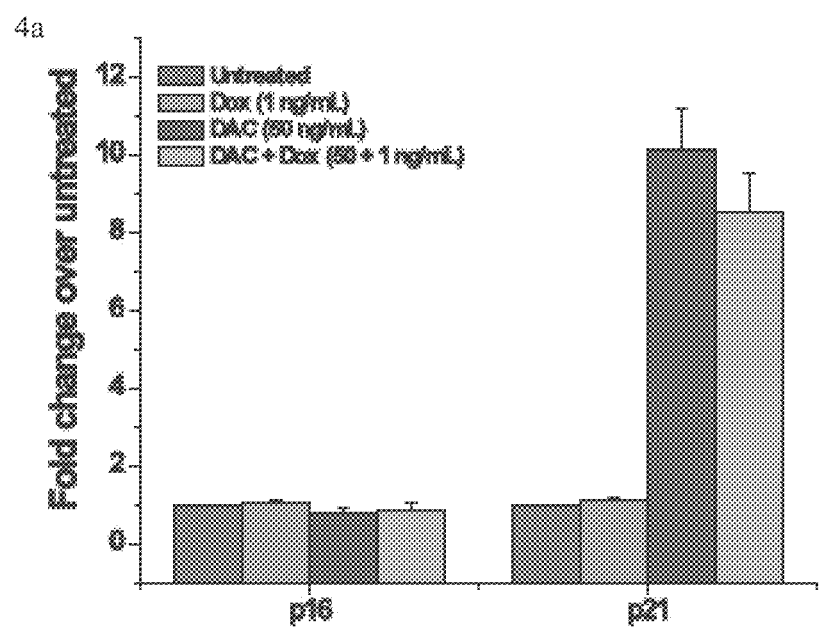
FIGS. 4a-4b: 4a. Semiquantitative RT-PCR analyses of p21 using taqman probes. Expression of p16, was used as a negative control. DAC alone or its combination increased the expression of p21 by >4 fold at 48 h. 4b. Western blotting analyses of p21 in MCF-7/Adr. Whole protein from untreated, dox alone, deci alone and deci in combination with dox treated groups were loaded in lanes 1-4. p21 showed increased expression in DAC alone and its combination with dox. Actin served as loading control.
Figure 4B:
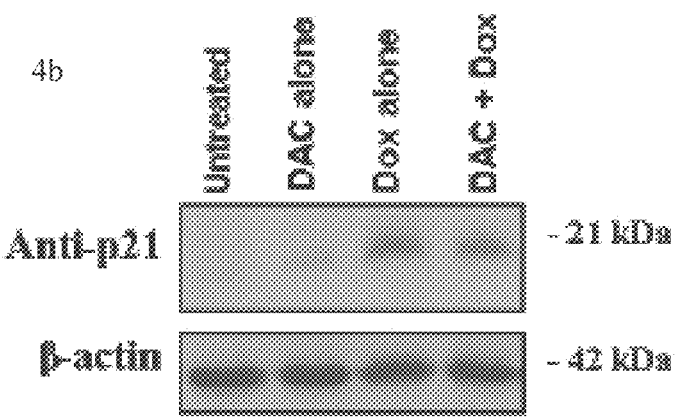
Figure 7A:
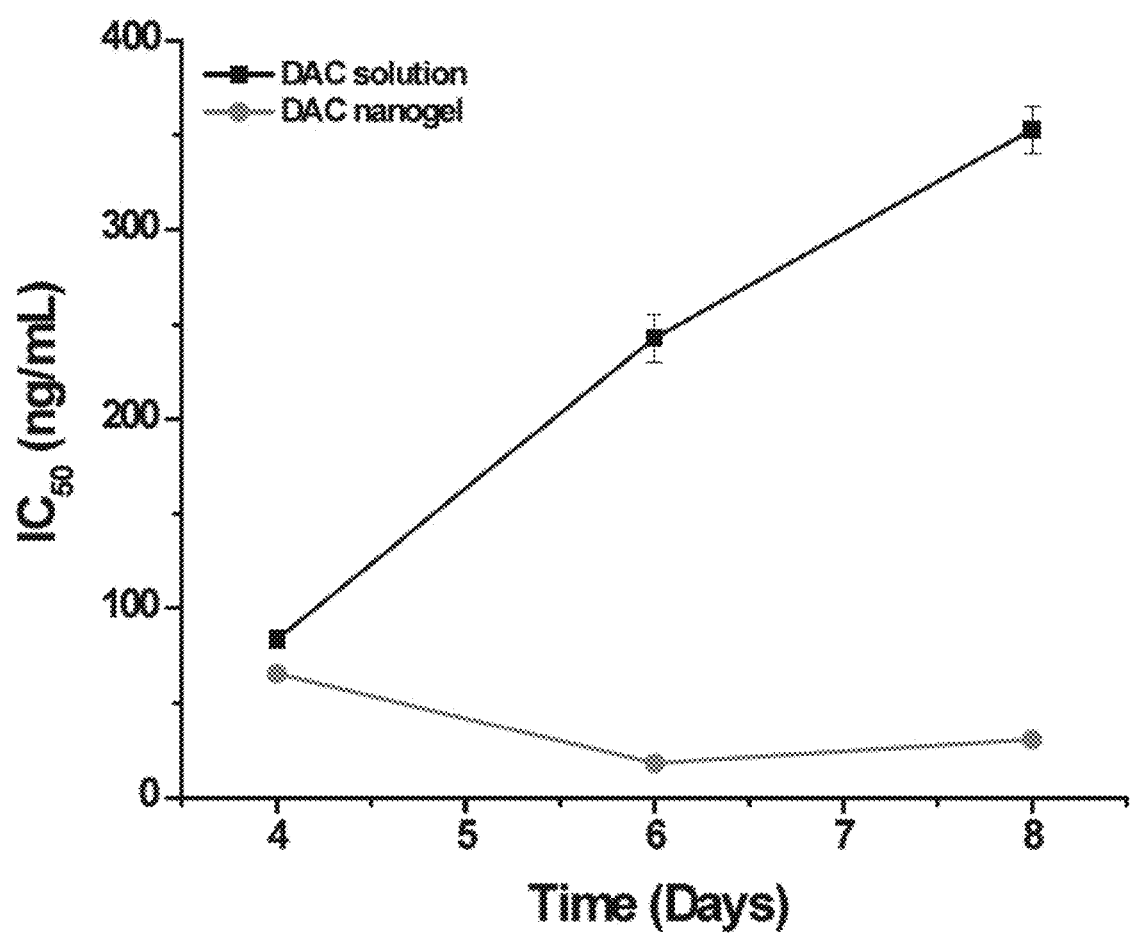
FIGS. 7a-7d: 7a) Comparison of $IC_{50}$ value of DAC solution and DAC nanogel in MCF-7/Adr cells treated for 4, 6 and 8 days. Data expressed as mean±s.e.m from three individual experiments. 7b) Comparison of sequential treatment of DAC solution and dox solution with DAC nanogel and dox nanogel in MCF-7/Adr cells. Concentration of DAC nanogel or DAC solution—50 ng/mL, concentration of dox—1 ng/mL. 7c) MCF-7/Adr cells treated with DAC nanogel or with DAC solution for 1-5 days; cell lysates were collected at the end of each time point and analyzed by western blot. Whole cell lysates of untreated and DAC solution treated for 1, 2, 3 and 5 day without changing media, was loaded in lanes 1-5. Lanes 6-9 were loaded with whole protein from cells treated with DAC nanogel for 1, 2 3 and 5 days without changing media. 7d) DNMT1/actin ratio of MCF-7/Adr cells treated with DAC solution or nanogel. DAC solution depleted DNMT1 for 24 h on comparison to untreated. No difference in DNMT1 levels were observed in samples collected at 2, 3 and 5 days post treatment with DAC solution when compared with untreated. DAC nanogel treatment showed lower levels of DNMT1 at all the time points studied than untreated. Two individual experiments gave similar result.
Figure 7B:
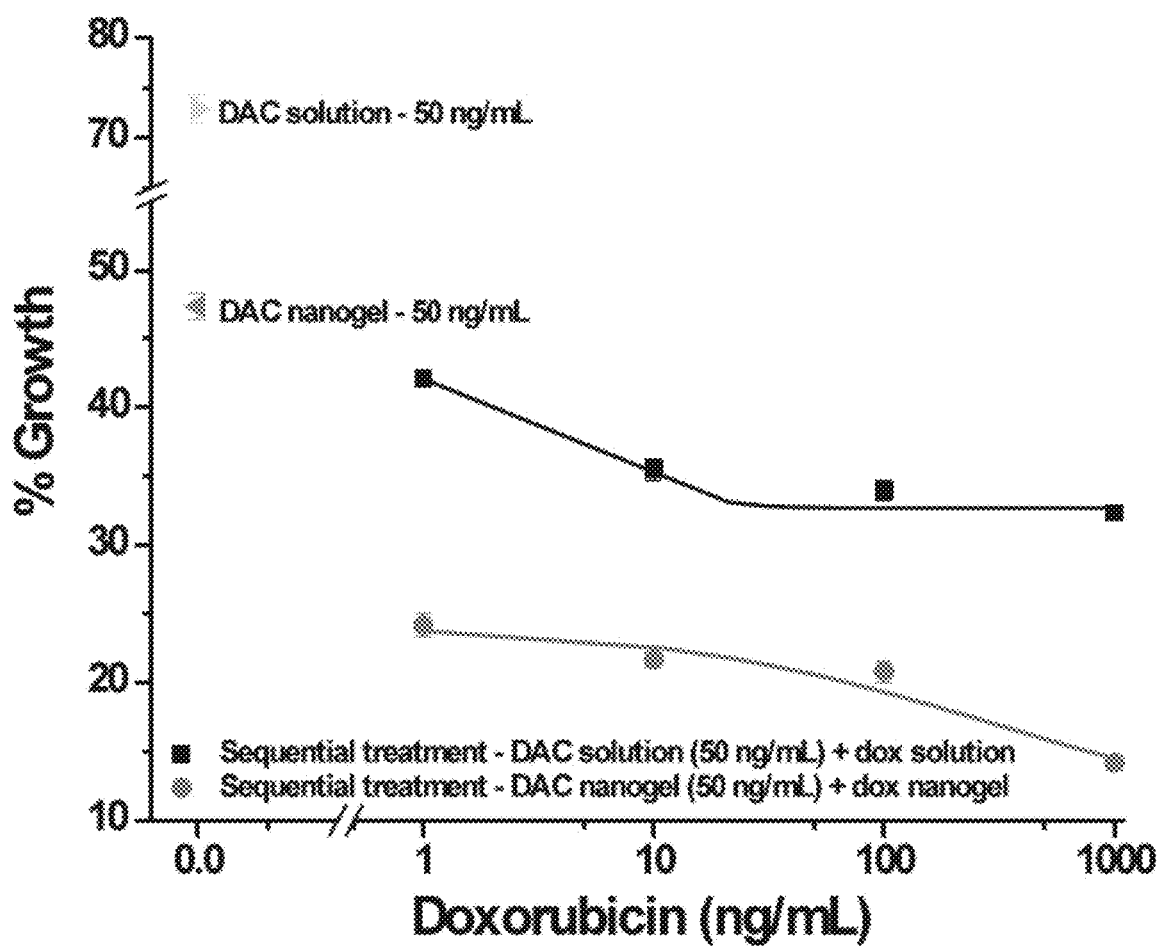
Figure 7C:
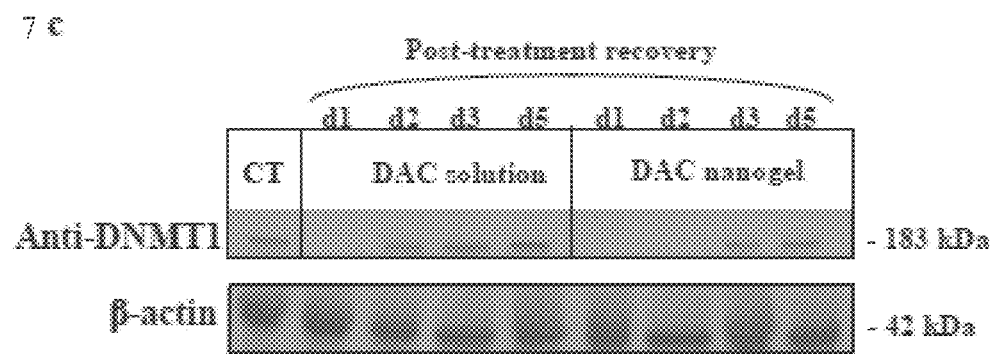
Figure 7D:
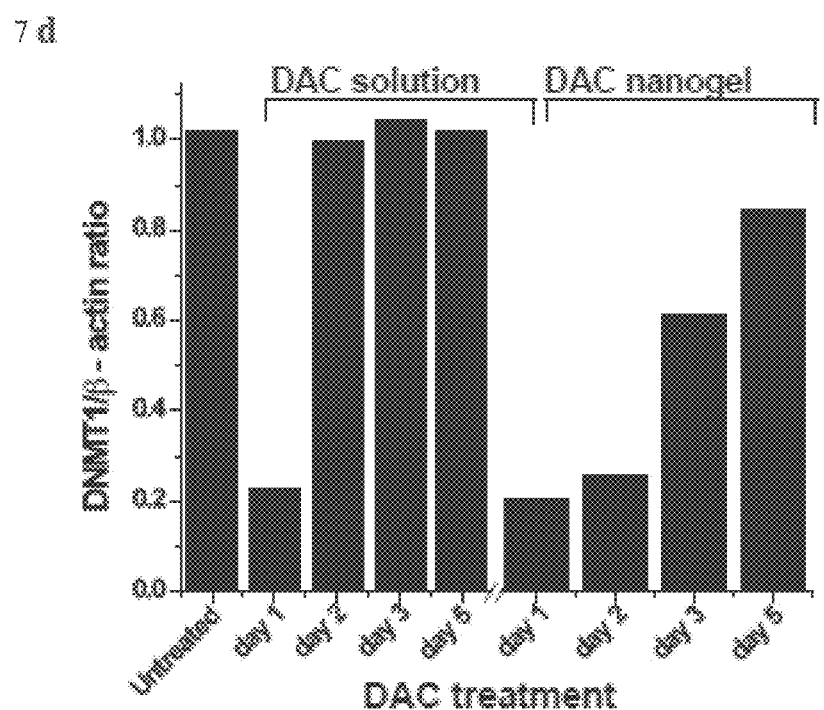

The RT-PCR analyses to confirm the induction of p21 mRNA, had shown, DAC alone or its combination with dox markedly increased the expression of p21 by >4 fold at 48 h. Under these conditions the expression of p16 (negative control) was unaltered (FIG. 4a). Further, our immunoblotting results showed significant increase in p21 protein expression in both DAC alone and its combination with dox (FIG. 4b), which inturn correlated very well to the depletion of DNMT1 by DAC treatment for 24 h (FIG. 7d). Results of this study clearly indicate that the depletion of DNMT1, results in, induction of methylation suppressed p21 gene in MCF-7/Adr cells.

Physical Characterization of PNIPAM-SAHA Nanogels

Figure 5A:
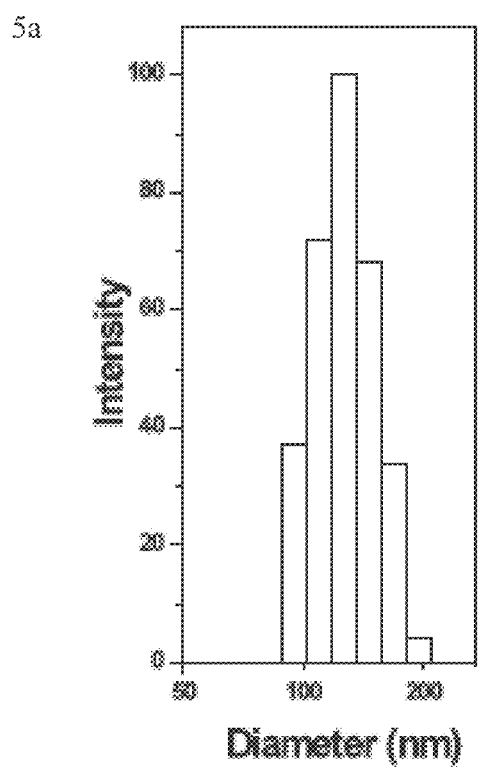
FIGS. 5a-5b: 5a) Hydrodynamic particle size distribution of DAC loaded PNIPAM-SA nanogel in water measured by using dynamic laser light scattering. 5b) Transmission electron micrograph of DAC loaded PNIPAM-SA nanogel.
Figure 5B:
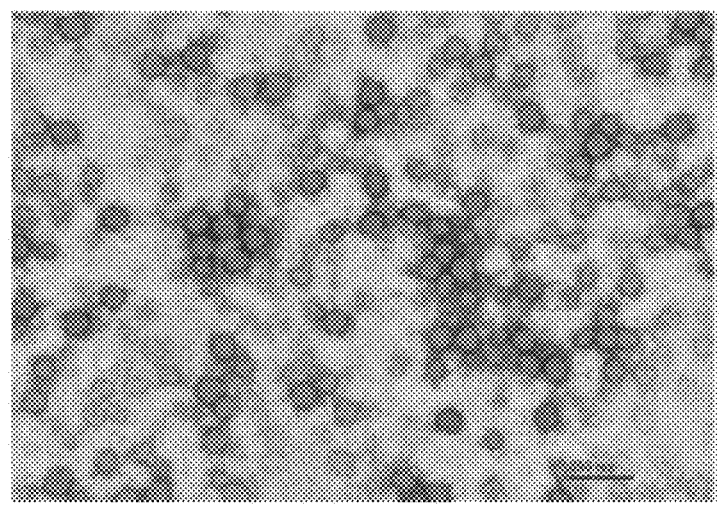

The mean hydrodynamic diameter of PNIPAM-SAHA nanogel with and without drug encapsulation was at the range of 98 to 120 nm, indicating incorporation of drug had no significant effect on the mean hydrodynamic size of nanogel (FIG. 5a and Table 4). PNIPAM-SAHA nanogel showed negative zeta potential in water and loading of drug did not change the zeta potential of nanogel. TEM images of both blank and drug loaded nanogel shown almost spherical shape, with size at the range of 55 to 62 nm respectively (Table 3). Loading efficiency and loading content of DAC in nanogel was found to be 85% and 6.8 wt % respectively. However, loading of hydrophobic dox was lower (2.8 wt %).

Physical Characterization of PNIPAM-VP-PEGMA Nanogels

Hydrodynamic diameter of void and drug loaded nanogels (NG-80 and NG-85) were at the range of 125 to 135 nm (Table 5). NG-70 shown increase in size (234 nm) than other nanogels, this might be due to increase in % VP in it. VP increases hydrophilicity and water flux of a system [7], and it could be a reason for observed significant increase in size of NG-70 in comparison with other two nanogel formulations by DLS measurement. All nanogel formulations with and without drug; showed negative zeta potential in water (Table 5).

Loading of DAC in PNIPAM-VP-PEGMA nanogels were at the range of 4-6 wt %. No difference in loading was observed between NG-80 and NG-85. DAC loading was lower in NG-70 on comparison to other two nanogels. However, loading of DAC was more in PNIPAM-SA nanogel than in all other formulations. Further, particle size of PNIPAM-SA nanogel were lesser compared to all other formulations, so we used PNIPAM-SA as the vehicle to load and deliver DAC for further study.

Comparison of Stability of DAC Loaded Nanogel or DAC Solution Dispersed in Cell Culture Media (DMEM with 15% FBS)

Figure 6:
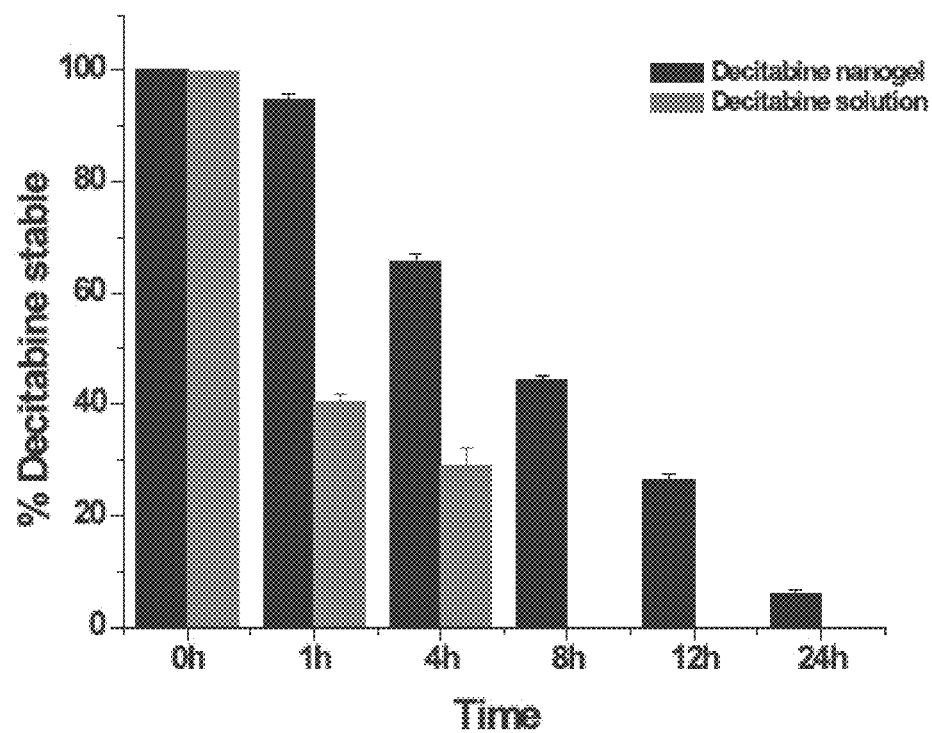
FIG. 6: Comparison—stability of DAC and DAC nanogel in cell culture media supplemented with 15% FBS and 1% penicillin streptomycin.

The stability study shows that DAC encapsulated in nanogel has greater stability than in solution. DAC showed no degradation at 1 h, and detectable levels of DAC were found till 24 h when loaded in nanogel. Whereas, 60% of DAC in solution degraded within an hour, and no detectable levels of DAC was found at 8 h (FIG. 6).

Comparison of Efficacy of DAC Nanogels and DAC Solution in Drug Resistant Breast Cancer Cell MTS assay results of MCF-7/Adr cells treated with DAC or dox nanogel alone showed better antiproliferative activity than DAC or dox solution. Further, DAC nanogel demonstrated better cytotoxicity than DAC solution for longer period of time (FIG. 7a). Sequential treatment of DAC nanogel with dox nanogel showed more synergistic activity on comparison to sequential treatment of DAC solution and dox solution (FIG. 7b). Void nanogel showed no toxicity at all the concentrations tested, indicating their cytocompatibility. Result of this study suggests that the increase in stability of DAC when incorporated in nanogel could have increased its efficacy, resulting in better antiproliferative activity than drug in solution.

Impact of DAC Solution or DAC Nanogel Treatment on DNMT1 Depletion in MCF-7/Adr Cells DAC administration to cells results in incorporation of DAC into DNA, and covalently binds to DNMT1 leading to reduction of available DNMT1 protein in cells, which in-turn results in demethylated genes in daughter cells. However, this effect is transient. Duration of DNMT1 depletion could be based on the availability of DAC to cells. Since we found that DAC degrades within an hour in cell culture media, treatment of cells with DAC solution may not deplete DNMT1 for longer period of time. Hence to know the duration of DNMT1 depletion, we treated cells with 50 ng/mL DAC solution or with DAC nanogel for 1 to 5 days. Whole cell lysates were collected at the end of each time point and western blot was done for the expression of DNMT1.

DAC solution depleted DNMT1 for 24 h. No difference in DNMT1 levels were observed in samples collected at 2, 3 and 5 days post treatment on comparison to untreated cells (FIGS. 7c and 7d). Whereas, cells treated with DAC nanogel, showed lower levels of DNMT1 expression at all the time points studied when compared with control or with DAC solution, indicating that DAC nanogel can deplete DNMT1 for longer period of time than DAC solution, and it could be due to increased stability of DAC nanogel on comparison to DAC solution in cell culture media (FIGS. 7c and 7d).

Discussion and Conclusion:

From our studies we found that DAC pretreatment might overcome drug resistance in cancer cells by depleting DNMT1 protein, which inturn results in expression of methylation suppressed genes including p21. Induction of p21 expression by DAC treatment resulted in G2/M arrest of MCF-7/Adr and MCF-7 cells. Topoisomerase II α (topo IIα) levels are reported to be high in G2/M phase [8], so the arrest of cells in G2/M by pretreating them with DAC might result in increased accumulation of topo IIα than in untreated cells. Dox utilizes topo IIα to induce DNA damage and achieve its cytotoxic effect [9]. Sequential treatment of DAC and dox might be more beneficial to overcome drug resistance and to enhance the cytotoxicity of dox towards tumor cells. Dox, in addition to its toxicity towards tumor cells, also promotes cardiotoxicity [10]. Risk of dox induced cardiomyopathy and congestive heart failure (CHF) increases with cumulative dose and with patients age [11-13]. Hence, the reduction in dose of dox without affecting its efficacy could be beneficial. In our study, we observed very low levels of dox are needed to achieve 50% growth inhibition in drug resistant cell line pretreated with DAC. DAC pretreatment could be highly beneficial in reducing the amount of dox required to achieve the desired cytotoxic activity. Thereby toxicity of dox in cancer patients could be lowered.

Pre-treatment with DAC also reactivates several methylation suppressed genes. In our study, in addition to reactivation of p21, we also found the induction of tumor suppressor genes such as SOCS-1[14], CST6 [15] and THY-1 [16] by DAC treatment.

SOCS-1 was reported to be methylation silenced gene in breast [17, 18] and in various other specific cancers [19-23]. It's silencing in cancers leads to abnormal activation of STAT3 by JAK pathway and increase cell proliferation and survival of cancer cells [24]. Its expression was reported to inhibit the growth of various cancers [19-23], including breast and ovarian cancer [17] by negatively regulating the JAK/STAT pathway. Hence, it is evident from these reports that SOCS-1 acts as a negative growth regulator of cancer cells and, its induction in our study might play a role in inhibiting the proliferation of drug resistant breast cancer cell. Similar to SOCS-1, re-expression of CST6 and THY-1 was also reported to inhibit the growth of cancer cells in vitro [16, 25] and in vivo [26]. RASD1, another gene expressed several folds higher in DAC treated group than untreated, in our study, was also reported to inhibit growth of cancer cell lines both in vitro and in vivo [27]. Indicating, DAC treatment either alone or in combination with other anticancer agents is of value to treat various cancers.

In addition to up-regulation of genes, DAC also down-regulated many genes, of that MMP-9 (Matrix metalloprotease-9) is a key gene which plays a major role in tumor metastasis and angiogenesis.

MMPs promote tumor progression by degrading extra cellular matrix (ECM) [28]. MMP-9 degrades collagen IV, a major protein in ECM. degradation of ECM provides necessary space for tumor growth and for metastasis [29]. MMP-9 along with its family members was reported to promote angiogenesis by degrading vascular basement membrane [30]. Hence, the observed down regulation of MMP-9 and TFF2 (a gene stimulates breast cancer cells to migrate [31]) in our study, suggests that DAC treatment might inhibit tumor metastasis in vivo.

Based on these reports, it can be concluded that DAC up-regulated or down-regulated genes, either alone or in combination with one another might have suppressed the proliferation of MCF-7/Adr cells in vitro, in our study. However, molecular mechanism behind cell cycle arrest and the interplay between expressed tumor suppressor genes and cell cycle regulator gene p21 has to be revealed. Since p21 was not expressed in untreated drug resistant cells, and re-expressed upon DNMT1 depletion by DAC treatment, it can be concluded that p21 might be methylation suppressed gene in drug resistant cells and reexpress upon treatment with demethylating agent—DAC.

Since our goals are to know whether the combination of DAC with anticancer drugs could be beneficial or not, and to encapsulate DAC in polymer nanogels to increase its stability and efficacy, we did not investigate the molecular mechanism behind cell cycle arrest in drug resistant breast cancer cells in detail.

Even though, DAC treatment induces tumor suppressor genes and shows good synergy in combination with dox in vitro. DAC rapidly degrades in solution, and DNMT1 levels were also found to be reverted to normal levels in cell lysates collected at day 2 post treatment with DAC solution (FIG. 7d). Further, effect of DAC has been reported as transient in vivo. Hence, to prevent degradation of DAC in solution and to increase its efficacy, we had encapsulated it in polymer nanogels. Nanogels are 10-200 nm sized, three dimensional networks made up of biocompatible hydrophilic polymeric chains [32]. We had increased the stability of DAC by loading in polymer nanogel, and its efficacy correlated very well with its increased stability. We were first to report the increase in stability and efficacy of DAC without doing any chemical or physical modification to DAC. We also showed prolonged depletion of DNMT1 levels when treated with DAC nanogel than with DAC solution. Hence, DAC nanogel could be highly advantageous in vivo to deplete DNMT1 and to re-express tumor suppressor genes than DAC solution. Further, due to small size (~100 nm), nanogels can be easily taken up by cells and can be injected either directly in to the tumor or intravenously. We had described the synthesis, and characterization of nanogels in detail in a research article published by our lab [32].

Hence, to conclude, from our studies; we found DAC and dox to exhibit strong synergism in sequential treatment than in simultaneous treatment. DAC did not show synergy with taxol. Since, antagonism between taxol and DAC has been demonstrated by Tabuchi et al, in estrogen negative breast cancer cells (KPL-4 and ZR-75-30) [33]. We did not further investigate the antagonism exhibited by taxol and DAC. Hence, DAC in sequential treatment with dox could be beneficial in overcoming drug resistance in breast cancer cells. Since, DAC is highly unstable in solution and its effect is transient, we had encapsulated it in polymer nanogel. Incorporation of DAC in polymer nanogel had increased its stability and efficacy when compared with DAC solution.

We found DAC treatment alone or in combination with dox to induce the expression of p21 (cell cycle regulator) and tumor suppressor genes, by depleting DNMT1 protein. Further, we had shown prolonged depletion of DNMT1 in MCF-7/Adr cells, when treated with DAC nanogel than with DAC solution. In addition to this, sequential administration of DAC and dox loaded in nanogel demonstrated better antiproliferative activity than sequential treatment of DAC and dox solution. Cells pre-treated with DAC nanogel required only very low levels of dox to achieve desired cytotoxicity. Hence, combination of DAC nanogel and dox nanogel could overcome drug resistance in cancer cells and also could reduce dox induced cardiotoxicity in vivo.

TABLE 1

Sequential treatment of deci and dox in breast cancer cell lines.

| Cell Line | Type | $IC_{50}$ (Dox ng/mL) | $IC_{50}$ (Sequential - Deci + Dox ng/mL) | CI Value |
|---|---|---|---|---|
| MCF-7/Adr | Human drug resistant breast cancer cells | 7385.2 ± 698 | <1 | 0.2 ± 0.1 |
| MCF-7 | Human breast cancer cells | 20.7 ± 0.8 | 7.4 ± 1.3 | 0.81 ± 0.1 |
| MDA MB-231 | Human breast cancer cells | 19.3 ± 1.9 | 4.4 ± 0.1 | 0.31 ± 0.1 |
| BT 459 | Human breast cancer cells | 102.2 ± 4.7 | 25.0 ± 5.5 | 0.61 ± 0.1 |

Data expressed as mean ± s.e.m. from three individual experiments

TABLE 2

Genes up-regulated by >2.5x and down regulated by >10x by decitabine treatment in MCF-7/Adr cells when compared with untreated cells.

| S. No. | Gene Symbol | Entrez Gene I.D. | Description | Fold Change 48 h | Sub Cellular Location | Function |
|---|---|---|---|---|---|---|
| 1 | GAGE2 | 729447 | G antigen 2 | 1754.4 | Cytoplasm and Nucleus | Unknown |
| 2 | GAGE5 | 2577 | G antigen 5 | 1358.9 | Cytoplasm and Nucleus | Unknown |
| 3 | GAGE7B | 26748 | G antigen 7B | 907.8 | Cytoplasm and Nucleus | Unknown |
| 4 | GAGE6 | 2578 | G antigen 6 | 813.8 | Cytoplasm and Nucleus | Unknown |
| 5 | GAGE8 | 100101629 | G antigen 8 | 411.0 | Cytoplasm and Nucleus | Unknown |
| 6 | STK31 | 56164 | serine/threonine kinase 31 | 1663.3 | Cytoplasm | Protein serine/threonine kinase activity, nucleotide binding |
| 7 | THY1 | 7070 | Thy-1 cell surface antigen | 103.1 | Plasma Membrane | Cell-cell adhesion and cytoskeletal organization |
| 8 | CST6 | 1474 | Cystatin E/M | 52.8 | Extracellular | Cysteine-type endopeptidase inhibitor activity |
| 9 | RASD1 | 51655 | RAS, dexamethasone-induced 1 | 35.6 | Plasma Memebrane | Cell adhesion, extracellular matrix interactions, and in dexamethasone-induced alterations in cell morphology |
| 10 | TMEM101 | 84336 | Transmembrane protein 101 | 33.7 | Integral to Membrane | Signal transduction |
| 11 | PAGE5 | 90737 | P antigen family, member 5 (prostate associated) | 25.4 | Cytoplasm and Nucleus | Unknown |
| 12 | SOCSI | 8651 | Suppressor of cytokine signaling 1 | 28.2 | Intracellular Nucleus | Protein kinase inhibitor, negative regulator of JAK/STAT pathyway |
| 13 | PYCARD | 29108 | PYD and CARD domain containing | 23.6 | Cytoplasm | Pyrin domain binding, capase activator activity |

TABLE 2-continued

Genes up-regulated by >2.5x and down regulated by >10x by decitabine treatment in MCF-7/Adr cells when compared with untreated cells.

| S. No. | Gene Symbol | Entrez Gene I.D. | Description | Fold Change 48 h | Sub Cellular Location | Function |
|---|---|---|---|---|---|---|
| 14 | PAGE 4 | 9506 | P antigen family, member 4 | 11.6 | Cytoplasm | Multi-functional cytokine that plays a role during embryonic development |
| 15 | SOX15 | 6665 | SRY (sex determining region Y)-box 15 | 10.2 | Nucleus | RNA polymerase transferase II activity |
| 16 | CDKN1A | 1026 | Cyclin-dependent kinase inhibitor1A (p21, Cip1) | 3.6 | Cytosol and Nucleoplasm | Cyclin dependent protein kinase inhibitor activity |
| 17 | MAGEA4 | 4103 | Melanoma antigen family A, 4 | 4.7 | Cytoplasm | Unknown |
| 18 | IL23A | 51561 | IL23A interleukin 23, alpha subunit p19 | 3.02 | Cytoplasm | Cytokine activity |
| 19 | PAK3 | 29433 | p21 protein (Cdc42/Rac)-activated kinase 3 | 2.7 | Cytoplasm and Nucleus | p21/Cdc42/Rac1-activated kinase 3, serine/threonine kinase |
| 20 | DPPA2 | 151871 | Developmental pluripotency associated 2 | −11.2 | Nucleus | Nucleic acid binding |
| 21 | ZFP42 | 132625 | Zinc finger protein 42 homolog (mouse) | −22.5 | Nucleus | Transcription factor activity |
| 22 | PNMA5 | 114824 | paraneoplastic antigen like 5 | −19.8 | | |
| 23 | TFF2 | 7032 | Trefoil factor 2 | −16.8 | Extracellular | Unknown |
| 24 | DPEP3 | 64180 | Dipeptidase 3 | −87.8 | Plasma Membrane | Dipeptidase activity |
| 25 | MMP9 | 4318 | Matrix metallopeptidase 9 (gelatinase B, 92 kDa gelatinase, 92 KDa type IV collagenase) | −215.1 | Extracellular | Collagen binding metalloendopeptidase activity |

TABLE 3

Nanogel composition

| Nanogel Code | NIPAM (mg) | VP (mg) | PEG-MA (mg) | SA (mg) |
|---|---|---|---|---|
| NG-70 | 700 | 200 | 100 | — |
| NG-80 | 800 | 100 | 100 | — |
| NG-85 | 850 | 100 | 50 | — |
| PNIPAM-SA | 1000 | — | — | 200 |

TABLE 4

Particle size and zeta potential of PNIPAM-SA nanogel with and without drug

| Sample | DLS$^a$ Diameter (nm) | PI | TEM (nm) | Zeta Potential (mV) |
|---|---|---|---|---|
| Blank nanogel | 98.1 ± 3.6 | 0.103 ± 0.03 | 55.0 ± 2.7 | −14.5 ± 0.30 |
| DAC loaded nanogel | 118.2 ± 3.4 | 0.129 ± 0.03 | 60.1 ± 3.1 | −15.6 ± 0.26 |
| Dox loaded nanogel | 121.7 ± 3.4 | 0.20 ± 0.03 | 61.8 ± 3.0 | −13.9 ± 0.60 |

$^a$Data as mean ± s.e.m. (n = 3)

TABLE 5

Particle size and zeta potential of PNIPAM-VP-PEGMA nanogels with and without drug

| Sample | DLS Diameter (nm) | PI | Zeta Potential (mV) |
|---|---|---|---|
| NG-70 | 233.7 | 0.057 | −24.8 ± 4.3 |
| DAC loaded NG-70 | 244.4 | 0.110 | −19.3 ± 1.0 |
| NG-80 | 126.0 | 0.048 | −19.5 ± 0.9 |

TABLE 5-continued

Particle size and zeta potential of PNIPAM-VP-PEGMA nanogels with and without drug

| Sample | DLS Diameter (nm) | PI | Zeta Potential (mV) |
|---|---|---|---|
| DAC loaded NG-80 | 129.0 | 0.010 | −20.1 ± 0.1 |
| NG-85 | 132.2 | 0.052 | −17.0 ± 0.8 |
| DAC loaded NG-85 | 134.3 | 0.023 | −17.2 ± 2.1 |

REFERENCES

1. Nyce J W. Drug-induced DNA hypermethylation: a potential mediator of acquired drug resistance during cancer chemotherapy. Mutat Res 1997; 386:153-161.
2. Goffin J and Eisenhauer E. DNA methyltransferase inhibitors-state of the art. Ann Oncol 2002; 13:1699-1716.
3. Carr B I, Rahbar S, Asmeron Y, Riggs A and Winberg C D. Carcinogenicity and haemoglobin synthesis induction by cytidine analogues. Br J Cancer 1988; 57:395-402.
4. Brown R and Plumb J A. Demethylation of DNA by decitabine in cancer chemotherapy. Expert Rev Anticancer Ther 2004; 4:501-510.
5. Mund C, Hackanson B, Stresemann C, Lubbert M and Lyko F. Characterization of DNA demethylation effects induced by 5-Aza-2'-deoxycytidine in patients with myelodysplastic syndrome. Cancer Res 2005; 65:7086-7090.
6. Wehbe-Janek H, Shi Q and Kearney C M. Cordycepin/Hydroxyurea synergy allows low dosage efficacy of cordycepin in MOLT-4 leukemia cells. Anticancer Res 2007; 27:3143-3146.
7. Qin J J O M, Cao Y M, Lee L S. Development of a LCST membrane forming system for cellulose acetate ultrafiltration hollow fiber. Sep. purification technol. 2005; 42:291-295.
8. Melixetian M B, Beryozkina E V, Pavlenko M A and Grinchuk T M. Altered expression of DNA-topoisomerase IIalpha is associated with increased rate of spontaneous polyploidization in etoposide resistant K562 cells. Leuk Res 2000; 24:831-837.
9. Walker J V N J. DNA topoisomerase II as a target for cancer chemotherapy. cancer investigation 2002; 20(4): 570-589.
10. Hershman D L, McBride R B, Eisenberger A, Tsai W Y, Grann V R and Jacobson J S. Doxorubicin, cardiac risk factors, and cardiac toxicity in elderly patients with diffuse Bcell non-Hodgkin's lymphoma. J Clin Oncol 2008; 26:3159-3165.
11. Von Hoff D D, Layard M W, Basa P, Davis H L, Jr., Von Hoff A L, Rozencweig M, et al. Risk factors for doxorubicin-induced congestive heart failure. Ann Intern Med 1979; 91:710-717.
12. Hequet O, Le Q H, Moullet I, Pauli E, Salles G, Espinouse D, et al. Subclinical late cardiomyopathy after doxorubicin therapy for lymphoma in adults. J Clin Oncol 2004; 22:1864-1871.
13. Limat S, Demesmay K, Voillat L, Bernard Y, Deconinck E, Brion A, et al. Early cardiotoxicity of the CHOP regimen in aggressive non-Hodgkin's lymphoma. Ann Oncol 2003; 14:277-281.
14. Rottapel R, Ilangumaran S, Neale C, La Rose J, Ho J M, Nguyen M H, et al. The tumor suppressor activity of SOCS-1. Oncogene 2002; 21:4351-4362.
15. Rivenbark A G, Jones W D and Coleman W B. DNA methylation-dependent silencing of CST6 in human breast cancer cell lines. Lab Invest 2006; 86:1233-1242.
16. Lung H L, Bangarusamy D K, Xie D, Cheung A K, Cheng Y, Kumaran M K, et al. THY1 is a candidate tumour suppressor gene with decreased expression in metastatic nasopharyngeal carcinoma. Oncogene 2005; 24:6525-6532.
17. Sutherland K D, Lindeman G J, Choong D Y, Wittlin S, Brentzell L, Phillips W, et al. Differential hypermethylation of SOCS genes in ovarian and breast carcinomas. Oncogene 2004; 23:7726-7733.
18. Park Y, Shon S K, Kim A, Kim K I, Yang Y, Cho D H, et al. SOCS1 induced by NDRG2 expression negatively regulates STAT3 activation in breast cancer cells. Biochem Biophys Res Commun 2007; 363:361-367.
19. Yoshikawa H, Matsubara K, Qian G S, Jackson P, Groopman J D, Manning J E, et al. SOCS-1, a negative regulator of the JAK/STAT pathway, is silenced by methylation in human hepatocellular carcinoma and shows growth-suppression activity. Nat Genet 2001; 28:29-35.
20. Galm O, Yoshikawa H, Esteller M, Osieka R and Herman J G. SOCS-1, a negative regulator of cytokine signaling, is frequently silenced by methylation in multiple myeloma. Blood 2003; 101:2784-2788.
21. Chen C Y, Tsay W, Tang J L, Shen H L, Lin S W, Huang S Y, et al. SOCS1 methylation in patients with newly diagnosed acute myeloid leukemia. Genes Chromosomes Cancer 2003; 37:300-305.
22. Fukushima N, Sato N, Sahin F, Su G H, Hruban R H and Goggins M. Aberrant methylation of suppressor of cytokine signalling-1 (SOCS-1) gene in pancreatic ductal neoplasms. Br J Cancer 2003; 89:338-343.
23. Neuwirt H, Puhr M, Santer F R, Susani M, Doppler W, Marcias G, et al. Suppressor of cytokine signaling (SOCS)-1 is expressed in human prostate cancer and exerts growth-inhibitory function through down-regulation of cyclins and cyclin-dependent kinases. Am J Pathol 2009; 174:1921-1930.
24. Lee T L, Yeh J, Van Waes C and Chen Z. Epigenetic modification of SOCS-1 differentially regulates STAT3 activation in response to interleukin-6 receptor and epidermal growth factor receptor signaling through JAK and/or MEK in head and neck squamous cell carcinomas. Mol Cancer Ther 2006; 5:8-19.
25. Shridhar R, Zhang J, Song J, Booth B A, Kevil C G, Sotiropoulou G, et al. Cystatin M suppresses the malignant phenotype of human MDA-MB-4355 cells. Oncogene 2004; 23:2206-2215.
26. Abeysinghe H R, Pollock S J, Guckert N L, Veyberman Y, Keng P, Halterman M, et al. The role of the THY1 gene in human ovarian cancer suppression based on transfection studies. Cancer Genet Cytogenet 2004; 149:1-10.
27. Vaidyanathan G, Cismowski M J, Wang G, Vincent T S, Brown K D and Lanier S M. The Ras-related protein AGS1/RASD1 suppresses cell growth. Oncogene 2004; 23:5858-5863.
28. McCawley L J and Matrisian L M. Matrix metalloproteinases: multifunctional contributors to tumor progression. Mol Med Today 2000; 6:149-156.
29. Davies B, Miles D W, Happerfield L C, Naylor M S, Bobrow L G, Rubens R D, et al. Activity of type IV collagenases in benign and malignant breast disease. Br J Cancer 1993; 67:1126-1131.
30. Stetler-Stevenson W G. Matrix metalloproteinases in angiogenesis: a moving target for therapeutic intervention. J Clin Invest 1999; 103:1237-1241.

31 May F E, Semple J I, Prest S J and Westley B R. Expression and motogenic activity of TFF2 in human breast cancer cells. Peptides 2004; 25:865-872.

32 Yallapu M M, Vasir J K, Jain T K, Vijayaraghavalu S and Labhasetwar V. Synthesis, Characterization and Antiproliferative Activity of Rapamycin-Loaded Poly(NIsopropylacrylamide)-Based Nanogels in Vascular Smooth Muscle Cells. J Biomed Nanotech. 2008; 6:16-24.

33 Tabuchi Y, Matsuoka J, Gunduz M, Imada T, Ono R, Ito M, et al. Resistance to paclitaxel therapy is related with Bcl-2 expression through an estrogen receptor mediated pathway in breast cancer. Int J Oncol 2009; 34:313-319.

Example 2 Data in Drug Resistant Breast Cancer (MCF-7/ADR)

Materials

N-isopropylacrylamide (NIPAM) was used after re-crystallization from n-hexane:benzene (1:3 v/v). Vinyl pyrrolidone (VP) was distilled just before polymerization. Sodium dodecylsulphate (SDS), sodium acrylate (SA), N,N'-cystaminebisacrylamide (S-S cross linker) and ammonium persulphate (APS) were used without further purification. 5-aza-2'deoxycytidine (decitabine; DAC) and all the chemicals mentioned above were purchased from Sigma Aldrich Chemical Company (St. Louis, Mo.). Materials required for cell culture were purchased from Lerner Research Institute, media lab (Cleveland, Ohio). PEG-maleic anhydride (PEG-MA) was prepared by reacting equimolar ratio of poly (ethylene glycol) (M.W. 5000) and maleic anhydride at an elevated temperature as reported else where (Chan C K and Chu I M, Mater Chem Phys 2004, 88:59-66).

PNIPAM Nanogel Synthesis

Nanogel was synthesized by surfactant polymerization, using NIPAM in presence of S-S cross linker and APS as initiator at 70° C. for 6 h. Briefly, 700 mg of NIPAM, 200 mg of SDS, 200 mg of VP and 100 mg of PEG-MA in 100 mL of MiliQ water was stirred under nitrogen for 30 min at room temperature to get uniform solution. The reaction temperature was raised to 70° C. and 80 mg of APS was added to initiate the reaction. Reaction was continued for 6 h at this temperature. The obtained nanogel solution was dialyzed against Mili Q water (2 L) using Spectropore® dialysis bag (mol wt cutoff 12-kD, Spectrum®, Lagunahills, CA) for 2 weeks to remove un-reacted monomer, surfactant and electrolytes by changing water every day. The aqueous solutions of nanogel was lyophilized (−80° C., <10 µm mercury pressure, Sentry™, Virtis, Gardiner, N.Y.) for 48 h to get dry powder. The resulted nanogels were characterized for size by dynamic light scattering (DLS) and transmission electron microscopy (TEM). Nanogels were loaded with DAC.

DAC Loading in Nanogel

DAC in DMSO (300 µL, 8.1 mg/mL) was added to nanogels dispersed in MiliQ water (5 mg/mL, 6 mL) and stirred for 3 h on a magnetic stirrer in cold room. Post stirring, dialyzed against MiliQ water in a dialysis bag (MWCO 12-kD, Spectrum®, Laguna Hills, Calif.) for 30 min to remove un-entrapped drug and then lyophilized. Drug loading was estimated by extracting the drug in methanol from the lyophilized nanogels. The drug concentration was determined using HPLC. A standard plot of DAC (0-200 µg/mL) was prepared under identical conditions.

Physical Characterization of Nanogels

The mean hydrodynamic particle size of nanogels before and after drug loading was determined in water by DLS at a scattering angle of 90° at 25° C. using NICOMP™380 ZLS (Particle Sizing Systems, Santa Barbara, Calif.). Nanogels sizes were also determined by TEM (Philips 201 TEM, Philips/FEI Inc., Briarcliff Manor, N.Y.) operating at 200 kV. A drop of nanogel suspension in water (500 µg/ml) was placed on 200 mesh formvar-coated copper TEM grid (TEDPELLA, Redding, Calif., USA) to which 2% w/v of uranyl acetate solution (negative stain) was added. Samples were allowed to dry in air for 5 h prior to imaging. From TEM images nanogels size were measured using image J software.

Western Blotting

Proteins (50-100 m/lane) from DAC treated or untreated cell lysates in RIPA buffer were probed for mouse monoclonal P-glycoprotein (calbiochem) and mouse anti-actin (Sigma-Aldrich, St. Louis, Mo.). Blotting and detection of the indicated proteins were done as per standard western blot protocol.

Cell Viability Assay

Cytotoxicity of DAC in solution vs. DAC loaded nanogel was compared at day 5, 10 or 12 post drug additions in drug resistant cells. In a typical experiment; cells were seeded at 3000 cells/well in 96 well plates. 24 h post seeding, 0.1 mL cell culture media containing different concentrations of DAC solution or DAC nanogel was added and incubated for 3 d. Post incubation; cells were washed with 1×-DPBS and then replaced with drug free medium at every 48 h until cell viability was measured via an MTS assay kit (Promega CellTiter 96 AQueous Promega, Madison, Wis.). The effects of the drug on cell proliferation were calculated as the percentage cell growth vs. growth of control cells that received no drug treatment.

Cellular Uptake Studies

Drug resistant breast cancer cells were seeded in 24 well plates (1.2×106 cells/well). Post 48 h seeding, cells were pre-treated with DAC (50 ng/mL; 24 h); and then incubated with fixed concentration of dox (1 µg/mL) for indicated time points. Post drug incubation cell lysates in RIPA buffer was collected and lyophilized. Dox was extracted from lyophilized cell lysates using methanol as the solvent and analyzed by HPLC.

In Vivo Anti-Tumor Efficacy of DAC Nanogels

A murine drug-resistant breast cancer model (MCF-7/ADR) was used to investigate the anti-tumor efficacy of DAC nanogels. To establish tumors, 1×106 MCF-7/ADR cells were suspended in 100 µL of matrigel (BD biosciences San Jose, Calif.) and injected in the mammary fat pad via a 27 G ½ gauge needle. Tumor nodules were allowed to grow to about 300 mm3 prior to receiving DAC nanogels (drug dose 15 mg/kg) or its respective controls (DAC in solution or Control Nanogels) intravenously. Post single treatment, tumor dimensions were measured with a digital caliper at regular time intervals and the tumor volume was calculated using the formula $[length \times (width)^2]/2$. End point of this in vivo study includes tumor size that exceeded 10% of the normal b·wt. and/or weight loss greater than 20% of body weight, which indicated toxicity of the formulations used. Data were expressed as mean±SEM (n=3 to 6). Variances in tumor growth were determined using one-way ANOVA test followed by Tukey test using GraphPad Prism version 4.0 for Windows ($p<0.05$).

Results

Cellular Uptake of Dox in DAC Pre-Treated Drug Resistant Cells

Figure 8A:
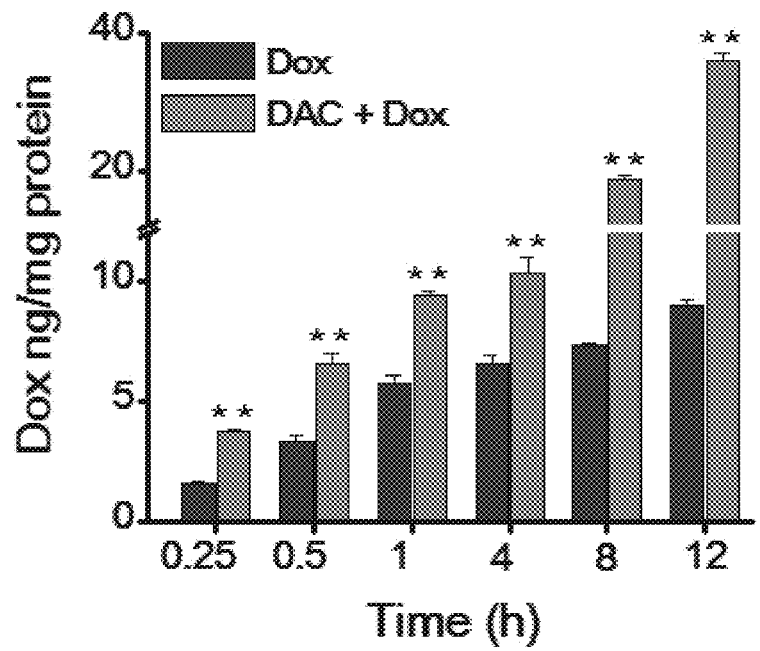

Time course uptake of dox, in dox alone treated MCF-7/Adr cells showed a slow uptake of the drug. The drug concentration reached plateau after 1 h of incubation. No further significant increase in drug uptake was observed for rest of the time points studied. Indicating these cells maintain low intracellular dox levels to avoid cytotoxicity. Cells pre-treated with DAC showed a higher increase in uptake of dox at 15 min itself and then continued to increase significantly until 12 h than dox alone treated cells (FIG. 8a). The initial increase in dox uptake in DAC pre-treated cells indicates the influence of epigenetic drug (DAC) in altering the membrane lipid composition and thereby increasing the uptake of dox.

Figure 8B:
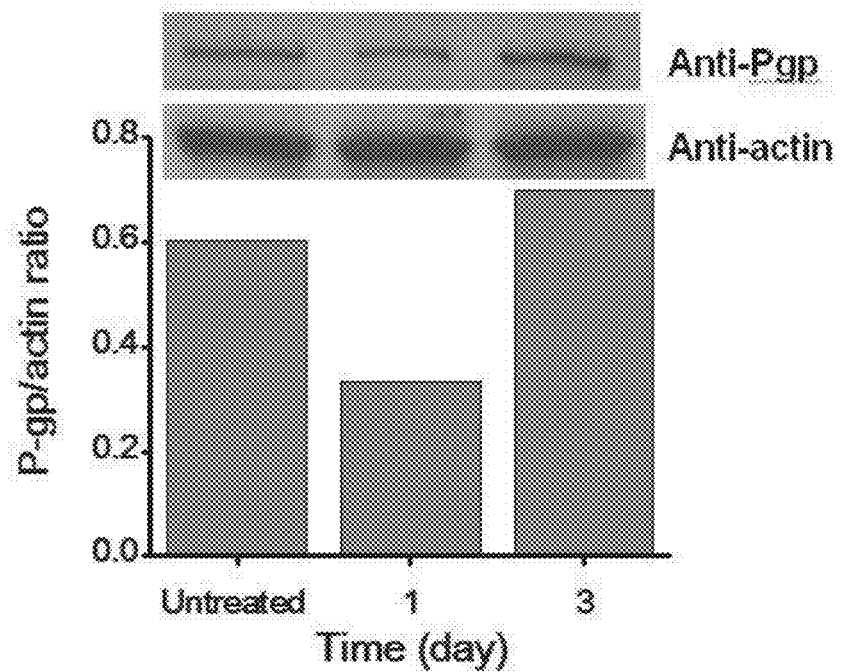
Figure 8D:
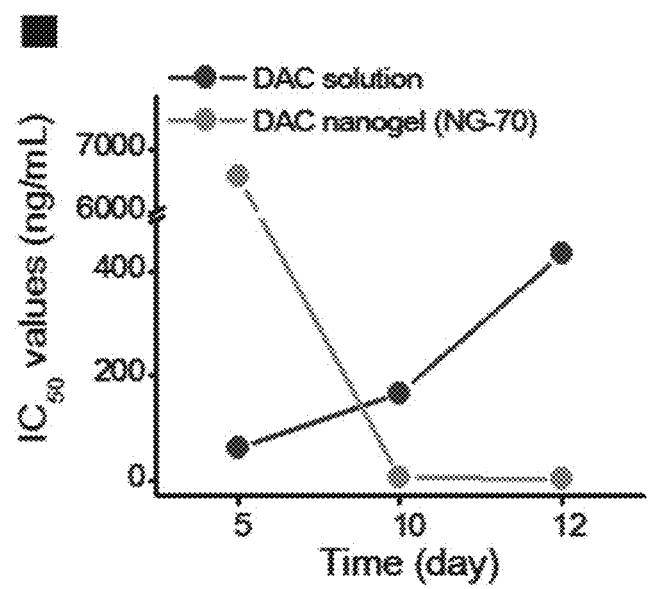
Figure 8E:
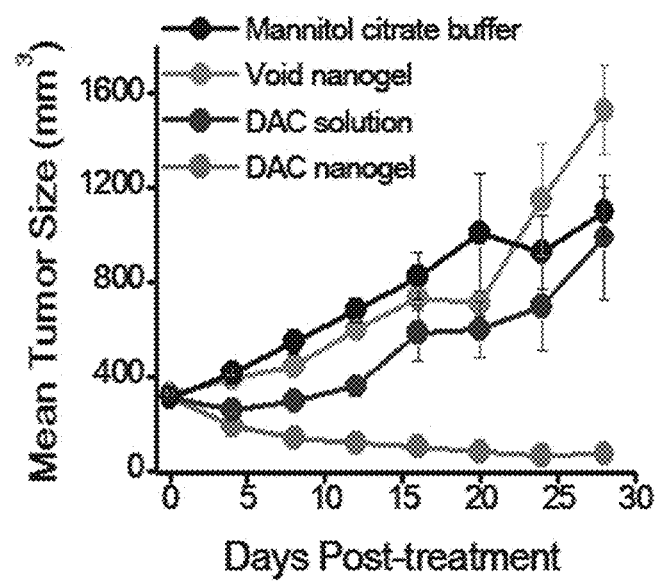

DAC Treatment Suppresses P-Gp (Efflux Pump) Protein Expression in MCF-7/Adr Cells To understand the mechanism behind the increased dox uptake and to correlate it to the P-gp efflux in DAC treated resistant cells, the P-gp levels in cells treated with and without DAC were monitored. Western blot analysis of P-gp shows 45% decrease in cells treated with DAC at day 1 than untreated cells (FIG. 8b). P-gp expression returned to normal levels at day 3. The transient drug effect was likely due to its instability in cell culture media. DAC degrades rapidly in aqueous solutions. However, suppression of P-gp for 24 h was effective enough to increase the cellular uptake of dox initially, which is likely sufficient to enhance the cytotoxicity of dox.

Physical Characterization of Nanogels

To improve the stability and efficacy of DAC, DAC was encapsulated in nanogel. Hydrodynamic particle size distribution and Transmission electron microscopy showed the particle size to be 233 nm with PI of 0.06 and 75±8 nm respectively. Nanogels with and without drug showed no significant difference in size and zeta potential. Both the formulations showed negative zeta potential in water. Loading of DAC in nanogels were at the range of 6-8 wt %.

Comparison of Efficacy of DAC Nanogels and DAC Solution in Drug Resistant Breast Cancer Cell MTS assay results of MCF-7/Adr cells treated with DAC nanogel showed better antiproliferative activity than DAC solution for longer period of time. At day 12 post drug treatment $IC_{50}$ value of DAC nanogel (1.3 ng/mL) was significantly reduced on comparison to DAC in solution (434.2 ng/mL). Since DAC in solution degrades rapidly in cell culture media, loading of DAC in nanogel likely enhanced its stability which in-turn increased its efficacy.

Anti-Tumor Activity of DAC Loaded Nanogel in Animal Model

A single-dose of intravenous injection of DAC loaded nanogel at 15 mg/kg b·wt showed significant tumor inhibition as compared to animals which received DAC in solution, Void nanogel or Mannitol citrate buffer. DAC has a short in vivo half life (10-30 min) and poor plasma protein binding. Increased efficacy of DAC nanogels indicated that the nanogels have increased the in vivo stability of DAC. In addition due to small size, nanogels effectively accumulated in tumor due to EPR effect. Thus DAC loaded nanogels can be used to address drug resistance in cancer.

Example 3 Effect of Decitabine on Exosomes: Possible Mechanism for Inhibition of Tumor Metastasis Exosomes are nanovesicles secreted by tumor cells and have roles in paracrine signaling during tumor progression, including tumo-stromal interactions, activation of proliferative pathways and bestowing immunosuppression.

Exosome Isolation Protocol

Exosome isolation protocol: MDA-MB 231 cells were grown in DMEM supplemented with 10% fetal bovine serum (FBS), and 1% antibiotics. Prior to use in cell culture; the cell culture medium was depleted of endogenous exosomes present in FBS. Exosomes depleted media were prepared by 16 h of ultracentrifugation of cell culture medium supplemented with 50% FBS at 100, 000×g and filtered through 0.2 µm filter. Through out this process sterile conditions were maintained.

To isolate the exosomes from cells treated with DAC, cells were cultured in 10 cell culture dishes (150×25 mm), When the cells were at 70% confluency, the cells were washed with 1×PBS, re-fed with endogenous exosomes depleted media containing DAC (0.5 µM) and incubated for 24 h. Because of small production of exosomes from cultured cells, culture media from all the DAC treated plates were pooled for exosome isolation. All the exosome isolation procedures were done at 4° C. Culture supernatants were first centrifuged at 300×g for 10 min to pellet the cells. To remove the dead cells, supernatant was centrifuged at 2,000×g for 15 min (Sorvall Legend RTcentrifuge, Thermo Electron Corp. Waltham, Mass.). Supernatant was pipetted off and transferred to pre-cooled polycarbonate tubes appropriate for 50.1Ti fixed angle ultracentrifugation rotor (Beckman Coulter Inc., Fullerton, Calif., USA) and centrifuged at 10,000×g for 30 min to remove cell debris. Pellet was discarded and supernatant was aliquoted to several ultracentrifuge tubes and centrifuged at 110,000×g for 70 min to pellet exosomes. Supernatant was discarded. The pellet in each tube was re-suspended in 1 mL PBS and pooled in to single ultracentrifuge tube and centrifuged at 110,000×g for 70 min. This step was repeated twice to remove the protein contamination. The final pellet was re-suspended in 100 µL of PBS and lyophilized for lipid analysis or for size characterization by Dynamic Light Scattering (DLS). For characterization by Transmission Electron Microscopy, the final pellet was re-suspended in 50 µL of 2% paraformaldehyde and fixed overnight at 4° C. A similar protocol was used to isolate the exosomes from untreated cells also.

Transmission Electron Microscopy Sample Preparation

Five micro-liter of PFA fixed exosome suspension was dropped on 200 mesh formvar—carbon coated EM grid (grid size: 97 µm) (TEDPELLA, Redding, Calif., USA) and exosomes were allowed to adsorb to the grids by drying the suspension at room temperature for 20-30 min. Two to three grids was prepared for each exosome preparation. The exosomes were washed thrice 5 min each with PBS. Exosomes were fixed again with 2.5% glutaraldehyde for 5 min. Post glutaraldehyde fixation, exosomes were washed 6-8 times each 2-3 min with sterile Mili Q water. Exosomes were stained with 2% w/v uranyl acetate solution (negative stain) for 5 min. The excess stain was wicked away with filter paper and samples were allowed to dry in air for 5 h prior to imaging. From TEM images sizes of exosomes were measured using Image J software.

Result

Physical Characterization of Exosomes:

Hydrodynamic diameter of exosomes collected from untreated and DAC treated metastatic breast cancer (MDA-MB 231) cells were 380 nm; PI—0.55 and 495 nm with the PI of 0.61 respectively. Similarly, size measurement by transmission electron micrograph showed difference in exosomes from untreated vs. treated cells (66.6±8.3 vs. 97.2±8.0). While preparing samples for transmission electron microscopy (TEM) it was observed that untreated exosomes bound poorly to the copper grids as compared to DAC treated exosomes; this is likely due to alteration in membrane properties of DAC treated exosomes. In a drug resistant cell line (MCF-7/ADR) DAC alters the membrane lipids. It is likely that DAC treatment altered the membrane lipids of exosomes. Exosomes play important role in extracellular matrix immune suppression which helps in tumor growth. They are also considered responsible for promoting tumor metastasis as they migrate to distal sites and create suitable environment for tumor cells to anchor and promote growth. Because of the changes in exosomes following DAC treatment, they either could not migrate (due to increased size or change in lipid composition) or were unstable in the circulation and hence could not localize to distal sites to promote metastasis. One significant observation was that the tumors from animals treated with DAC-nanogel were easy to isolate and remove (as if it was an isolated mass) whereas the tumors removed from control animals results significant bleeding. It appeared that there was no tumor angiogenesis in DAC-nanogel treated animals. See FIGS. 9a-9c.

Example 4 Study in Breast Tumor Metastasis Model (MDA-MB-231-Luc-D3H2LN)

In Vivo Anti-Tumor Efficacy of DAC Nanogels

A murine metastatic breast cancer model was used to investigate the anti-tumor efficacy of DAC nanogels. To establish metastasis model, athymic nude mice were injected with 50 μL of $2 \times 10^6$, luciferase expressing metastatic breast cancer cells (MDA-MB-231-luc-D3H2LN) suspended in 50% PBS/50% matrigel in to the abdominal mammary fat pad via 30 G ½ gauge needle. Tumor nodules were allowed to grow to about 50-100 mm3 prior to receiving DAC nanogels (drug dose 10 mg/kg) or its respective controls intravenously. Tumor response to therapy was monitored by manually measuring the tumor size using a digital caliper or by in-vivo bioluminescent imaging of tumor cells. Prior to imaging, animals were anesthetized by exposure to mixture of oxygen and isoflurane 1-3%. The substrate luciferin (Caliper Life Sciences, Hopkinton, Mass.) in saline (15 mg/mL) was injected intraperitoneally at a dose of 150 mg/kg body weight. Twelve min post injection, anesthetized animals were placed in IVIS 100 system (Xenogen, Alameda, Calif.), and imaged from the ventral view. The bioluminescence signals were quantified by the Living Image® software. A typical exposure time was 3 s for orthotopic xenografts and 1-2 min for ex-vivo imaging were kept constant for all the animals. Binning number was set to medium. Analyses of the images were preformed by drawing a region of interest (ROI) over the tumor/organs (ex-vivo) to obtain the normalized photons per second over the ROIs. End point of this in vivo study includes tumor size that exceeded 10% of the normal body weight and/or weight loss greater than 20% of body weight, which indicated toxicity of the formulations used. To monitor the lymph node metastasis, DAC treated and controls animals were sacrificed at 6 or 7 wk post tumor inoculation, organs excised from animals and bioluminescent imaging was done. For ex-vivo imaging, luciferin (150 mg/kg) was injected into the mice 12 min prior to necropsy. Tissues of interest were excised and placed in the Petri plates containing PBS and imaged at the exposure of 3 min. See FIG. 10.

Example 5 More Detailed Protocol/Results for Animal Studies

In vivo anti-tumor efficacy of DAC nanogels in athymic nude mice bearing MCF-7/Adr xenograft tumor: To establish tumors, 1×106 MCF-7/Adr cells were suspended in 100 μL of matrigel (BD biosciences San Jose, Calif.) and injected in the mammary fat pad via a 27 G ½ gauge needle. Tumor nodules were allowed to grow to about 300 mm3 prior to receiving a single dose of DAC-loaded nanogels (drug dose 15 mg/kg) or controls (DAC in solution or Control Nanogels) intravenously. Tumor dimensions were measured with a digital caliper at regular time interval and the tumor volume was calculated using the formula [length× (width)2]/2. Data were expressed as mean±SEM (n=3 to 6). Variances in tumor growth were determined using one-way ANOVA test followed by Tukey test using GraphPad Prism version 4.0 for Windows (p<0.05).

In Vivo Anti-Tumor Efficacy of DAC Nanogels in Athymic Nude Mice Bearing Metastatic Breast Cancer (MDA-MB 231) Tumor To establish metastasis model, athymic nude mice were injected with 50 μL of 2×106, luciferase expressing metastatic breast cancer cells (MDA-MB-231-luc-D3H2LN) suspended in 50% PBS/50% matrigel into the abdominal mammary fat pad via 30 G ½ gauge needle. Tumor nodules were allowed to grow to about 50-100 mm3 prior to receiving DAC nanogels (drug dose 10 mg/kg) or controls intravenously. Tumor response to therapy was monitored by manually measuring the tumor size using a digital caliper or by in-vivo bioluminescent imaging of tumor cells. Prior to imaging, animals were anesthetized by exposure to mixture of oxygen and isoflurane 1-3%. The substrate luciferin (Caliper Life Sciences, Hopkinton, Mass.) in saline (15 mg/mL) was injected intraperitoneally at a dose of 150 mg/kg body weight. Twelve min post injection, anesthetized animals were placed in IVIS 100 system (Xenogen, Alameda, Calif.), and imaged from the ventral view. The bioluminescence signals were quantified by the Living Image® software. A typical exposure time was 3 s for orthotopic xenografts and 1-2 min for ex-vivo imaging were kept constant for all the animals. Binning number was set to medium. The images were analyzed by drawing the region of interest (ROI) over the tumor/organs (ex-vivo) to obtain the normalized photons per second over the ROIs. To monitor the lymph node metastasis, DAC treated and controls animals were sacrificed at 6 or 7 wk post tumor inoculation, organs excised from animals and bioluminescent imaging was done. For ex-vivo imaging, luciferin (150 mg/kg) was injected into the mice 12 min prior to necropsy. Tissues of interest were excised and placed in the Petri plates containing PBS and imaged at the exposure of 3 min. See FIG. 8c.

Example 6 Decitabine (DAC)-Loaded Nanogels can Overcome Decitabine Resistance

Examples are melanoma (B15) and leukemia (THP1) cells which are resistant to decitabine.

Cell Culture Condition

Drug resistant breast cancer (MCF-7/Adr) cells were grown in Dulbecco's modified Eagle's (DMEM) supplemented with 15% fetal bovine serum (FBS) and 100 μg/mL penicillin G and 100 μg/mL streptomycin at 37° C. in a humidified and 5% CO2 atmosphere. Decitabine-resistant melanoma (B16 res) and -sensitive (B16) cells were grown DMEM supplemented with 10% FBS and antibiotics at 37° C. in CO2 incubator. Decitabine resistant leukemia cells were cultured using conditions similar to melanoma cells.

Cell Viability Assay in Drug Resistant Breast Cancer (MCF-7/Adr) Cells

Cytotoxicity of DAC in solution vs. different DAC loaded nanogel formulations was compared at day 5, 10 or 12 post drug additions in drug resistant cells. In a typical experiment, cells were seeded at 3000 cells/well in 96 well plates. Twenty four hr post seeding, 0.1 mL cell culture media containing different concentrations of DAC solution or DAC nanogel was added and incubated for 3 d. Post incubation, cells were washed with 1×-DPBS and then replaced with drug free medium at every 48 h. Cell viability was measured using MTS (Promega CellTiter 96 AQueous Promega, Madison, Wis.). The effects of the drug on cell proliferation were calculated as the percentage cell growth vs. growth of control cells that received no drug treatment.

Cell Viability Assay in Decitabine-Resistant Melanoma (B16 Res) and -Sensitive Melanoma (B16) Cells Cytotoxicity of DAC in solution vs. DAC loaded nanogel was studied at 3 and 6 post treatment in DAC resistant melanoma cancer cells. In a typical experiment, cells were seeded at 2,000 cells/well/0.1 mL in 96-well plates (Microtest, Becton Dickinson Labware, Franklin Lakes, N.J.). Following 24 h incubation, cells were incubated for 3 d in a medium containing different concentrations of drug (DAC solution or DAC loaded different nanogel formulations). Cells were washed with DPBS, and cell viability was measured using MTS assay. In the experiment involving 6 d treatment, cells were incubated with drug for 3 d as above and then replaced with drug free medium and incubated for additional 3 d and then MTS assay was done. An aliquot of 20 µL of the MTS reagent was added to each well, the plates were incubated for 2 h at 37° C., and color intensity was measured at 490 nm using a plate reader (Bio-Tek Instruments, Inc., Winooski, Vt.). The effects of the drug on cell proliferation were calculated as the percentage cell growth vs. growth of control cells that received no drug treatment. Identical protocol was used to determine cytotoxicity of DAC in sensitive cells. Similar protocol was followed for DAC resistant leukemia (THP1) cells to asses the efficacy of DAC solution or DAC nanogel.

Western Blot for DNMT1

Cells (B16 res, B16 and THP1) were seeded (5×106 cells/dish) in 100-mm cell culture dishes (BD Biosciences) and incubated for 24 h in CO2 incubator for attachment. Cells were treated with DAC solution or DAC nanogel. Cellular extracts generated at day 1, day 3 and day 5 post treatment were assessed by western blot using anti-DNMT1 monoclonal antibody or with anti-actin monoclonal antibody (loading control). Whole cell lysates, were made by lysing 1×106 treated or untreated cells, with RIPA buffer (Sigma-Aldrich, St. Louis, Mo.) containing 1× protease inhibitor cocktail (Calbiochem, Gibbstown, N.J.). Lysates were collected by centrifugation at 14,000 rpm for 15 min. Protein concentration was determined by a bicinchoninic acid (BCA) assay kit (Pierce, Rockford, Ill.). 50-100 µg proteins of cell lysates were electrophoresed through 4-15% linear pre-cast polyacrylamide gradient gel (Bio-Rad Laboratories, Hercules, Calif.) and transferred to polyvinylidene difluoride (PVDF) membranes (GE Healthcare Bio-sciences, corp., Piscataway, N.J.). The blots were probed for mouse monoclonal DNMT1 (Abcam Inc., Cambridge, Mass.), and mouse monoclonal anti-actin (Sigma-Aldrich, St. Louis, Mo.). For detection of bound antibody, PVDF membrane was incubated with horse radish—tagged, goat anti-mouse antibody. After incubation membrane was washed with TBST, and stained with enhanced chemiluminescence (ECL) reagent or ECL plus reagent (GE Healthcare Bio-sciences, corp., Piscataway, N.J.) according to manufacturer protocol.

Conclusions

DAC in nanogel deliver drug inside cells, bypassing efflux transporters, and sustains the drug effect to suppress DNMT1 level. DNAMT1 is an enzyme that promotes methylation of DNA. See FIGS. 12-17.

Example 7 Combination of DAC and SAHA in Nanogels

Method

Cells seeded in 96 well plates (3,000 cells/well/0.1 mL) and allowed to attach for 24 h in CO2 incubator. Cells were treated with single dose of DAC nanogel or SAHA-Nanogel+DAC nanogel (NG-70) simultaneously or sequentially, and incubated for 72 h. Cells were washed with PBS and incubated additionally for another 48 h and cell viability was measured using MTS reagent as per manufacturers protocol.

Results

Resistant breast cancer (MCF-7/Adr) cells were treated with the combination of DAC-loaded nanogel and SAHA-loaded nanogels (two separate formulations). Cells were treated with SAHA nanogel (drug dose 0.5 µM) and different doses of DAC-loaded nanogels. SAHA alone at the dose used had insignificant cytotoxic activity, only 10% cell died. However, the combination of SAHA-nanogel and DAC-nanogel show highly synergistic effect than DAC-Nanogel or SAHA-nanogel alone (FIG. 18). Although in this study two separate formulations were prepared, it is feasible to load both the drugs in one Nanogel formulation at optimal ratio to achieve the synergistic effect.

Example 8 Nanogel Synthesis

Materials

N-isopropylacrylamide (NIPAM) was used after re-crystallization from n-hexane:benzene (1:3 v/v). Vinyl pyrrolidone (VP) was distilled just before polymerization. Sodium dodecylsulphate (SDS), sodium acrylate (SA), N,N'-cystaminebisacrylamide (S-S cross linker) and ammonium persulphate (APS) were used without further purification. The DNA methyltransferases inhibitor 5-aza-2'deoxycytidine (DAC) and all the chemicals mentioned above were purchased from Sigma Aldrich Chemical Company (St. Louis, Mo.). Cell culture Media's, DPBS, Penicillin and Streptomycin were purchased from Lerner Research Institute, media lab (Cleveland, Ohio). MTS reagent was purchased from Promega (Madison, Wis.). PEG-maleic anhydride (PEG-MA) was prepared by reacting equimolar ratio of poly (ethylene glycol) (M.W. 5000) and maleic anhydride at an elevated temperature as reported elsewhere [Chan CK and Chu I M, Mater Chem Phys 2004, 88:59-66].

PNIPAM Nanogel Synthesis

PNIPAM (poly-N-isopropylacrylamide) nanogel was synthesized by surfactant polymerization, using NIPAM in presence of S-S cross linker and APS initiator. The polymerization was conducted in a three-necked flask with nitrogen inlet and outlet at 70° C. for 6 h. Three formulations namely NG-70, NG-80, and NG-85 were prepared; their composition is mentioned in table 1. NG-70 was prepared by dissolving 700 mg of NIPAM, 200 mg of SDS, 200 mg of VP and 100 mg of PEG-MA in 100 mL of MiliQ water and stirred under nitrogen for 30 min at room temperature in order to obtain uniform solution. The reaction temperature was raised to 70° C. and 80 mg of APS dissolved in 5 mL for about 5 min was introduced to initiate the reaction. Reaction was continued for 6 h at this temperature. The obtained nanogel suspension was dialyzed against Mili Q water (2 L) using Spectropore® dialysis bag (mol wt cutoff 12-kD, Spectrum®, Laguna-hills, CA) for 2 weeks to remove un-reacted monomer, surfactant and electrolytes by changing water every day. The suspension of nanogel from the dialysis bag was lyophilized (−80° C., <10 µm mercury pressure, Sentry™, Virtis, Gardiner, N.Y.) for 48 h to get dry powder. Other two nanogel formulations (NG-80 and NG-85) were synthesized using the same protocol. Nanogel formulations were characterized for size by dynamic light scattering (DLS) and transmission electron microscopy (TEM). Nanogels were loaded with DAC as follows.

DAC Loading in Nanogel

DAC in DMSO (300 µL, 8.1 mg/mL) was added to nanogels dispersed in MiliQ water (5 mg/mL, 6 mL). DAC added nanogel suspension was stirred for 3 h on a magnetic stirrer in cold room. DAC loaded nanogel suspension was dialyzed against MiliQ water in a dialysis bag (MWCO 12-kD, Spectrum®, Laguna Hills, Calif.) for 30 min to remove unentrapped drug. The nanogel suspension was lyophilized for further study.

DAC Loading Estimation

Drug loading was estimated by extracting drug from lyophilized drug loaded nanogels. Briefly, 2 mL of methanol was added to 1 mg of nanogels and stirred overnight on a magnetic stirrer at 100 rpm for 12 h at 4° C. 1 mL of methanolic solution was drawn in 1.5 mL eppendorf tube and centrifuged at 14,000 rpm for 10 min at 4° C. to remove nanogels. DAC concentration in supernatant was determined using HPLC (Shimadzu Scientific Instruments, Inc., Columbia, Md.). A standard plot of DAC (0-200 µg/mL) was prepared under identical conditions.

HPLC Conditions

Stationary phase: C18 reversed phase column (Atlantis T3-4.6×250 mm2-5 µm); Mobile phase: Sterile degassed methanol: water (60:40 v/v); Injection vol: 25 µL; Flow rate: 1.2 mL/min, isocratic mode for 6 min wavelength—228 nm, UV detector.

Physical Characterization of PNIPAM-VP-PEGMA Nanogels

Particle Size and Zeta Potential Measurements

The mean hydrodynamic particle size of nanogels before loading and after loading the drug was determined in water by DLS at a scattering angle of 90° at 25° C. using NICOMP™380 ZLS (Particle Sizing Systems, Santa Barbara, Calif.). The suspension of nanogels prepared in water was used to measure zeta potential in phase analysis mode and the current mode at a scattering angle of −14°.

different doses of void nanogels (0-500 µg/mL), dispersed in cell culture media were added and incubated for 72 h. Medium in the wells was changed after 72 h and on every alternate day thereafter with no further addition of nanogels. Cell viability was done on eighth day using MTS assay.

Cell Culture Condition

Cells were grown in DMEM supplemented with 10% fetal bovine serum (Gibco BRL, Grand Island, N.Y.) and 100 µg/mL penicillin G and 100 µg/mL streptomycin at 37° C. in a humidified and 5% CO2 atmosphere.

Result

Physical Characterization of PNIPAM-VP-PEGMA Nanogels

Hydrodynamic diameter of void and drug loaded nanogels (NG-80 and NG-85) were at the range of 125 to 135 nm (FIG. 19). NG-70 shown increase in size (234 nm) than other nanogels, this might be due to increase in % VP in it. VP increases hydrophilicity and water flux of a system [2], and it could be a reason for observed significant increase in size of NG-70 in comparison with other two nanogel formulations by DLS measurement. All nanogel formulations with and without drug showed negative zeta potential in water. Size measurement by transmission electron micrograph showed nanogels to be in the range of 60-80 nm (FIG. 19).

Loading of DAC in PNIPAM-VP-PEGMA nanogels were at the range of 6-8 wt %. No difference in loading was observed between NG-80 and NG-85. DAC loading was higher in NG-70 in comparison to other two nanogels.

Nanogel Composition

| Nanogel Code | NIPAM (mg) | VP (mg) | PEG-MA (mg) |
|---|---|---|---|
| NG-70 | 700 | 200 | 100 |
| NG-80 | 800 | 100 | 100 |
| NG-85 | 850 | 100 | 50 |

Particle Size and Zeta Potential of PNIPAM-PEGMA Nanogels with and without Drug

| Nanogels | | % Loading Efficiency | % Loading Content | DLS diameter (nm) | PI | TEM | Zeta (mV) |
|---|---|---|---|---|---|---|---|
| NG-70 | Without drug | — | — | 233 | 0.06 | 75 ± 8 | −25 ± 4.0 |
| | With drug | 99 | 7.96 | 244 | 0.11 | 85 ± 9 | −19 ± 1.0 |
| NG-80 | Without drug | — | — | 129 | 0.05 | 59 ± 5 | −20 ± 1.0 |
| | With drug | 73 | 6 | 126 | 0.01 | 61 ± 6 | −20 ± 0.1 |
| NG-85 | Without drug | — | — | 132 | 0.05 | 65 ± 6 | −17 ± 0.8 |
| | With drug | 70 | 6 | 134 | 0.02 | 66 ± 5 | −17 ± 2.0 |

Transmission Electron Microscopy

Nanogels were characterized for size using transmission electron microscope (TEM) (Philips 201 TEM, Philips/FEI Inc., Briarcliff Manor, N.Y.) operating at 200 kV. For TEM measurements, a drop of nanogel suspension (500 µg/ml) prepared in water was placed on 200 mesh formvar-coated copper TEM grid (grid size: 97 µm) (TEDPELLA, Redding, Calif., USA) to which 2% w/v of uranyl acetate solution (negative stain) was added. The excess solution was removed using a piece of filter paper and the samples were allowed to dry in air for 5 h prior to imaging. From TEM images nanogels size were measured using image J software.

PNIPAM-VP-PEGMA Nanogel Cytocompatibility

Human vascular smooth muscle cells (Cascade Biologics, Portland, Oreg.) were maintained in medium 231 supplemented with smooth muscle growth supplement (Cascade Biologics) at 37° C. in a humidified, 5% CO2 atmosphere. Cells at passage 5 were typically used. 5,000 cells/0.1 mL/well were seeded in 96 well plates. 24 h post seeding, Example 9 Loading of Doxorubicin and Decitabine Together in Nanogels Aim To load doxorubicin (dox) and decitabine in PNIPAM nanogel.

Materials

Doxorubicin.HCl (dox HCl; 49 mg), Hydrophobic dox (5 mg/mL) in ethanol, decitabine (8.1 mg/mL in DMSO), PNIPAM nanogel (31.08 mg), clean glass vial, magnetic stir bar and magnetic stirrer.

Method

Conversion of dox—HCl (Salt) to hydrophobic dox (Base) (water insoluble):

Step 1: dox-HCl (49 mg) weighed out in a small beaker. To it 14 mL of 12.5% v/v methanol in chloroform was added and sonicated briefly.

Step 2: 60 µl of triethylamine was added to the above suspension and stirred for 2-3 h.

Step 3: Post stirring, the suspension was filtered in a pre-weighed 20 mL vial using a 10 mL glass syringe and 0.02 µm filter, additional 1 mL of methanol-chloroform was added to the vial to remove the remaining dox from the filter.

Step 4: Vial was covered with aluminum foil with holes and left in a fume hood (air flow 240 fpm) for the evaporation of organic solvents.

Step 5: The sample was lyophilized to remove the residual organic solvents and stored protected from light at −20° C.

Loading of Dox in Nanogel (Two Batches)

Step 1: Nanogel suspension: 6 mL of MiliQ H2O was added to 31.08 mg of nanogel in 14.8 mL cleaned glass vial.

Step 2: To the above suspension 200 µL (5 mg/mL) of dox base solution in ethanol was added.

Step 3: The suspension was left stirring on a magnetic stirrer for 4 h to load drug with cap closed and 2 h in laminar air flow hood with cap opened.

Step 4: The above suspension was centrifuged at 4,000 rpm for 10 min at 15° C. to remove untrapped dox in nanogel. Centrifugation was repeated for 10 times at the conditions mentioned.

Dox-loaded nanogel was lyophilized for 72 h. One batch was stored post lyophilisation which served as dox alone loaded nanogels and the other batch was used for loading decitabine so that both the drugs are loaded in the same nanogel.

Loading of Decitabine in Nanogel

Step 1: 6 mL of Mili Q H2O and 300 µL of decitabine (stock conc. 8.1 mg/mL in DMSO) was added to dox loaded nanogel suspension (contains 30 mg nanogel).

Step 2: Vial was covered with aluminum foil and stirred in magnetic stirrer for 3 h in cold room.

Step 3: The nanogel suspension was dialyzed against 50 mL MiliQ H2O for 30 min.

Step 4: Dialysate was collected to estimate decitabine that is not loaded into nanogel using HPLC.

Step 5: The nanogel suspension was aliquoted in cryovials and lyophilized for 72 h.

Hydrophobic Dox—Loading Estimation

Drug loading was estimated by extracting drug from lyophilized drug loaded nanogels. Briefly, 12.5% methanol in chloroform, 1 mL was added to 5.9 mg of nanogel and stirred in magnetic stirrer at 100 rpm for 12 h kept at 4° C. 1 mL of extract was collected in 1.5 mL eppendorf tube; vortexed and centrifuged at 14,000 rpm for 10 min at 4° C. Dox concentration in supernatant was determined using HPLC (Shimadzu Scientific Instruments, Inc., Columbia, Md.). A standard plot of hydrophobic dox (0-10 µg/mL) was prepared under identical conditions. Dox concentration was determined using a fluorescence spectrophotometer at $\lambda$ excitation=485 nm and $\lambda$ emission=591 nm.

Decitabine Loading Estimation

The dialysate from the decitabine loading protocol was used to estimate the decitabine loading. Briefly, three samples were drawn randomly from the beaker containing 50 mL of dialysate and used to analyze decitabine concentration by HPLC (Shimadzu Scientific Instruments, Inc., Columbia, Md.). A standard plot of deci (0-200 µg/mL) was prepared under identical conditions.

HPLC Conditions

Stationary phase: C18 reversed phase column (Atlantis T3-4.6×250 mm-5 um); Mobile phase: Sterile degassed methanol: water (60:40); Injection vol: 25 µL; Flow rate: 1.2 mL/min, isocratic mode for 6 min. wavelength—228 nm, UV detector.

Particle Size

The mean hydrodynamic particle size of nanogels before loading and after loading the drug was determined in water by DLS at a scattering angle of 90° at 25° C. using NICOMP™380 ZLS (Particle Sizing Systems, Santa Barbara, Calif.).

Cytotoxicity of Dox and Dox-Decitabine Loaded Nanogels

The efficacy of dox or dox-decitabine loaded nanogels were investigated in dox-resistant human breast cancer cells (MCF-7/Adr). In a typical experiment, cells were seeded at a density of 3,000 cells/well in 96 well plate (Microtest Becton Dickinson Labware, Franklin Lakes, N.J.) and allowed to attach for 24 h. Post attachment, cell culture media was replaced with different concentrations of dox or dox-deci loaded nanogels and incubated in CO2 incubator for additional 72 h. Cells were washed with 1×-DPBS, and then replaced with drug free cell culture media and incubated for additional 48 h. Cell viability was determined at the end of incubation period using a standard MTS assay (CellTiter 96 Aqueous, Promega, Madison, Wis.). To each well 20 µL of reagent was added, and then plates were incubated for 2 h at 37° C. in cell culture incubator. Color intensity was measured at 490 nm using a micro plate reader (Bio-Tek Instrument, Winooski, Vt.). The effect of the drug on cell proliferation was calculated as the percentage cell growth vs growth of control cells that received no drug treatment.

Result and Discussion

Hydrodynamic diameter of void nanogel, nanogel encapsulated with dox alone and/or dox-deci was 106.1 nm 127.5 and 156.2 nm, respectively. Dox loading has insignificant effect on particle size. Dox-deci loaded nanogels showed ~50 nm increase in hydrodynamic size compared with void nanogel. It could be due to loading of hydrophobic drug dox to the core and loading of hydrophilic drug decitabine to the corona of the nanogels, thereby nanogel could have swelled due to drug loading. The $IC_{50}$ values of dox was reduced by 50 folds in dox-decitabine nanogels treated cells than cells treated with nanogels containing only doxorubicin ($IC_{50}$ values—52 vs 2566 ng/mL). See FIG. 20.

Size and Zeta Potential Measurement of Dox or Dox Deci Loaded Nanogels

| | | Characterization | | |
|---|---|---|---|---|
| S. No | Drug Loaded Nanogel | Size (nm) | PI | Zeta Potential (mV) |
| 1 | Void nanogel | 106.6 | 0.177 | −16.45 ± 3.86 |
| 2 | Dox loaded nanogel | 127.5 | 0.258 | −3.87 ± 1.35 |
| 3 | Dox-deci loaded nanogel | 156.2 | 0.318 | −10.86 ± 0.38 |

Decitabine Estimation in Dox-Deci Loaded Nanogel by Indirect Method

| S. No | Drug Loaded nanogel (batch 3) | Initial Conc. of deci (µg) | Conc. of deci in dialysate (µg) | Amount of deci encapsulated (µg) | % Loading efficiency | % Loading Content |
|---|---|---|---|---|---|---|
| 1 | Dox-deci loaded nanogel | 2430 | 580.2 | 1849.8 | 76.1 | 5.95 |

Dox Loading Estimation in Dox or Dox-Deci Loaded Nanogels

| S. No | Drug Loaded nanogel | Initial Conc. of dox (µg) | Conc. of dox in Methanolic extract (µg) | % Loading efficiency | % Loading Content |
|---|---|---|---|---|---|
| 1 | Dox-loaded nanogel | 1000 | 423.2 | 42.3 | 1.4 |
| 2 | Dox-decitabine loaded nanogel | 1000 | 326.9 | 32.7 | 1.1 |

Example 10 DAC Stability in Cell Culture Media

Freshly prepared DAC solution (50 µg/mL) or DAC loaded nanogel (equivalent drug concentration) was added in cell culture media (DMEM supplemented with 15% FBS and 1% penicillin-streptomycin), and incubated in cell culture incubator at 37° C. in a 5% CO2. Samples were incubated as 2 mL aliquots at 37° C., collected at various time points and lyophilized for 48 h at −48° C., 3.5 Pa, using FreeZone 4.5 (Labconco Corp., Kansas City, Mo.). DAC was extracted from lyophilized samples by adding 3 mL of methanol and kept on an orbital rotating shaker at 100 rpm in cold room overnight. 1 mL of methanolic extract was centrifuged at 14,000 rpm for 15 min at 4° C.; supernatant was collected and analyzed by HPLC. Identical protocol was followed for analyzing the stability of DAC in Mili Q water containing 15% heat inactivated or normal serum. Stability of DAC was also analyzed in 15% w/v liver extract of athymic nude mice using the indicated protocol.

HPLC conditions—Stationary phase: C18 reversed phase column (Atlantis T3-4.6×250 mm2-5 µm); Mobile phase: Sterile degassed methanol: water (60:40); Injection volume: 25 µL; Flow rate: 1.2 mL/min, isocratic mode for 6 min wavelength—228 nm, UV detector.

Results

Comparison of Stability of DAC Loaded Nanogel or DAC Solution

The stability study shows that DAC encapsulated in nanogel has greater stability than in solution. DAC in nanogel showed no degradation at 1 h in cell culture medium containing 15% heat inactivated serum and detectable levels of DAC were found till 24 h. However, 60% of DAC in solution degraded within an hour, and no detectable levels of DAC was found at 8 h post incubation (FIG. 22a). Similar results were observed for DAC stability in Mili Q water containing heat inactivated serum or normal serum (FIGS. 22b and 22c). In liver extract from athymic nude mice, DAC in solution degraded completely 60 min post incubation whereas DAC in nanogel was detected upto 240 min (FIG. 22d). These results indicate that stability of DAC increased when encapsulated in nanogel.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A pharmaceutical composition comprising decitabine and doxorubicin in a nanogel, wherein the decitabine and doxorubicin are encapsulated in the same nanogel, wherein the doxorubicin is loaded in the nanogel's core and the decitabine is loaded in the nanogel's corona, and wherein upon contact with tumor cells, the decitabine and doxorubicin are sequentially released from the nanogel with decitabine released first and doxorubicin released later.

2. The pharmaceutical composition of claim 1 wherein the nanogel is about 200 nm or smaller in diameter.

3. The pharmaceutical composition of claim 2 wherein the nanogel is about 50 nm or smaller in diameter.

4. The pharmaceutical composition of claim 1 wherein the nanogel has sustained drug release properties.

5. The pharmaceutical composition of claim 1 wherein the decitabine encapsulated in the nanogel is not metabolized by cytidine deaminase prior to its release from the nanogel.

6. The pharmaceutical composition of claim 1 wherein the decitabine encapsulated in the nanogel alters the formation of exosomes secreted by the tumor cells.

7. The pharmaceutical composition of claim 1, wherein the composition is formulated for administration to said tumor cells by intradermal, intratumoral, intramuscular, intraperitoneal, intraocular, intravenous, subcutaneous, topical, oral or intranasal administration.

8. The pharmaceutical composition of claim 1, wherein the composition inhibits metastatic progression of the tumor cells.

9. The pharmaceutical composition of claim 1, wherein the nanogel improves the stability and reduces in vivo clearance of decitabine.

10. The pharmaceutical composition of claim 6, wherein the altered formation of exosomes inhibits tumor metastasis.

11. The pharmaceutical composition of claim 1, wherein the nanogel comprises sodium acrylate.

12. The pharmaceutical composition of claim 1, wherein the nanogel is prepared from a starting reaction mixture that comprises about 500 mg to about 1000 mg of an N-alkylacrylamide.

13. The pharmaceutical composition of claim 1, wherein the nanogel is prepared from a starting reaction mixture that comprises about 100 mg to about 200 mg of a vinyl polymer.

14. The pharmaceutical composition of claim 1, wherein the nanogel is prepared from a starting reaction mixture that comprises about 50 mg to about 100 mg of a polyalkylene glycol.

15. The pharmaceutical composition of claim 1, wherein the nanogel is prepared from a starting reaction mixture that comprises about 200 mg sodium acrylate.

16. The pharmaceutical composition of claim 12, wherein the N-alkylacrylamide is poly-N-isoprolyacrylamide.

17. The pharmaceutical composition of claim 1, where the composition overcomes drug resistance of the tumor cells.

* * * * *